United States Patent
Jansen et al.

(10) Patent No.: US 9,346,814 B2
(45) Date of Patent: May 24, 2016

(54) FAP INHIBITORS

(71) Applicants: UNIVERSITEIT ANTWERPEN, Antwerpen (BE); Fox Chase Cancer Center, Philadelphia, PA (US)

(72) Inventors: Koen Jansen, Wilrijk (BE); Ingrid De Meester, Wilrijk (BE); Leen Heirbaut, Wilrijk (BE); Jonathan D Cheng, Philadelphia, PA (US); Jurgen Joossens, Wilrijk (BE); Koen Augustyns, Wilrijk (BE); Pieter Van Der Veken, Wilrijk (BE)

(73) Assignees: Universiteit Antwerp, Antwerp (BE); Fox Chase Cancer Center, Philadelphia, PA (US)

( * ) Notice: Subject to any disclaimer, the term of this patent is extended or adjusted under 35 U.S.C. 154(b) by 0 days.

(21) Appl. No.: 14/372,798

(22) PCT Filed: Jan. 17, 2013

(86) PCT No.: PCT/EP2013/050845
§ 371 (c)(1),
(2) Date: Jul. 17, 2014

(87) PCT Pub. No.: WO2013/107820
PCT Pub. Date: Jul. 25, 2013

(65) Prior Publication Data
US 2014/0357650 A1  Dec. 4, 2014

(30) Foreign Application Priority Data

Jan. 17, 2012 (GB) .................................. 1200705.0
Nov. 14, 2012 (GB) .................................. 1220458.2

(51) Int. Cl.
| | | |
|---|---|---|
| C07D 401/12 | (2006.01) |
| C07D 487/04 | (2006.01) |
| C07D 403/12 | (2006.01) |
| C07D 413/12 | (2006.01) |
| C07D 417/12 | (2006.01) |
| C07D 471/04 | (2006.01) |

(52) U.S. Cl.
CPC ............ *C07D 487/04* (2013.01); *C07D 401/12* (2013.01); *C07D 403/12* (2013.01); *C07D 413/12* (2013.01); *C07D 417/12* (2013.01); *C07D 471/04* (2013.01)

(58) Field of Classification Search
CPC .. C07D 401/12; C07D 403/12; C07D 413/12; C07D 471/04; C07D 417/12; A61K 31/401
See application file for complete search history.

(56) References Cited

U.S. PATENT DOCUMENTS 8,183,280 B2 * 5/2012 Evans et al. .................. 514/423
8,754,107 B2 * 6/2014 George et al. ................ 514/326
2011/0230462 A1  9/2011 Hendricks et al.

FOREIGN PATENT DOCUMENTS

| WO | 9532948 | 12/1995 |
| WO | 2007085895 A2 | 8/2007 |
| WO | 2010/083570 A1 | 7/2010 |

OTHER PUBLICATIONS

International Preliminary Report on Patentability completed Mar. 28, 2014 pertaining to International Application No. PCT/EP2013/050845 filed Jan. 17, 2013.
International Search Report and Written Opinion completed Jun. 10, 2013 pertaining to International Application No. PCT/EP2013/050845 filed Jan. 17, 2013.
Database Registry (Online); Chemical Abstracts Service, Columbus, OH, US; Feb. 1, 2000; XP002695552; Database accession No. 1097629-86-1.
Nitz et al., "An Excursion into the Synthesis of Potential Angiotensin Converting Enzyme Inhibitors", The Journal of Organic Chemistry; vol. 47, No. 21, Oct. 1, 1982; pp. 4029-4032; XP055053192; ISSN: 0022-3263, DOI: 10.1021/jo00142a005.
Opacic et al., "The Novel L- and D-Amino Acid Derivatives of Hydroxyurea and Hydantoins: Synthesis, X-ray Crystal Structure Study, and Cytostatic and Antiviral Activity Evaluations", Journal of Medicinal Chemistry; vol. 48, No. 2, Jan. 1, 2005, pp. 475-482; XP0055053198; ISSN: 0022-2623, DOI: 10.1021/jm040869i.
Suzuki et al, "Synthesis and Central Nervous System Actions of Thyrotropin-Releaseing Hormone Analogues Containing a Dihydroorotic Acid Moiety", Journal of Medicinal Chemistry, American Chemical Society, US, vol. 33, No. 8, Jan. 1, 1990, pp. 2130-2137, XP002186256, ISSN: 0022-2623, DOI: 10.1021/JM00170A014.
Acharya, et al., Fibroblast Activation Protein: A Serine Protease Expressed at the Remodeling Interface in Idiopathic Pulmonary Fibrosis, Human Pathology, 2006, vol. 37, pp. 352-360, USA.

(Continued)

*Primary Examiner* — D M Seaman
(74) *Attorney, Agent, or Firm* — Dinsmore & Shohl LLP

(57) ABSTRACT

The present invention relates to novel inhibitors having high selectivity and specificity for FAP (fibroblast activation protein). Said inhibitors are useful as a human and/or veterinary medicine, in particular for the treatment and/or prevention of FAP-related disorders such as but not limited to proliferative disorders.

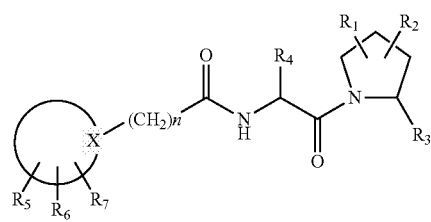

13 Claims, No Drawings

(56) References Cited

OTHER PUBLICATIONS

Brokopp, et al., Fibroblast Activation Protein is Induced by Inflammation and Degrades Type 1 Collagen in Thin-Cap Fibroatheromata, European Heart Journal, doi: 10.1093/eurheartj/ehq519, 2011, pp. 1-10, UK.

Cheng, et al., Abrogation of Fibroblast Activation Protein Enzymatic Activity Attenuates Tumor Growth, Molecular Cancer Therapeutics, mct.aacrjournals.org, American Associate for Cancer Research, 2005, pp. 351-361, USA.

Dienus, et al., Increased Expression of Fibroblast Activation Protein-Alpha in Keloid Fibroblasts: Implications for Development of a Novel Treatment Option, Arch Dermatol Res, 2010, vol. 302, pp. 725-731, Springer, USA.

Kelly, et al., Fibroblast Activation Protein-x: A Key Modulator of the Microenvironment in Multiple Pathologies, Chapter 3, Department of Pathology and Winthrop P. Rockefeller Cancer Institute, University of Arkansas for Medical Sciences, 2012, DOI: 10.1016/B978-0-12, pp. 83-116, USA.

Kraman, et al., Suppression of Antitumor Immunity by Stromal Cells Expressing Fibroblast Activation Protein-x, www.sciencemag.org, Science, vol. 330, Nov. 5, 2010, pp. 827-830, UK.

Laverman, et al., Immuno-PET and Immuno-SPECT of Rheumatoid Arthritis with Radiolabeled Anti-Fibroblast Activation Protein Antibody Correlates with Severity of Arthritis, The Journal of Nuclear Medicine, vol. 56, No. 5, May 2015, pp. 778-784, Netherlands.

Lee, et al., Enhancement of Fibrinolysis by Inhibiting Enzymatic Cleavage of Precursor x2-antiplasmin, 2011 International Society on Thrombosis and Haemostasis, Journal of Thrombosis andHaemostasis, vol. 9, pp. 987-996, USA.

Loeffler, et al., Targeting Tumor-Associate Fibroblasts Improves Cancer Chemotherapy by Increasing Intratumoral Drug Uptake, The Journal of Clinical Investigation, vol. 116, No. 7, Jul. 2006, pp. 1955-1962, Germany.

Santos, et al., Targeting Fibroblast Activation Protein Inhibits Tumor Stromagenesis and Growth in Mice, The Journal of Clinical Investigation, vol. 119, No. 12, Dec. 2009, pp. 3613-3625, USA.

* cited by examiner

FAP INHIBITORS

FIELD OF THE INVENTION

The present invention relates to novel inhibitors having high selectivity and specificity for FAP (fibroblast activation protein). Said inhibitors are useful as a human and/or veterinary medicine, in particular for the treatment and/or prevention of FAP-related disorders such as but not limited to proliferative disorders.

BACKGROUND TO THE INVENTION

1. Introduction

Fibroblast activation protein (FAP, FAP-alpha, seprase, alpha2 antiplasmin converting enzyme) is a Clan SC protease of the prolyl oligopeptidase subfamily S9b, occurring as a cell surface homodimer. FAP has been demonstrated to possess both dipeptidyl peptidase and endopeptidase activity, catalyzed by the same active center. Its expression is associated with activated stromal fibroblasts and pericytes of over 90% of human epithelial tumors examined and with normal or excessive wound healing, e.g. in tissue remodeling sites or during chronic inflammation. The enzyme is generally not expressed in normal adult tissues and in nonmalignant tumors.[1] Several studies have tried to map the physiological substrate spectrum of FAP, including very recent reports that identify i.a. alpha2-antiplasmin, type I collagen and gelatin as in vitro substrates of the endopeptidase activity of FAP.[2] Analogously, Neuropeptide Y, B-type natriuretic peptide, substance P and peptide YY have been identified as in vitro substrates of the dipeptidyl peptidase activity of FAP.[3] Nonetheless, the relevance of these findings under in vivo conditions remains debatable and the unambiguous definition of FAP's physiological substrate spectrum remains untouched matter so far.

Through structure-based design studies combined with extensive synthetic and biochemical effort, we were able to establish a Structure-Activity Relationship (SAR) of N-acylated aminoacyl pyrrolidine inhibitors of fibroblast activation protein. This has led to the discovery of a novel scaffold type that has the potential to deliver inhibitors of FAP that combine low nanomolar activity with unprecedented selectivity toward related Clan SC proteases (dipeptidyl peptidases IV, II, 8/9 and the endopeptidase prolyl oligopeptidase (PREP, PO). When compared to most other classes of reported inhibitors of FAP, inhibitors belonging to the scaffold type described here have remarkable stability both in aqueous solution and in human plasma and retain activity and selectivity for FAP within the latter media. For example, WO2007085895, WO2007005991, WO2010083570, WO2006125227 and WO0238590 all disclose FAP inhibitors having a general structure closely relating to the compounds of the present invention. However, none of them actually discloses compounds wherein

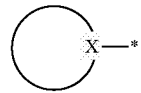

as defined in the present invention, is a 5 to 10-membered N-containing aromatic or non-aromatic mono- or bicyclic heterocycle, wherein there are exactly 2 ring atoms between the N atom and X. As further detailed herein below, in particular said feature is relevant for providing the compounds of the present invention with the FAP activity and selectivity as defined herein.

Based on FAP's role in (patho-)fysiology, documented extensively in literature, we reasonably foresee potential applications of our inhibitors in disease domains characterised by: (a) proliferation (including but not limited to cancer) (b) tissue remodelling and/or chronic inflammation (including but not limited to fibrotic disease, wound healing, keloid formation, osteoarthritis, rheumatoid arthritis and related disorders involving cartilage degradation) and (c) endocrinological disorders (including but not limited to disorders of glucose metabolism). The relationship of FAP with said pathological processes is described in more detail hereafter.

(a) FAP and Proliferative Diseases (Including but not Limited to Cancer).

During the last decade, numerous reports have been published that claim an important role for FAP in tumor growth and proliferation. The exact mechanism by which FAP takes part in these processes is unknown, but direct modulation of tumor growth, angiogenesis or disease progression by proteolytic processing of growth factors, cytokines, collagenase activity regulating proteins and even collagen derived proteins, is currently the subject of intensive research.

While awaiting the detailed functional characterization of the enzyme in these processes, several groups currently focus on FAP's status as a potential cancer biomarker which presence or activity in tumors could also be used for site-directed delivery of oncology drugs.[4] Equally important, FAP or its activity are being targeted by several groups as a direct way to reduce tumor growth and proliferation by means of immunotherapeutic and small molecule inhibitor approaches.[5] For the latter, a number of in vivo proof-of-concept studies are present. These all involve the dipeptide derived boronic acid talabostat (PT-100, Val-boroPro) or close analogues, and report significant activity on tumor stromagenesis and growth.[6] In addition, talabostat has been evaluated as a drug in various clinical trials up to phase II, for the treatment of, i.a. metastatic kidney cancer, chronic lymphocytary leukemia, pancreatic adenocarcinoma and non-small cell lung cancer. While talabostat in several of these trials was able to induce clinical response, questions were raised with regards to the safety profile of the compound, potentially related to its well-known lack of selectivity with respect to other Subfamily S9B proteases.[7]

(b) FAP and Diseases Involving Tissue Remodeling and/or Chronic Inflammation (Including but not Limited to Fibrotic Disease, Wound Healing, Keloid Formation, Osteoarthritis, Rheumatoid Arthritis and Related Disorders Involving Cartilage Degradation, Atherosclerotic Disease and Chron's Disease)

Multiple reports on occurrence of significantly increased FAP expression and/or activity both in physiological processes and in several clearly distinct disease domains, indicate that the enzyme might play an important role during events characterized by tissue remodeling and/or inflammation. Although the exact mechanism by which FAP is alleged to do so has to date not been clarified, the most straightforward hypothesis involves the enzyme's capability of processing collagenase activity regulating proteins and even collagen derived proteins, thereby altering the composition and structure of the extracellular matrix (ECM) of tissues. This effect could be supplemented by influences on the proteolytic processing of peptide growth factors and cytokines. Similar arguments are summoned to describe the of FAP's role in proliferative disease (vide supra).

Significant FAP expression has been confirmed for reactive fibroblasts in granulation tissue of healing wounds, on stellate cells at the tissue remodeling interface in hepatic cirrhosis, and in lung tissue in idiopathic pulmonary fibrosis.[8] For hepatic cirrhosis (the pathological state characterized by fibrosis in which FAP's involvement has been best characterized) elevated expression of FAP was observed regardless of the etiology of the disease (viral hepatitis-induced, alcohol-induced, biliary cirrhosis). This given might suggest broad applicability of FAP-targeted therapy, e.g. using small molecule inhibitors, in disease area's involving fibrotic liver degeneration.[9]

FAP expression was found to be significantly increased on keloid fibroblasts compared to normal skin fibroblasts and inhibition of FAP activity with the albeit unselective (with respect to phylogenetically related dipeptidyl peptidases) irreversible inhibitor Gly-Pro$^{(P)}$(OPh)$_2$ was found to lead to a decrease in invasiveness.[10]

FAP expression and activity was also shown to be associated with rheumatoid arthritis and osteoarthritis: FAP-activity on the surface of chondrocytes and elevated expression and activity in cartilage affected by osteoarthritis were demonstrated. FAP was also found to be present in synovial tissue of affected joints, and elevated expression is detected in the murine collagen induced arthritis model. An additional pathway by which FAP could be operating in the pathogenesis and progression of arthritis, has been proposed to imply proteolytic cleavage of alpha2-antiplasmin, ultimately leading to fibrin deposition in the joint. Notably, in a Phase 1 clinical dosing study with a humanized anti-FAP antibody (sibrotuzumab) for advanced and metastatic cancer, the antibody in three patients not only localized to tumors, but also to the knees and shoulders. This observation has been connected to early-stage arthritis, offering initial support for the in vivo validation of FAP as a target for arthritis and related diseases.[11]

Recently, significantly increased expression of FAP was reported for human Type IV-Type V aortic atheromata, compared to type III atheromata and healthy aortae. Additionally, thin-cap human coronary atheromata were found to contain more FAP than thick-cap lesions. The enzyme's occurrence was found to be concentrated on smooth muscle and endothelial cells, and it could not be detected on macrophages. Nonetheless, macrophage burden did correlate with total FAP expression in the plaques. Furthermore, in vitro zymography revealed that FAP-mediated collagenase activity was neutralized by an antibody directed to the enzyme's catalytic domain both in human atherosclerotic smooth muscle cells and in fibrous caps of atherosclerotic plaques.[2b]

In a very recent publication, FAP was found to be overexpressed in enteric strictures of patients with Chron's disease (CD) and the protein was observed to be upregulated on strictured CD myofibroblasts by profibrogenic stimuli, leading the authors of this study to propose FAP as a potential target for the treatment of fibrostenosing CD.[12]

In general, no in vivo or clinical results (apart from the mentioned) have so far been disclosed dealing with the application of FAP-targeting small molecules or immunotherapeutic strategies in disease domains mentioned under this part. Nonetheless, mounting in vitro evidence from literature can certainly be considered compelling to initiate such investigations.

(c) FAP and Diseases Involving Endocrinological Disorder (Including but not Limited to Disorders of Glucose Metabolism) and Diseases Involving Blood Clotting Disorders.

A recent patent application by Gorrell et al. claims the utility of FAP inhibitors in the prevention and treatment of metabolic abnormalities characterized by abnormal glucose metabolism, including diabetes mellitus and new onset diabetes. This claim is however not otherwise documented in the literature.[13]

Finally, blocking the activity of the soluble form of FAP (alpha2-antiplasmin cleaving enzyme, APCE) occurring in plasma, using small molecule inhibitors was found to cause enhanced fibrinolysis and to lead to a decrease of plasminogen activator induced clot lysis time. This observation led the authors to state that APCE-inhibition might constitute a novel approach in thrombolytic therapy without significant risk of bleeding.[14]

2. Inhibitor Design

The prime aim underlying our effort to establish detailed SAR data for N-acylated aminoacyl pyrrolidine inhibitors of FAP, was to identify compounds with significantly improved (a) chemical stability and (b) selectivity characteristics when compared to known FAP inhibitors, while retaining high affinity for the target enzyme.

(a) Limited chemical stability due to intramolecular cyclisation is a well known problem of several currently available highly potent dipeptide derived boronic acids (e.g. Val-boro-Pro). This property, caused by the combined presence of a nucleophilic amino terminus and an electrophilic boronic acid, puts constraints e.g. on the applicability of this compound and its analogues at physiological pH both in vitro and in vivo.[15]

(b) Selectivity with respect to related S9b proteases (DPP IV, DPP8/9, DPP II, PREP) is a potential point of concern for all FAP inhibitors. Due to the high degree of phylogenetic relationship between the S9b proteases, pharmacophores of their inhibitors generally display substantial overlap. This problem is well documented for a number of described FAP inhibitors, including the well known ValboroPro. Noteworthy however, for most reported FAP inhibitors incomplete and in some cases even no selectivity data have been reported, rendering existing knowledge as a starting point for selective FAP inhibitor discovery inadequate. Nonetheless, taking into account the importance of inhibitor selectivity in the framework of potential compound toxicity and off-target effects, we deemed the preparation of selective compounds an important goal of our endeavours.[1]

With the number of reported FAP-inhibitors being small and most of them belonging to the class of boronic acids, we initially decided to focus on compounds that contain a carbonitrile warhead in place of the boronic acid, but conserve an overall dipeptide derived architecture. The latter is a hallmark of most chemotypes of published Subfamily S9B inhibitors. The carbonitrile function itself is also a popular affinity-enhancing moiety in reported series of inhibitors of DPP IV, DPP8, DPP9 and PREP. Compared to other warheads that are used in serine protease inhibitor design (e.g. —B(OH)$_2$, —CHO, chloromethylketones, ketoamides, . . . ) the relatively mildly electrophilic carbonitrile could account for making the inhibitor more selective in vivo, a hypothesis that has been raised in literature earlier.[1] In addition, the projected structures' overall architecture does in principle not impose fundamental limitations with respect to in vivo use, as e.g. illustrated by the EMA-approved vildagliptin and the FDA approved saxagliptin, both inhibitors of DPP IV. Three other publications are known to us that also contain carbonitrile-based inhibitors of FAP, all of them including incomplete FAP affinity and selectivity data or, in one case, even no affinity at all.[16]

Using the boundary assumptions described above, we decided to start an in depth investigation of the Structure-Activity Relationship (SAR) of N-acylaminoacyl(2-cyanopyrrolidines) as inhibitors of FAP and their selectivity toward dipeptidyl peptidases and PREP. Three main structural fragments within this structure were marked for investigation and elaboration of the SAR:

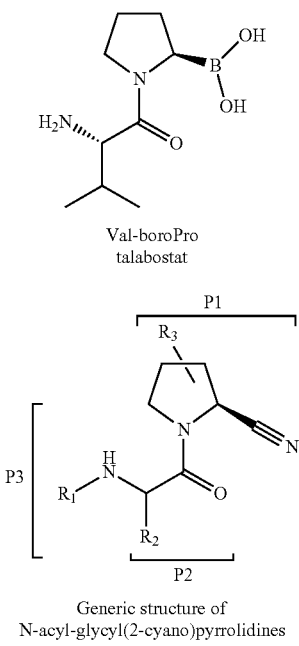

Val-boroPro
talabostat

Generic structure of
N-acyl-glycyl(2-cyano)pyrrolidines $R_1$ = alkanoyl-, aryloyl-, arylalkanoyl, arylsulfonyl, ...
$R_2$ = alkyl-, aryl-, arylalkyl, ...
$R_3$ = methyl-, ethyl-, methylideen-, fluoro-, difluoro-, ...

(a) the P3 Moiety:

By attaching this moiety (via an acyl linkage) to the aminoacyl(2-cyanopyrrolidine) backbone of the inhibitor, we wanted to make the P2 residue non-basic and non-nucleophilic, thus increasing the likeliness of inhibitor selectivity and higher stability with respect to the S9b dipeptidyl peptidases. Some literature evidence existed for peptide derived boronic acid inhibitors that this approach might be viable, although no systematic studies in this direction have been carried out. In addition, a substantial number of these literature FAP inhibitors have been reported with only limited or even without selectivity data for the related dipeptidyl peptidases. Additionally, while one might anticipate affinity toward dipeptidyl peptidases to be smaller, blocking the amino terminus does substantially increase the risk of selectivity problems with respect to the endopeptidase PREP. Again, very limited literature information was present dealing with FAP to PREP selectivity of inhibitors with an acylated P2 amine function.[1]

(b) the P2 Moiety:

while several acylated glycyl(2-borono)pyrrolidines have been reported in literature, almost no data exist on the influence of other amino acid residues at the P2 position in acylated compounds. At the outset of our activities, substrate kinetics studies nonetheless indicated a rather strict preference of FAP for a P2-glycine residue in substrates containing an acylated P2 amino function. This given is in sharp contrast with a series of dipeptide-derived substrates and/or inhibitors (e.g. ValboroPro) with a free amino terminus, where the number of tolerated P2 residues is known to be much larger.

(c) The P1 Moiety:

We decided to investigate the influence on activity and selectivity of substituting the pyrrolidine ring in compounds with structure 1. To this end, we selected a number of different functional groups with different bulk size and electronic effects.

In addition, we expected the obtained SAR-information poised to be applicable to analogous inhibitor types containing specific other warhead types or even no warhead, a hypothesis that we later on showed to be correct.

We have now surprisingly found that FAP-inhibitors of formula I exhibit good chemical stability and high selectivity for FAP, rendering them very suitable for the preparation of a medicine for the treatment of various FAP-related disorders. In addition, our invention has the potential to deliver compounds with high solubility and low Log D-values, a feature that is far from evident for dipeptide-derived compounds lacking a basic amino terminus and that is accounted for by the presence of heteroatoms introduced at specific positions of the P3 substituent.

SUMMARY OF THE INVENTION

In a first aspect, the present invention provides a compound of Formula I or a stereoisomer, tautomer, racemic, metabolite, pro- or predrug, salt, hydrate, or solvate thereof,

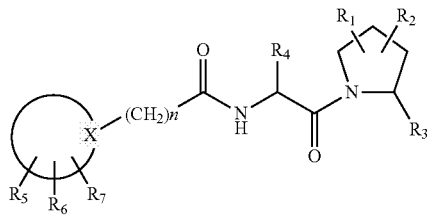

Wherein
$R_1$ and $R_2$ are each independently selected from the group comprising —H, OH, -halo, $C_{1-6}$alkyl, —O—$C_{1-6}$alkyl, S—$C_{1-6}$alkyl;
$R_3$ is selected from the group comprising —H, —CN, —B(OH)$_2$, —C(O)alkyl, —C(O)aryl-, —C≡C—C(O)aryl, —C≡C—S(O)$_2$aryl, —CO$_2$H, —SO$_3$H, —SO$_2$NH$_2$, —PO$_3$H$_2$, and 5-tetrazolyl;
$R_4$ is selected from the group comprising —H, —$C_{1-6}$alkyl, —O—$C_{1-6}$alkyl, —S—$C_{1-6}$alkyl, —Ar$_1$, and —$C_{1-6}$ aralkyl; each of said —$C_{1-6}$alkyl being optionally substituted with from 1 to 3 substituents selected from —OH, -halo
$R_5$, $R_6$ and $R_7$ are each independently selected from the group comprising —H, —OH, -oxo, -halo, —$C_{1-6}$alkyl, —O—$C_{1-6}$alkyl, —S—$C_{1-6}$alkyl, —NR$_8$R$_9$, —OR$_{12}$ -Het$_2$ and —Ar$_2$; each of said $C_{1-6}$alkyl being optionally substituted with from 1 to 3 substituents selected from —OH, -halo
$R_8$, $R_9$ and $R_{12}$ are each independently selected from the group comprising —H, —OH, -halo, —$C_{1-6}$alkyl, —O—$C_{1-6}$alkyl, —S—$C_{1-6}$alkyl, and —Ar$_3$
$R_{10}$, $R_{11}$, $R_{13}$ and $R_{14}$ are each independently selected from the group comprising —H, —OH, -halo, —$C_{1-6}$alkyl, —O—$C_{1-6}$alkyl, and —S—$C_{1-6}$alkyl;
Ar$_1$, Ar$_2$ and Ar$_3$ are each independently a 5- or 6-membered aromatic monocycle optionally comprising 1 or 2 heteroatoms selected from O, N and S; each of said Ar$_1$, Ar$_2$ and Ar$_3$ being optionally and independently substituted with from 1 to 3 substituents selected from —NR$_{10}$R$_{11}$, —C$_{1-6}$alkyl, —O—C$_{1-6}$alkyl, —S—C$_{1-6}$alkyl;

Het$_2$ is a 5- or 6-membered non-aromatic monocycle optionally comprising 1 or 2 heteroatoms selected from O, N and S; said Het$_2$ being optionally substituted with from 1 to 3 substituents selected from —NR$_{13}$R$_{14}$, —C$_{1-6}$alkyl, —O—C$_{1-6}$alkyl, —S—C$_{1-6}$alkyl;

n is 0, 1, 2, or 3

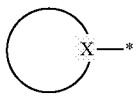

represents a 5 to 10-membered N-containing aromatic or non-aromatic mono- or bicyclic heterocycle, wherein there are exactly 2 ring atoms between the N atom and X; said heterocycle optionally further comprising 1, 2 or 3 heteroatoms selected from O, N and S; and X represents a C atom In a preferred embodiment, the present invention provides a compound according to formula I, wherein R$_1$ and R$_2$ are each independently selected from the group comprising —H, and -halo;

R$_3$ is —CN, or —B(OH)$_2$

R$_4$ is selected from the group comprising —H or —C$_{1-6}$alkyl; each of said —C$_{1-6}$alkyl being optionally substituted with from 1 to 3 substituents selected from —OH;

R$_5$, R$_6$ and R$_7$ are each independently selected from the group comprising —H, —OH, -oxo, -halo, —C$_{1-6}$alkyl, —O—C$_{1-6}$alkyl, Ar$_2$ and —NR$_8$R$_9$; each of said C$_{1-6}$alkyl being optionally substituted with from 1 to 3 substituents selected from —OH, -halo;

R$_8$ and R$_9$ are each independently selected from the group comprising —H and —Ar$_3$ Ar$_2$ and Ar$_3$ are each independently -phenyl optionally substituted with from 1 to 3-O—C$_{1-6}$alkyl;

n is 0 or 1

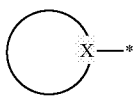

represents a 5 to 10-membered N-containing aromatic or non-aromatic mono- or bicyclic heterocycle, wherein there are exactly 2 ring atoms between the N atom and X; said heterocycle optionally further comprising 1, 2 or 3 heteroatoms selected from O, N and S; and X represents a C atom In yet another preferred embodiment, the present invention provides a compound according to formula I, wherein R$_1$ and R$_2$ are each independently selected from the group comprising —H, and —F;

R$_3$ is —CN, and —B(OH)$_2$

R$_4$ is —H;

R$_5$, R$_6$ and R$_7$ are each independently selected from the group comprising —H, -oxo, -halo, —C$_{1-6}$alkyl, and —O—CF$_3$;

n is 0;

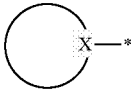

represents a 5 to 10-membered N-containing aromatic or non-aromatic mono- or bicyclic heterocycle, wherein there are exactly 2 ring atoms between the N atom and X; said heterocycle optionally further comprising 1, 2 or 3 heteroatoms selected from O, N and S; and X represents a C atom The current invention further provides a compound of Formula II or a stereoisomer, tautomer, racemic, metabolite, pro- or predrug, salt, hydrate, or solvate thereof,

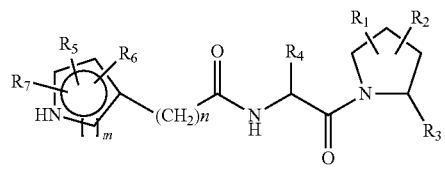

II wherein

R$_1$ and R$_2$ are each independently selected from the group comprising —H, OH, -halo, C$_{1-6}$alkyl, —O—C$_{1-6}$alkyl, S—C$_{1-6}$alkyl;

R$_3$ is selected from the group comprising —H, —CN, —B(OH)$_2$, —C(O)alkyl, —C(O)aryl-, —C=C—C(O)aryl, —C=C—S(O)$_2$aryl, —CO$_2$H, —SO$_3$H, —SO$_2$NH$_2$, —PO$_3$H$_2$, and 5-tetrazolyl R$_4$ is selected from the group comprising —H, —C$_{1-6}$alkyl, —O—C$_{1-6}$alkyl, —S—C$_{1-6}$alkyl, —Ar$_1$, and —C$_{1-6}$aralkyl; each of said —C$_{1-6}$alkyl being optionally substituted with from 1 to 3 substituents selected from —OH, -halo R$_5$, R$_6$ and R$_7$ are each independently selected from the group comprising —H, —OH, -oxo, -halo, —C$_{1-6}$alkyl, —O—C$_{1-6}$alkyl, —S—C$_{1-6}$alkyl, —NR$_8$R$_9$, and —Ar$_2$; each of said C$_{1-6}$alkyl being optionally substituted with from 1 to 3 substituents selected from —OH, -halo R$_8$ and R$_9$, R$_{10}$ and R$_{11}$ are each independently selected from the group comprising —H, —OH, -halo, —C$_{1-6}$alkyl, —O—C$_{1-6}$alkyl, and —S—C$_{1-6}$alkyl;

R$_{10}$ and R$_{11}$ are each independently selected from the group comprising —H, —OH, -halo, —C$_{1-6}$alkyl, —O—C$_{1-6}$alkyl, —S—C$_{1-6}$alkyl, and —Ar$_3$;

Ar$_1$, Ar$_2$ and Ar$_3$ are each independently a 5- or 6-membered aromatic monocycle optionally comprising 1 or 2 heteroatoms selected from O, N and S; each of said Ar$_1$, and Ar$_2$ being optionally and independently substituted with from 1 to 3 substituents selected from —NR$_{10}$R$_{11}$, —C$_{1-6}$alkyl, —O—C$_{1-6}$alkyl, —S—C$_{1-6}$alkyl;

n is 0, 1, 2, or 3 m is 1 or 2

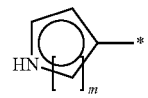

represents a 5 to 6-membered N-containing aromatic or non-aromatic monocyclic heterocycle optionally further comprising 1 or 2 heteroatoms selected from O, N and S.

In a preferred embodiment, the current invention provides a compound according to formula II, wherein $R_1$ and $R_2$ are each independently selected from the group comprising —H, OH, -halo, $C_{1-6}$alkyl, —O—$C_{1-6}$alkyl, S—$C_{1-6}$alkyl;

$R_3$ is selected from the group comprising —H, —CN, and —B(OH)$_2$ $R_4$ is —H;

$R_5$, $R_6$ and $R_7$ are each independently selected from the group comprising —H, —OH, -oxo, -halo, —$C_{1-6}$alkyl, —O—$C_{1-6}$alkyl, —S—$C_{1-6}$alkyl, —NR$_8$R$_9$, and —Ar$_2$; each of said $C_{1-6}$alkyl being optionally substituted with from 1 to 3 substituents selected from —OH, -halo $R_8$, $R_9$, $R_{10}$ and $R_{11}$ are each independently selected from the group comprising —H, —OH, -halo, —$C_{1-6}$alkyl, —O—$C_{1-6}$alkyl, and —S—$C_{1-6}$alkyl;

Ar$_2$ is a 5- or 6-membered aromatic monocycle optionally comprising 1 or 2 heteroatoms selected from O, N and S; Ar$_2$ being optionally and independently substituted with from 1 to 3 substituents selected from —NR$_{10}$R$_{11}$, —$C_{1-6}$alkyl, —O—$C_{1-6}$alkyl, —S—$C_{1-6}$alkyl;

n is 0, 1, 2, or 3 m is 1 or 2

is a 5- or 6-membered aromatic or non-aromatic monocyclic heterocycle optionally further comprising 1 or 2 heteroatoms selected from O, N and S; selected from the list comprising

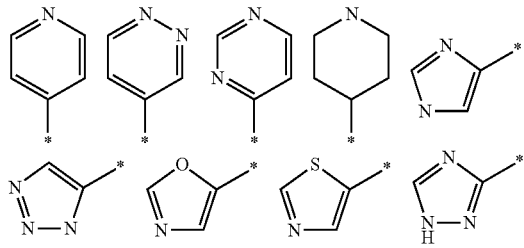

In said embodiment, preferably, $R_5$ and $R_6$ are each —H; $R_7$ is selected from the group comprising —H, —OH, -oxo, -halo, —$C_{1-6}$alkyl, —O—$C_{1-6}$alkyl, —S—$C_{1-6}$alkyl, —NR$_8$R$_9$, and —Ar$_2$; each of said $C_{1-6}$alkyl being optionally substituted with from 1 to 3 substituents selected from —OH, -halo; and $R_7$ is attached to position 2 or 3, in particular position 2, as represented in

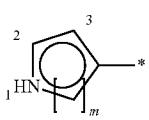

In yet a further embodiment, the present invention provides a compound of formula IIIa, IIIb or IIIc or a stereoisomer, tautomer, racemic, metabolite, pro- or predrug, salt, hydrate, or solvate thereof,

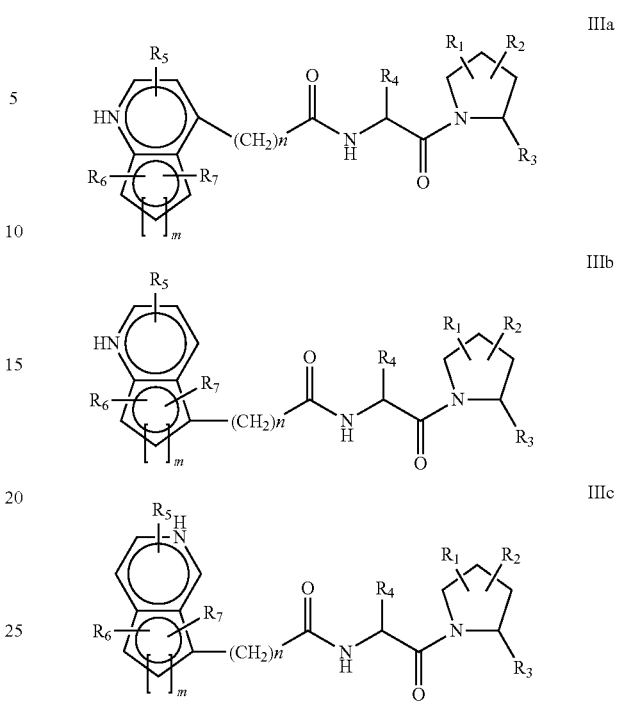

wherein $R_1$ and $R_2$ are each independently selected from the group comprising —H, OH, -halo, $C_{1-6}$alkyl, —O—$C_{1-6}$alkyl, S—$C_{1-6}$alkyl;

$R_3$ is selected from the group comprising —H, —CN, —B(OH)$_2$, —C(O)alkyl, —C(O)aryl-, —C≡C—C(O)aryl, —C≡C—S(O)$_2$aryl, —CO$_2$H, —SO$_3$H, —SO$_2$NH$_2$, —PO$_3$H$_2$, and 5-tetrazolyl $R_4$ is selected from the group comprising —H, —$C_{1-6}$alkyl, —O—$C_{1-6}$alkyl, —S—$C_{1-6}$alkyl, —Ar$_1$, and —$C_{1-6}$aralkyl; each of said —$C_{1-6}$alkyl being optionally substituted with from 1 to 3 substituents selected from —OH, -halo;

$R_5$, $R_6$ and $R_7$ are each independently selected from the group comprising —H, —OH, -oxo, -halo, —$C_{1-6}$alkyl, —O—$C_{1-6}$alkyl, —S—$C_{1-6}$alkyl, —NR$_8$R$_9$, and —Ar$_2$; each of said $C_{1-6}$alkyl being optionally substituted with from 1 to 3 substituents selected from —OH, -halo $R_8$ and $R_9$, are each independently selected from the group comprising —H, —OH, -halo, —$C_{1-6}$alkyl, —O—$C_{1-6}$alkyl, —S—$C_{1-6}$alkyl, and —Ar$_3$ $R_{10}$ and $R_{11}$ are each independently selected from the group comprising —H, —OH, -halo, —$C_{1-6}$alkyl, —O—$C_{1-6}$alkyl, and —S—$C_{1-6}$alkyl;

Ar$_1$, Ar$_2$ and Ar$_3$ are each independently a 5- or 6-membered aromatic monocycle optionally comprising 1 or 2 heteroatoms selected from O, N and S; each of said Ar$_1$, and Ar$_2$ being optionally and independently substituted with from 1 to 3 substituents selected from —NR$_{10}$R$_{11}$, —$C_{1-6}$alkyl, —O—$C_{1-6}$alkyl, —S—$C_{1-6}$alkyl;

n is 0, 1, 2, or 3 m is 1 or 2

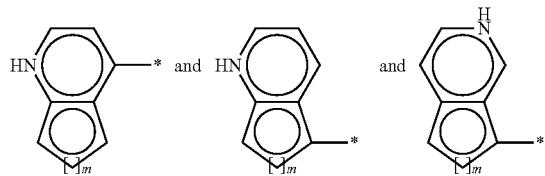

represent a 9 to 10-membered N-containing aromatic or non-aromatic bicyclic heterocycle optionally further comprising 1 or 2 heteroatoms selected from O, N and S.

In a preferred embodiment, the present invention provides a compound according to formula III, wherein $R_1$ and $R_2$ are each independently selected from the group comprising —H, OH, -halo, $C_{1-6}$alkyl, —O—$C_{1-6}$alkyl, S—$C_{1-6}$alkyl;

$R_3$ is selected from the group comprising —H, —CN, and —B(OH)$_2$;

$R_4$ is —H;

$R_5$, $R_6$ and $R_7$ are each independently selected from the group comprising —H, —OH, -oxo, -halo, —$C_{1-6}$alkyl, —O—$C_{1-6}$alkyl, —S—$C_{1-6}$alkyl, —NR$_8$R$_9$, and —Ar$_2$; each of said $C_{1-6}$alkyl being optionally substituted with from 1 to 3 substituents selected from —OH, -halo $R_8$, $R_9$, $R_{10}$ and $R_{11}$ are each independently selected from the group comprising —H, —OH, -halo, —$C_{1-6}$alkyl, —O—$C_{1-6}$alkyl, and —S—$C_{1-6}$alkyl;

$Ar_2$ is a 5- or 6-membered aromatic monocycle optionally comprising 1 or 2 heteroatoms selected from O, N and S; $Ar_2$ being optionally and independently substituted with from 1 to 3 substituents selected from —NR$_{10}$R$_{11}$, —$C_{1-6}$alkyl, —O—$C_{1-6}$alkyl, —S—$C_{1-6}$alkyl;

n is 0, 1, 2, or 3 m is 1 or 2

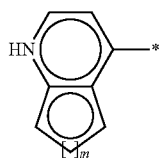

is a 9- or 10-membered aromatic or non-aromatic bicyclic heterocycle optionally further comprising 1 or 2 heteroatoms selected from O, N and S; selected from the list comprising

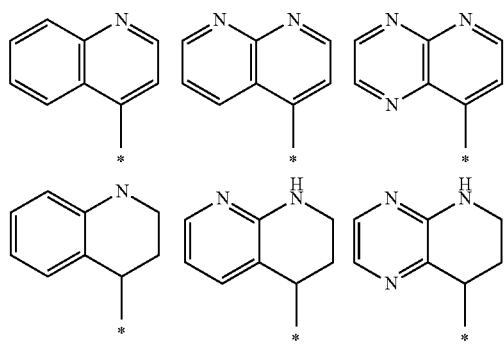

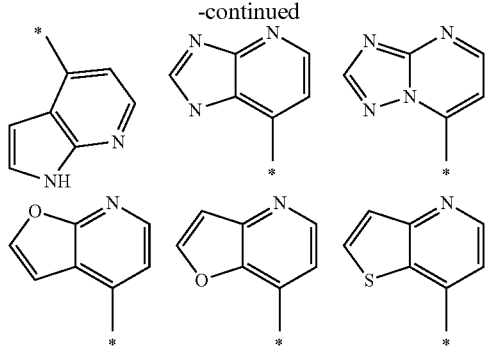

In said embodiment, $R_5$ is preferably attached to position 2 or 3, in particular position 3, as represented in

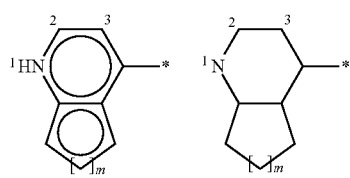

The current invention further provides a compound of formula I, II, IIIa, IIIb or IIIc as defined above, as well as pharmaceutical compositions comprising said compounds, for use as a human or veterinary medicine.

In a further aspect, the present invention provides the use of a compound as defined above, as well as pharmaceutical compositions comprising said compounds, in the manufacture of a medicament for the prevention and/or treatment of a FAP-related disorder. A non-limiting list of examples of FAP-related disorders can include proliferative diseases selected from the group comprising breast cancer, colorectal cancer, ovarian cancer, prostate cancer, pancreatic cancer, kidney cancer, lung cancer, melanoma, fibrosarcoma, bone and connective tissue sarcomas, renal cell carcinoma, giant cell carcinoma, squamous cell carcinoma, and adenocarcinoma. In addition, the list of FAP-related disorders that are envisaged here, includes diseases characterised by tissue remodeling and/or chronic inflammation. These include but are not limited to fibrotic disease, wound healing, keloid formation, osteoarthritis, rheumatoid arthritis and related disorders involving cartilage degradation, atherosclerotic disease and Chron's disease. Furthermore, FAP related disorders involving endocrinological dysfunction (including but not limited to disorders of glucose metabolism) and diseases involving blood clotting disorders are part of this list.

It further provides the use of a compound as defined above, as well as pharmaceutical compositions comprising said compounds for inhibiting the activity of FAP.

In a further aspect, the present invention provides the use of a compound as defined above, as well as pharmaceutical compositions comprising said compounds, for the prevention and/or treatment of a FAP-related disorder. A non-limiting list of examples of FAP-related disorders can include proliferative diseases selected from the group comprising breast cancer, colorectal cancer, ovarian cancer, prostate cancer, pancreatic cancer, kidney cancer, lung cancer, melanoma, fibrosarcoma, bone and connective tissue sarcomas, renal cell carcinoma, giant cell carcinoma, squamous cell carcinoma, and adenocarcinoma. In addition, the list of FAP-related disorders that are envisaged here, includes diseases characterised by tissue remodeling and/or chronic inflammation. These include but are not limited to fibrotic disease, wound healing, keloid formation, osteoarthritis, rheumatoid arthritis and related disorders involving cartilage degradation, atherosclerotic disease and Chron's disease. Furthermore, FAP related disorders involving endocrinological dysfunction (including but not limited to disorders of glucose metabolism) and diseases involving blood clotting disorders are part of this list.

In a final aspect, the present invention provides a method for the prevention and/or treatment of a FAP-related disorder. A non-limiting list of examples of FAP-related disorders can include proliferative diseases selected from the group comprising breast cancer, colorectal cancer, ovarian cancer, prostate cancer, pancreatic cancer, kidney cancer, lung cancer, melanoma, fibrosarcoma, bone and connective tissue sarcomas, renal cell carcinoma, giant cell carcinoma, squamous cell carcinoma, and adenocarcinoma. In addition, the list of FAP-related disorders that are envisaged here, includes diseases characterised by tissue remodeling and/or chronic inflammation. These include but are not limited to fibrotic disease, wound healing, keloid formation, osteoarthritis, rheumatoid arthritis and related disorders involving cartilage degradation, atherosclerotic disease and Chron's disease. Furthermore, FAP related disorders involving endocrinological dysfunction (including but not limited to disorders of glucose metabolism) and diseases involving blood clotting disorders are part of this list.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Results of our SAR investigations that were directly instructive for the invention will be summarized here along with the corresponding modification types mentioned in the former part, that were subject of this SAR study.

(a) The P3 Moiety:

An initial amount of SAR data for the P3 position was obtained by preparing and evaluating a series of compounds with a common Gly-(2-cyano)pyrrolidine backbone, carrying different P3 acyl- or sulfonamide type substituents at the free amino terminus. From this first series of compounds, the following inhibitors deserve special mentioning (Table 1):

Inhibitors 3, 4 and 5 shared substantial FAP affinity ($IC_{50} < 5$ μM), decoupled from PREP binding potential. The common structural feature that can be held accountable for this profile, is an (azaheterocyclyl)ac(et-)yl group as the $R_1$ scaffold substituent. Evidently, both the scope of this assumption and the possibility to improve FAP affinity were the subject of further investigation (vide infra).

Compound 6, containing a 1-naphthoyl substituent, was found to have equally good FAP inhibitory activity compared to compounds 3, 4 and 5, however it was far less selective towards FAP, compared to the other inhibitors of the first series. Our selection of the 1-naphthoyl residue was based on a patent by Bachovchin et al., in which the activity of N-(1-naphthoyl)-substituted Gly-boroPro was claimed to possess superior FAP-affinity relative to the N-benzoyl substituted congener, an observation we also found to hold for the corresponding nitriles. In addition, compound 6 was also reported in a recent publication by Tsai et al., with comparable FAP potency, but not including PREP assay data.[14]

TABLE 1

Affinity/selectivity data for selected N-acyl-glycyl-(2-cyano)pyrrolidines.[a]

| Cpd | $R_1$ | FAP | PREP | DPPII | DPPIV | DPP9 |
|---|---|---|---|---|---|---|
| 3 | (F-C6H4-)2-N-piperazinyl-CH2-C(O)- | 2.7 ± 0.1 | >10 | >100 | >100 | >100 |
| 4 | 3,4-difluorophenyl-triazolyl-CH2-C(O)- | 1.3 ± 0.1 | >50 | >100 | >100 | 69 ± 2 |

TABLE 1-continued

Affinity/selectivity data for selected N-acyl-glycyl-(2-cyano)pyrrolidines.[a]

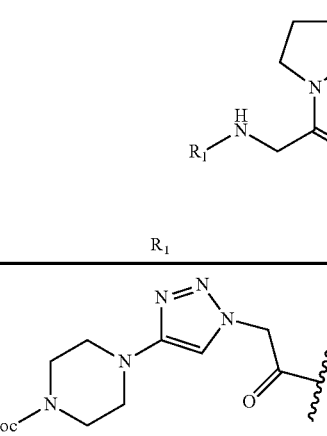

| Cpd | R$_1$ | FAP | PREP | DPPII | DPPIV | DPP9 |
|---|---|---|---|---|---|---|
| | | IC$_{50}$ (μm) | | | | |
| 5 | 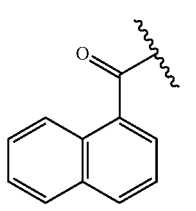 [SMILES: *C(=O)c1cccc2ccccc12] | 2.7 ± 0.1 | >100 | >100 | >100 | >100 |
| 6 | 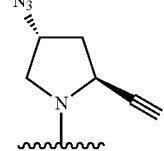 | 0.67 ± 0.04 | 3.3 ± 0.2 | >100 | >100 | >10 |

[a]DPP9 potencies reported can reasonably be expected to be indicative for inhibitor affinities toward the highly homologous DPP8

These findings were used as the starting point of extended research, aiming at the identification of optimised P3 residues with the potential to yield FAP inhibitors with maximal activity and selectivity. This was supported by a modelling study in which potential interactions of the 1-naphthyl and aza-heteroaryl residues with the active sites of FAP, PREP and the S9b dipeptidyl peptidases were investigated together with the potential effect of modification of the aryl rings (e.g. substitution, introduction of hetero-atoms). Combining these modelling data with our experimental findings for i.a. compounds 3-6, led to the proposal of a general P3 moiety structure that has the combined potential to deliver highly active and selective inhibitors of FAP.

b) The P1 Moiety:

A set of sterically and electronically diverse substituent types was chemically introduced at the pyrrolidine ring. Summarizing, available space in the part of FAP's active center accommodating the P1 pyrrolidine ring turned out to be very limited. Inhibitors 8-10, having a 4-fluoro- or 4,4-difluoro-substituent, were the only compounds found to outperform FAP-potency of their non-substitued analogues. (Table 2) No significant difference could be observed between the mono- and difluorinated compounds. With regards to the FAP/PREP selectivity issue, available space in PREP's S1 pocket seems even more limited than for FAP: only in the case of the fluorinated compounds, introduction of a 4-substituent does not completely delete enzyme affinity. Taking into account its positive effect on FAP-inhibitory activity, (di-)fluorination of the 4-position of the pyrrolidine ring could be regarded upon as a viable strategy to improve FAP-selectivity of promising inhibitors.

TABLE 2

Affinity/selectivity data for selected N-acyl-glycyl-(2-cyano)pyrrolidines.[a]

| Cpd | P1 | R$_1$ | FAP | PREP | DPPII | DPPIV | DPP9* |
|---|---|---|---|---|---|---|---|
| | | | IC$_{50}$ (μm) | | | | |
| 7 | N$_3$ | 1-naphthoyl- | >100 | >100 | >100 | >100 | >10 |

TABLE 2-continued

Affinity/selectivity data for selected N-acyl-glycyl-(2-cyano)pyrrolidines.[a]

| Cpd | P1 | $R_1$ | IC$_{50}$ (µm) FAP | PREP | DPPII | DPPIV | DPP9* |
|---|---|---|---|---|---|---|---|
| 8 | (structure) | 1-naphthoyl- | 0.126 ± 0.007 | 1.1 ± 0.2 | >100 | >100 | >10 |
| 9 | (structure) | benzoyl- | 0.85 ± 0.07 | >10 | >100 | >100 | >10 |
| 10 | (structure) | 1-naphthoyl- | 0.110 ± 0.007 | 4.84 ± 0.4 | >100 | >100 | >10 |

[a]DPP9 potencies reported can reasonably be expected to be indicative for inhibitor affinities toward the highly homologous DPP8

After thorough examination and evaluation of both the experimental and modeling data we generated, we were able to inventively design a novel scaffold type according to formula I that has the potential to deliver stable FAP inhibitors that possess low nanomolar affinities for the target enzyme and that have very high selectivity indices with respect to the dipeptidyl peptidases and PREP. In addition, we were able to experimentally confirm these compounds' excellent potential with regards to FAP affinity, selectivity and stability, in a biologically relevant matrix (plasma).

Essential to both affinity and selectivity for FAP in this scaffold type is the presence of at least one nitrogen heteroatom that is part of a cyclic system in P3 of these compounds. Equally essential for both parameters is the relative 1,4-positioning of (1) the N-atom and (2) the fragment that links the P3 cyclic framework to the P2 amino function. All of these aspects of the invention will be demonstrated using the enzymatic evaluation results both of compounds that correspond and of compounds that do not correspond to the proposed scaffold type. To the best of our knowledge this finding is unprecedented in literature.

Therefore, in a first aspect the present invention provides compounds of Formula I, including a stereoisomer, tautomer, racemic, metabolite, pro- or predrug, salt, hydrate, or solvate thereof.

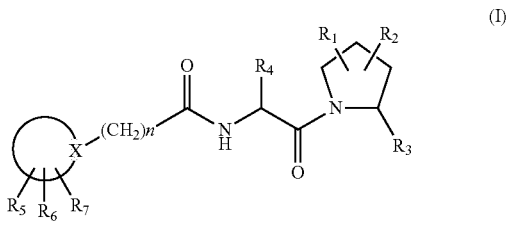

(I)

Wherein $R_1$ and $R_2$ are each independently selected from the group comprising —H, OH, -halo, $C_{1-6}$alkyl, —O—$C_{1-6}$alkyl, —S—$C_{1-6}$alkyl;

$R_3$ is selected from the group comprising —H, —CN, —B(OH)$_2$, —C(O)alkyl, —C(O)aryl-, —C≡C—C(O)aryl, —C≡C—S(O)$_2$aryl, —CO$_2$H, —SO$_3$H, —SO$_2$NH$_2$, —PO$_3$H$_2$, and 5-tetrazolyl;

$R_4$ is selected from the group comprising —H, —$C_{1-6}$alkyl, —O—$C_{1-6}$alkyl, —S—$C_{1-6}$alkyl, —Ar$_1$, and —$C_{1-6}$ aralkyl; each of said —$C_{1-6}$alkyl being optionally substituted with from 1 to 3 substituents selected from —OH, -halo $R_5$, $R_6$ and $R_7$ are each independently selected from the group comprising —H, —OH, -oxo, -halo, —$C_{1-6}$alkyl, —O—$C_{1-6}$alkyl, —S—$C_{1-6}$alkyl, —NR$_8$R$_9$, —OR$_{12}$ -Het$_2$ and —Ar$_2$; each of said $C_{1-6}$alkyl being optionally substituted with from 1 to 3 substituents selected from —OH, -halo $R_8$, $R_9$ and $R_{12}$ are each independently selected from the group comprising —H, —OH, -halo, —$C_{1-6}$alkyl, —O—$C_{1-6}$alkyl, —S—$C_{1-6}$alkyl, and —Ar$_3$ $R_{10}$, $R_{11}$, $R_{13}$ and $R_{14}$ are each independently selected from the group comprising —H, —OH, -halo, —$C_{1-6}$alkyl, —O—$C_{1-6}$alkyl, and —S—$C_{1-6}$alkyl;

Ar$_1$, Ar$_2$ and Ar$_3$ are each independently a 5- or 6-membered aromatic monocycle optionally comprising 1 or 2 heteroatoms selected from O, N and S; each of said Ar$_1$, Ar$_2$ and Ar$_3$ being optionally and independently substituted with from 1 to 3 substituents selected from —NR$_{10}$R$_{11}$, —$C_{1-6}$alkyl, —O—$C_{1-6}$alkyl, —S—$C_{1-6}$alkyl;

Het$_2$ is a 5- or 6-membered non-aromatic monocycle optionally comprising 1 or 2 heteroatoms selected from O, N and S; said Het$_2$ being optionally substituted with from 1 to 3 substituents selected from —NR$_{13}$R$_{14}$, —C$_{1-6}$alkyl, —O—C$_{1-6}$alkyl, —S—C$_{1-6}$alkyl;
n is 0, 1, 2, or 3

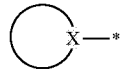

represents a 5 to 10-membered N-containing aromatic or non-aromatic mono- or bicyclic heterocycle, wherein there are exactly 2 ring atoms between the N atom and X; said heterocycle optionally further comprising 1, 2 or 3 heteroatoms selected from O, N and S; and X represents a C atom In an alternative representation, said embodiment discloses a compound of Formula X, including a stereoisomer, tautomer, racemic, metabolite, pro- or predrug, salt, hydrate, or solvate thereof

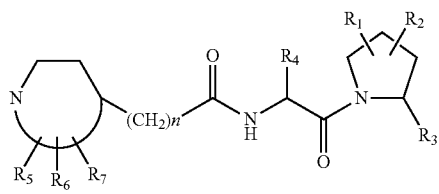
(X)

Wherein

R$_1$ and R$_2$ are each independently selected from the group comprising —H, OH, -halo, C$_{1-6}$alkyl, —O—C$_{1-6}$alkyl, S—C$_{1-6}$alkyl;

R$_3$ is selected from the group comprising —H, —CN, —B(OH)$_2$, —C(O)alkyl, —C(O)aryl-, —C≡C—C(O)aryl, —C≡C—S(O)$_2$aryl, —CO$_2$H, —SO$_3$H, —SO$_2$NH$_2$, —PO$_3$H$_2$, and 5-tetrazolyl;

R$_4$ is selected from the group comprising —H, —C$_{1-6}$alkyl, —O—C$_{1-6}$alkyl, —S—C$_{1-6}$alkyl, —Ar$_1$, and —C$_{1-6}$aralkyl; each of said —C$_{1-6}$alkyl being optionally substituted with from 1 to 3 substituents selected from —OH, -halo R$_5$, R$_6$ and R$_7$ are each independently selected from the group comprising —H, —OH, -oxo, -halo, —C$_{1-6}$alkyl, —O—C$_{1-6}$alkyl, —S—C$_{1-6}$alkyl, —NR$_8$R$_9$, —OR$_{12}$ -Het$_2$ and —Ar$_2$; each of said C$_{1-6}$alkyl being optionally substituted with from 1 to 3 substituents selected from —OH, -halo R$_8$, R$_9$ and R$_{12}$ are each independently selected from the group comprising —H, —OH, -halo, —C$_1$alkyl, —O—C$_{1-6}$alkyl, —S—C$_{1-6}$alkyl, and —Ar$_3$ R$_{10}$, R$_{11}$, R$_{13}$ and R$_{14}$ are each independently selected from the group comprising —H, —OH, -halo, —C$_{1-6}$alkyl, —O—C$_{1-6}$alkyl, and —S—C$_{1-6}$alkyl;

Ar$_1$, Ar$_2$ and Ar$_3$ are each independently a 5- or 6-membered aromatic monocycle optionally comprising 1 or 2 heteroatoms selected from O, N and S; each of said Ar$_1$, Ar$_2$ and Ar$_3$ being optionally and independently substituted with from 1 to 3 substituents selected from —NR$_{10}$R$_{11}$, —C$_{1-6}$alkyl, —O—C$_{1-6}$alkyl, —S—C$_{1-6}$alkyl;

Het$_2$ is a 5- or 6-membered non-aromatic monocycle optionally comprising 1 or 2 heteroatoms selected from O, N and S; said Het$_2$ being optionally substituted with from 1 to 3 substituents selected from —NR$_{13}$R$_{14}$, —C$_{1-6}$alkyl, —O—C$_{1-6}$alkyl, —S—C$_{1-6}$alkyl;
n is 0, 1, 2, or 3

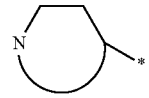 [SMILES: *CCCN]

represents a 5 to 10-membered N-containing aromatic or non-aromatic mono- or bicyclic heterocycle, wherein there are exactly 2 ring atoms between the N atom and X; said heterocycle optionally further comprising 1, 2 or 3 heteroatoms selected from O, N and S;

The present invention also provides a compound of formula (I), a stereoisomer, tautomer, racemic, metabolite, pro- or predrug, salt, hydrate, or solvate thereof

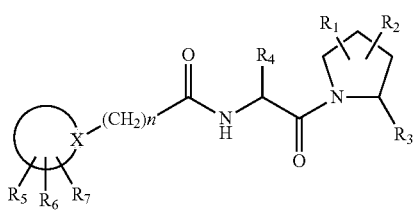
(I)

Wherein one or more of the following restrictions apply:

R$_1$ and R$_2$ are each independently selected from the group comprising —H, OH, -halo, C$_{1-6}$alkyl, —O—C$_{1-6}$alkyl, S—C$_{1-6}$alkyl;

R$_3$ is selected from the group comprising —H, —CN, —B(OH)$_2$, —C(O)alkyl, —C(O)aryl-, —C≡C—C(O)aryl, —C≡C—S(O)$_2$aryl, —CO$_2$H, —SO$_3$H, —SO$_2$NH$_2$, —PO$_3$H$_2$, and 5-tetrazolyl;

R$_4$ is selected from the group comprising —H, —C$_{1-6}$alkyl, —O—C$_{1-6}$alkyl, —S—C$_{1-6}$alkyl, —Ar$_1$, and —C$_{1-6}$aralkyl; each of said —C$_{1-6}$alkyl being optionally substituted with from 1 to 3 substituents selected from —OH, -halo R$_5$, R$_6$ and R$_7$ are each independently selected from the group comprising —H, —OH, -oxo, -halo, —C$_{1-6}$alkyl, —O—C$_{1-6}$alkyl, —S—C$_{1-6}$alkyl, —NR$_8$R$_9$, —OR$_{12}$ -Het$_2$ and —Ar$_2$; each of said C$_{1-6}$alkyl being optionally substituted with from 1 to 3 substituents selected from —OH, -halo R$_8$, R$_9$ and R$_{12}$ are each independently selected from the group comprising —H, —OH, -halo, —C$_1$alkyl, —O—C$_{1-6}$alkyl, —S—C$_{1-6}$alkyl, and —Ar$_3$ R$_{10}$, R$_{11}$, R$_{13}$ and R$_{14}$ are each independently selected from the group comprising —H, —OH, -halo, —C$_{1-6}$alkyl, —O—C$_{1-6}$alkyl, and —S—C$_{1-6}$alkyl;

Ar$_1$, Ar$_2$ and Ar$_3$ are each independently a 5- or 6-membered aromatic monocycle optionally comprising 1 or 2 heteroatoms selected from O, N and S; each of said Ar$_1$, Ar$_2$ and Ar$_3$ being optionally and independently substituted with from 1 to 3 substituents selected from —NR$_{10}$R$_{11}$, —C$_{1-6}$alkyl, —O—C$_{1-6}$alkyl, —S—C$_{1-6}$alkyl;

Het$_2$ is a 5- or 6-membered non-aromatic monocycle optionally comprising 1 or 2 heteroatoms selected from O, N and S; said Het$_2$ being optionally substituted with from 1 to 3 substituents selected from —NR$_{13}$R$_{14}$, —C$_{1-6}$alkyl, —O—C$_{1-6}$alkyl, —S—C$_{1-6}$alkyl;
n is, 1, 2, or 3

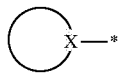

represents a 5 to 10-membered N-containing aromatic or non-aromatic mono- or bicyclic heterocycle, wherein there are exactly 2 ring atoms between the N atom and X; said heterocycle optionally further comprising 1, 2 or 3 heteroatoms selected from O, N and S; and X represents a C atom In a particular embodiment, the present invention provides a compound of formula (I), a stereoisomer, tautomer, racemic, metabolite, pro- or predrug, salt, hydrate, or solvate thereof

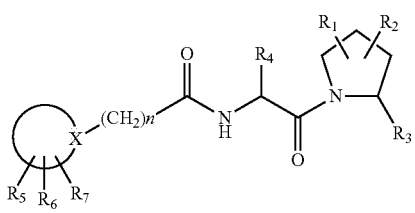

(I)

herein one or more of the following restrictions apply:

$R_1$ and $R_2$ are each independently selected from the group comprising —H, OH, -halo, $C_{1-6}$alkyl, —O—$C_{1-6}$alkyl, S—$C_{1-6}$alkyl;

$R_3$ is selected from the group comprising —H, —CN, —B(OH)$_2$, —C(O)alkyl, —C(O)aryl-, —C≡C—C(O)aryl, —C≡C—S(O)$_2$aryl, —CO$_2$H, —SO$_3$H, —SO$_2$NH$_2$, —PO$_3$H$_2$, and 5-tetrazolyl;

$R_4$ is selected from the group comprising —H, —$C_{1-6}$alkyl, —O—$C_{1-6}$alkyl, —S—$C_{1-6}$alkyl, —Ar$_1$, and —$C_{1-6}$aralkyl; each of said —$C_{1-6}$alkyl being optionally substituted with from 1 to 3 substituents selected from —OH, -halo $R_5$, $R_6$ and $R_7$ are each independently selected from the group comprising —H, —OH, -oxo, -halo, —$C_{1-6}$alkyl, —O—$C_{1-6}$alkyl, —S—$C_{1-6}$alkyl, —NR$_8$R$_9$, —OR$_{12}$ -Het$_2$ and —Ar$_2$; each of said $C_{1-6}$alkyl being optionally substituted with from 1 to 3 substituents selected from —OH, -halo $R_8$, $R_9$ and $R_{12}$ are each independently selected from the group comprising —H, —OH, -halo, —$C_{1-6}$alkyl, —O—$C_{1-6}$alkyl, —S—$C_{1-6}$alkyl, and —Ar$_3$ $R_{10}$, $R_{11}$, $R_{13}$ and $R_{14}$ are each independently selected from the group comprising —H, —OH, -halo, —$C_{1-6}$alkyl, —O—$C_{1-6}$alkyl, and —S—$C_{1-6}$alkyl;

Ar$_1$, Ar$_2$ and Ar$_3$ are each independently a 5- or 6-membered aromatic monocycle optionally comprising 1 or 2 heteroatoms selected from O, N and S; each of said Ar$_1$, Ar$_2$ and Ar$_3$ being optionally and independently substituted with from 1 to 3 substituents selected from —NR$_{10}$R$_{11}$, —$C_{1-6}$alkyl, —O—$C_{1-6}$alkyl, —S—$C_{1-6}$alkyl;

Het$_2$ is a 5- or 6-membered non-aromatic monocycle optionally comprising 1 or 2 heteroatoms selected from O, N and S; said Het$_2$ being optionally substituted with from 1 to 3 substituents selected from —NR$_{13}$R$_{14}$, —$C_{1-6}$alkyl, —O—$C_{1-6}$alkyl, —S—$C_{1-6}$alkyl;

n is 0, 1, 2, or 3

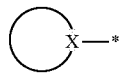

represents a 6 to 10-membered N-containing aromatic or non-aromatic mono- or bicyclic heterocycle, wherein there are exactly 2 ring atoms between the N atom and X; said heterocycle optionally further comprising 1, 2 or 3 heteroatoms selected from O, N and S; and X represents a C atom When describing the compounds of the invention, the terms used are to be construed in accordance with the following definitions, unless a context dictates otherwise:

The term "alkyl" by itself or as part of another substituent refers to a fully saturated hydrocarbon of Formula $C_xH_{2x+1}$ wherein x is a number greater than or equal to 1. Generally, alkyl groups of this invention comprise from 1 to 6 carbon atoms. Alkyl groups may be linear or branched and may be substituted as indicated herein. When a subscript is used herein following a carbon atom, the subscript refers to the number of carbon atoms that the named group may contain. Thus, for example, $C_{1-4}$alkyl means an alkyl of one to four carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers, heptyl and its isomers, octyl and its isomers, nonyl and its isomers; decyl and its isomers. $C_{1-6}$ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopentyl, 2-, 3-, or 4-methylcyclopentyl, cyclopentylmethylene, and cyclohexyl.

The term "aralkyl" as a group of part of a group refers to an alkyl moiety, as detailed above, wherein at least one —H atom is replaced by an aryl moiety.

The term "aryl" as a group of part of a group is generic for a 5- or 6-membered aromatic monocycle optionally comprising 1 or 2 heteroatoms selected from O, N and S; said aryl further being optionally substituted with from 1 to 3 substituents as defined herein.

The term "halo" or "halogen" as a group or part of a group is generic for fluoro, chloro, bromo or iodo.

Unless a context dictates otherwise, asterisks are used herein to indicate the point at which a mono- or bivalent radical depicted is connected to the structure to which it relates and of which the radical forms part. The aforementioned graphical representation has no bearing as to the actual orientation of said groups in the remainder of the molecule.

Whenever used in the present invention, the term 'compounds of the invention' or a similar term is meant to include the compounds of general Formula I or any subgroup thereof. This term also refers to a stereoisomer, tautomer, racemic, metabolite, pro- or predrug, salt, hydrate, or solvate thereof.

As used in the specification and the appended claims, the singular forms "a", "an" and "the" include plural referents unless the context clearly dictates otherwise. By way of example, "a compound" means one compound or more than one compound.

In a preferred embodiment, the present invention provides a compound of formula I, or a stereoisomer, tautomer, racemic, metabolite, pro- or predrug, salt hydrate or solvate thereof, wherein $R_1$ and $R_2$ are each independently selected from the group comprising —H, and -halo;

$R_3$ is —CN, or —B(OH)$_2$ $R_4$ is selected from the group comprising —H or —C$_{1-6}$alkyl; each of said —C$_{1-6}$alkyl being optionally substituted with from 1 to 3 substituents selected from —OH;

$R_5$, $R_6$ and $R_7$ are each independently selected from the group comprising —H, —OH, -oxo, -halo, —C$_{1-6}$alkyl, —O—C$_{1-6}$alkyl, Ar$_2$ and —NR$_8$R$_9$; each of said C$_{1-6}$alkyl being optionally substituted with from 1 to 3 substituents selected from —OH, -halo;

$R_8$ and $R_9$ are each independently selected from the group comprising —H and —Ar$_3$ Ar$_2$ and Ar$_3$ are each independently -phenyl optionally substituted with from 1 to 3-O—C$_{1-6}$alkyl;

n is 0 or 1

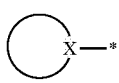

represents a 5 to 10-membered N-containing aromatic or non-aromatic mono- or bicyclic heterocycle, wherein there are exactly 2 ring atoms between the N atom and X; said heterocycle optionally further comprising 1, 2 or 3 heteroatoms selected from O, N and S; and X represents a C atom In yet another preferred embodiment, the present invention provides a compound of formula I, or a stereoisomer, tautomer, racemic, metabolite, pro- or predrug, salt hydrate or solvate thereof, wherein $R_1$ and $R_2$ are each independently selected from the group comprising —H, and —F;

$R_3$ is —CN, and —B(OH)$_2$ $R_4$ is —H;

$R_5$, $R_6$ and $R_7$ are each independently selected from the group comprising —H, -oxo, -halo, —C$_{1-6}$alkyl, and —O—CF$_3$;

n is 0;

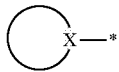

represents a 5 to 10-membered N-containing aromatic or non-aromatic mono- or bicyclic heterocycle, wherein there are exactly 2 ring atoms between the N atom and X; said heterocycle optionally further comprising 1, 2 or 3 heteroatoms selected from O, N and S; and X represents a C atom In a particular embodiment

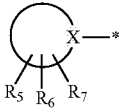

represents a 10-membered N-containing aromatic or non-aromatic bicyclic heterocycle optionally further comprising 1 or 2 heteroatoms selected from O, N and S; wherein at least one of $R_5$, $R_6$ and $R_7$ is selected from the group comprising —H, —OH, -oxo, -halo, —C$_4$alkyl, —O—C$_{1-6}$alkyl, —S—C$_{1-6}$alkyl, —NR$_8$R$_9$, —OR$_{12}$ -Het$_2$ and —Ar$_2$; each of said C$_{1-6}$alkyl being optionally substituted with from 1 to 3 substituents selected from —OH, -halo;

and wherein said $R_5$, $R_6$ or $R_7$ is preferably attached at position 3, 6, 7 or 8 according to the following formula:

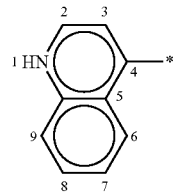

In a particular embodiment

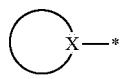

represents a 9 to 10-membered N-containing aromatic or non-aromatic bicyclic heterocycle optionally further comprising 1 or 2 heteroatoms selected from O, N and S; such as for example:

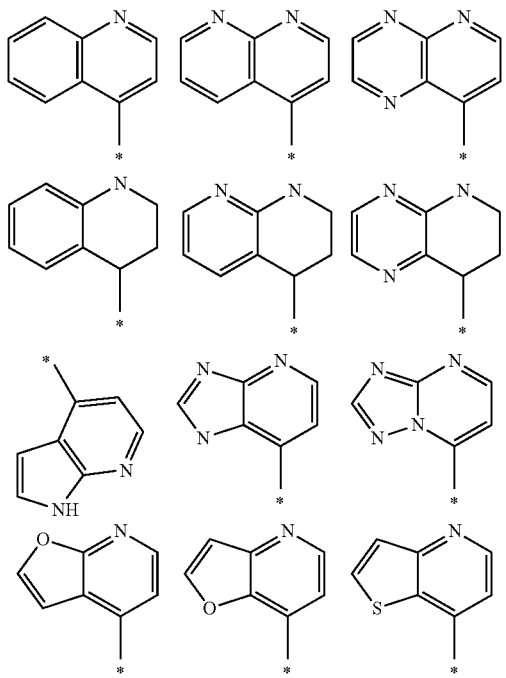

In another particular embodiment

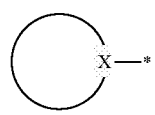

represents a 5 to 6-membered N-containing aromatic or non-aromatic monocyclic heterocycle optionally further comprising 1 or 2 heteroatoms selected from O, N and S selected from the list comprising:

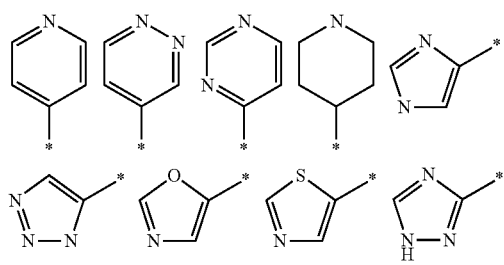

In another particular embodiment

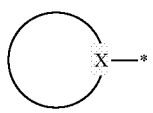

is selected from the list comprising:

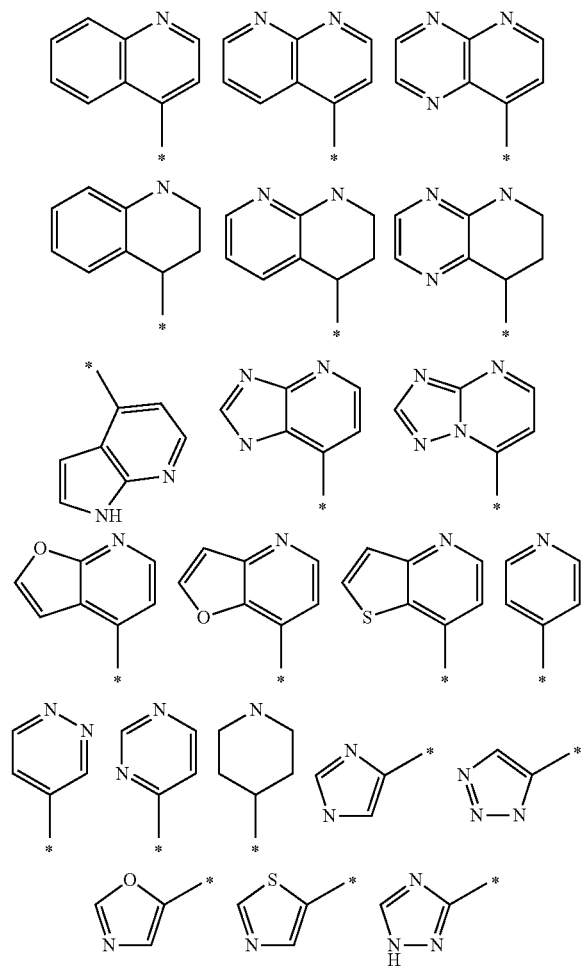

As a further object, the current invention provides a compound according to formula II, or a stereoisomer, tautomer, racemic, metabolite, pro- or predrug, salt, hydrate, or solvate thereof,

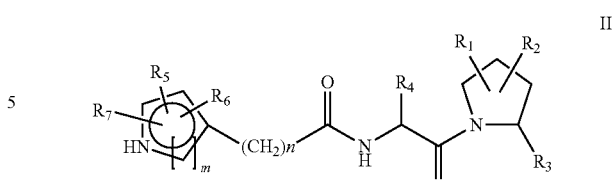

wherein
$R_1$ and $R_2$ are each independently selected from the group comprising —H, OH, -halo, $C_{1-6}$alkyl, —O—$C_{1-6}$alkyl, S—$C_{1-6}$alkyl;
$R_3$ is selected from the group comprising —H, —CN, —B(OH)$_2$, —C(O)alkyl, —C(O)aryl-, —C=C—C(O)aryl, —C≡C—S(O)$_2$aryl, —CO$_2$H, —SO$_3$H, —SO$_2$NH$_2$, —PO$_3$H$_2$, and 5-tetrazolyl
$R_4$ is selected from the group comprising —H, —$C_{1-6}$alkyl, —O—$C_{1-6}$alkyl, —S—$C_{1-6}$alkyl, —Ar$_1$, and —$C_{1-6}$ aralkyl; each of said —$C_{1-6}$alkyl being optionally substituted with from 1 to 3 substituents selected from —OH, -halo
$R_5$, $R_6$ and $R_7$ are each independently selected from the group comprising —H, —OH, -oxo, -halo, —$C_{1-6}$alkyl, —O—$C_{1-6}$alkyl, —S—$C_{1-6}$alkyl, —NR$_8$R$_9$, and —Ar$_2$; each of said $C_{1-6}$alkyl being optionally substituted with from 1 to 3 substituents selected from —OH, -halo $R_8$ and $R_9$, $R_{10}$ and $R_{11}$ are each independently selected from the group comprising —H, —OH, -halo, —$C_{1-6}$alkyl, —O—$C_{1-6}$alkyl, and —S—$C_{1-6}$alkyl;
$R_{10}$ and $R_{11}$ are each independently selected from the group comprising —H, —OH, -halo, —$C_{1-6}$alkyl, —O—$C_{1-6}$alkyl, —S—$C_{1-6}$alkyl, and —Ar$_3$,
Ar$_1$, Ar$_2$ and Ar$_3$ are each independently a 5- or 6-membered aromatic monocycle optionally comprising 1 or 2 heteroatoms selected from O, N and S; each of said Ar$_1$, and Ar$_2$ being optionally and independently substituted with from 1 to 3 substituents selected from —NR$_{10}$R$_{11}$, —$C_{1-6}$alkyl, —O—$C_{1-6}$alkyl, —S—$C_{1-6}$alkyl;
n is 0, 1, 2, or 3
m is 1 or 2

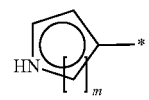

represents a 5 to 6-membered N-containing aromatic or non-aromatic monocyclic heterocycle optionally further comprising 1 or 2 heteroatoms selected from O, N and S.

In a preferred embodiment, the present invention provides a compound according to formula II, wherein
$R_1$ and $R_2$ are each independently selected from the group comprising —H, OH, -halo, $C_{1-6}$alkyl, —O—$C_{1-6}$alkyl, S—$C_{1-6}$alkyl;
$R_3$ is selected from the group comprising —H, —CN, and —B(OH)$_2$
$R_4$ is —H;
$R_5$, $R_6$ and $R_7$ are each independently selected from the group comprising —H, —OH, -oxo, -halo, —$C_{1-6}$alkyl, —O—$C_{1-6}$alkyl, —S—$C_{1-6}$alkyl, —NR$_8$R$_9$, and —Ar$_2$; each of said $C_{1-6}$alkyl being optionally substituted with from 1 to 3 substituents selected from —OH, -halo
$R_8$, $R_9$, $R_{10}$ and $R_{11}$ are each independently selected from the group comprising —H, —OH, -halo, —$C_{1-6}$alkyl, —O—$C_{1-6}$alkyl, and —S—$C_{1-6}$alkyl;

Ar$_2$ is a 5- or 6-membered aromatic monocycle optionally comprising 1 or 2 heteroatoms selected from O, N and S; Ar$_2$ being optionally and independently substituted with from 1 to 3 substituents selected from —NR$_{10}$R$_{11}$, —C$_{1-6}$alkyl, —O—C$_{1-6}$alkyl, —S—C$_{1-6}$alkyl;

n is 0, 1, 2, or 3 m is 1 or 2 is a 5- or 6-membered aromatic or non-aromatic monocyclic heterocycle optionally further comprising 1 or 2 heteroatoms selected from O, N and S; selected from the list comprising In said particular embodiment, preferably, R$_5$ and R$_6$ are each —H; R$_7$ is selected from the group comprising —H, —OH, -oxo, -halo, —C$_{1-6}$alkyl, —O—C$_{1-6}$alkyl, —S—C$_{1-6}$alkyl, —NR$_8$R$_9$, and —Ar$_2$; each of said C$_{1-6}$alkyl being optionally substituted with from 1 to 3 substituents selected from —OH, -halo; and R$_7$ is attached to position 2 or 3, in particular position 2, as represented in In yet another aspect, the present invention provides a compound of formula IIIa, IIIb or IIIc or a stereoisomer, tautomer, racemic, metabolite, pro- or predrug, salt, hydrate, or solvate thereof, wherein R$_1$ and R$_2$ are each independently selected from the group comprising —H, OH, -halo, C$_{1-6}$alkyl, —O—C$_{1-6}$alkyl, S—C$_{1-6}$alkyl;

R$_3$ is selected from the group comprising —H, —CN, —B(OH)$_2$, —C(O)alkyl, —C(O)aryl-, —C≡C—C(O)aryl, —C≡C—S(O)$_2$aryl, —CO$_2$H, —SO$_3$H, —SO$_2$NH$_2$, —PO$_3$H$_2$, and 5-tetrazolyl R$_4$ is selected from the group comprising —H, —C$_{1-6}$alkyl, —O—C$_{1-6}$alkyl, —S—C$_{1-6}$alkyl, —Ar$_1$, and —C$_{1-6}$ aralkyl; each of said —C$_{1-6}$alkyl being optionally substituted with from 1 to 3 substituents selected from —OH, -halo;

R$_5$, R$_6$ and R$_7$ are each independently selected from the group comprising —H, —OH, -oxo, -halo, —C$_{1-6}$alkyl, —O—C$_{1-6}$alkyl, —S—C$_{1-6}$alkyl, —NR$_8$R$_9$, and —Ar$_2$; each of said C$_{1-6}$alkyl being optionally substituted with from 1 to 3 substituents selected from —OH, -halo R$_8$ and R$_9$, are each independently selected from the group comprising —H, —OH, -halo, —C$_{1-6}$alkyl, —O—C$_{1-6}$alkyl, —S—C$_{1-6}$alkyl, and —Ar$_3$ R$_{10}$ and R$_{11}$ are each independently selected from the group comprising —H, —OH, -halo, —C$_{1-6}$alkyl, —O—C$_{1-6}$alkyl, and —S—C$_{1-6}$alkyl;

Ar$_1$, Ar$_2$ and Ar$_3$ are each independently a 5- or 6-membered aromatic monocycle optionally comprising 1 or 2 heteroatoms selected from O, N and S; each of said Ar$_1$, and Ar$_2$ being optionally and independently substituted with from 1 to 3 substituents selected from —NR$_{10}$R$_{11}$, —C$_{1-6}$alkyl, —O—C$_{1-6}$alkyl, —S—C$_{1-6}$alkyl;

n is 0, 1, 2, or 3 m is 1 or 2 represent a 9 to 10-membered N-containing aromatic or non-aromatic bicyclic heterocycle optionally further comprising 1 or 2 heteroatoms selected from O, N and S.

In a particular embodiment, the current invention provides a compound according to formula III, wherein R₁ and R₂ are each independently selected from the group comprising —H, OH, -halo, C₁₋₆alkyl, —O—C₁₋₆alkyl, S—C₁₋₆alkyl;

R₃ is selected from the group comprising —H, —CN, and —B(OH)₂;

R₄ is —H;

R₅, R₆ and R₇ are each independently selected from the group comprising —H, —OH, -oxo, -halo, —C₁₋₆alkyl, —O—C₁₋₆alkyl, —S—C₁₋₆alkyl, —NR₈R₉, and —Ar₂; each of said C₁₋₆alkyl being optionally substituted with from 1 to 3 substituents selected from —OH, -halo R₈, R₉, R₁₀ and R₁₁ are each independently selected from the group comprising —H, —OH, -halo, —C₁₋₆alkyl, —O—C₁₋₆alkyl, and —S—C₁₋₆alkyl;

Ar₂ is a 5- or 6-membered aromatic monocycle optionally comprising 1 or 2 heteroatoms selected from O, N and S; Ar₂ being optionally and independently substituted with from 1 to 3 substituents selected from —NR₁₀R₁₁, —C₁₋₆alkyl, —O—C₁₋₆alkyl, —S—C₁₋₆alkyl;

n is 0, 1, 2, or 3
m is 1 or 2

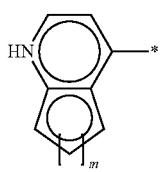

is a 9- or 10-membered aromatic or non-aromatic bicyclic heterocycle optionally further comprising 1 or 2 heteroatoms selected from O, N and S; selected from the list comprising

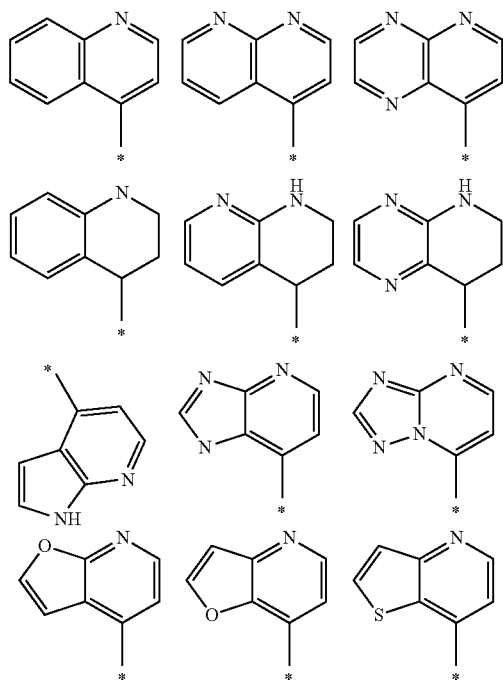

In said particular embodiment, preferably, R₅ is attached to position 2 or 3, in particular position 3, as represented in:

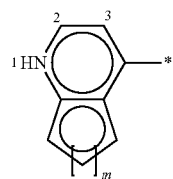

Furthermore, for 9-membered aromatic or non-aromatic bicyclic heterocycles, preferably R₆ is —H and R₇ is attached to position 7 as represented in:

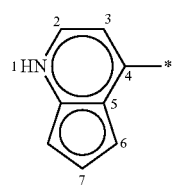

For 10-membered aromatic or non-aromatic bicyclic heterocycles, R₆ and R₇ may be present at any suitable position, i.e. position 6, 7, 8 or 9 as represented in:

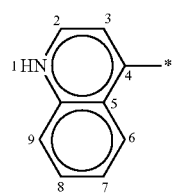

As a further object, this invention provides a compound according to this invention for use as a human or veterinary medicine.

This invention also provides a pharmaceutical composition comprising a compound according to this invention; said composition being suitable for use as a human or veterinary medicine.

For example, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. No. 6,372,778, U.S. Pat. No. 6,369,086, U.S. Pat. No. 6,369,087 and U.S. Pat. No. 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

Generally, the compounds of this invention may be formulated as a pharmaceutical preparation or pharmaceutical composition comprising at least one compound of the invention and at least one pharmaceutically acceptable carrier, diluent or excipient and/or adjuvant.

By means of non-limiting examples, such a formulation may be in a form suitable for oral administration, parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is again made to for instance U.S. Pat. No. 6,372,778, U.S. Pat. No. 6,369,086, U.S. Pat. No. 6,369,087 and U.S. Pat. No. 6,372,733, as well as to the standard handbooks, such as the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, creams, lotions, soft and hard gelatin capsules, suppositories, eye drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein, for example using liposomes or hydrophilic polymeric matrices based on natural gels or synthetic polymers. In order to enhance the solubility and/or the stability of the compounds of a pharmaceutical composition according to the invention, it can be advantageous to employ α-, β- or γ-cyclodextrins or their derivatives.

In addition, co-solvents such as alcohols may improve the solubility and/or the stability of the compounds. In the preparation of aqueous compositions, addition of salts of the compounds of the invention can be more suitable due to their increased water solubility.

The preparations may be prepared in a manner known per se, which usually involves mixing at least one compound according to the invention with the one or more pharmaceutically acceptable carriers, and, if desired, in combination with other pharmaceutical active compounds, when necessary under aseptic conditions. Reference is again made to U.S. Pat. No. 6,372,778, U.S. Pat. No. 6,369,086, U.S. Pat. No. 6,369,087 and U.S. Pat. No. 6,372,733 and the further prior art mentioned above, as well as to the standard handbooks, such as the latest edition of Remington's Pharmaceutical Sciences.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the invention, e.g. about 10, 25, 50, 100, 200, 300 or 400 mg per unit dosage.

The compounds can be administered by a variety of routes including the oral, rectal, ocular, transdermal, subcutaneous, intravenous, intramuscular or intranasal routes, depending mainly on the specific preparation used and the condition to be treated or prevented, and with oral and intravenous administration usually being preferred. The at least one compound of the invention will generally be administered in an "effective amount", by which is meant any amount of a compound of the Formula I or II, upon suitable administration, is sufficient to achieve the desired therapeutic or prophylactic effect in the individual to which it is administered. Usually, depending on the condition to be prevented or treated and the route of administration, such an effective amount will usually be between 0.01 to 1000 mg per kilogram body weight day of the patient per day, more often between 0.1 and 500 mg, such as between 1 and 250 mg, for example about 5, 10, 20, 50, 100, 150, 200 or 250 mg, per kilogram body weight day of the patient per day, which may be administered as a single daily dose, divided over one or more daily doses, or essentially continuously, e.g. using a drip infusion. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. No. 6,372,778, U.S. Pat. No. 6,369,086, U.S. Pat. No. 6,369,087 and U.S. Pat. No. 6,372,733 and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous administration, the compound according to the invention, if desired with the substances customary therefore such as solubilizers, emulsifiers or further auxiliaries are brought into solution, suspension, or emulsion. The compounds of the invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquefy and/or dissolve in the rectal cavity to release the drug.

In a preferred embodiment, the compounds of the present invention are useful in human or veterinary medicine, in particular for use as FAP (fibroblast activation protein) inhibitors.

It is generally known that FAP exhibits both endo- and exopeptidase activity, mediated by the same active center. As further detailed in the examples that follow hereinafter, the newly developed inhibitors are capable of inhibiting both said endo- and exopeptidase activity. Therefore, FAP inhibition as used in the context of this invention is to include inhibition of endopeptidase activity and/or exopeptidase activity of FAP.

The present invention further provides the use of a compound as defined hereinbefore or the use of a composition comprising said compound, as a human or veterinary medicine, in particular for the prevention and/or treatment of FAP-related disorders.

In the invention, particular preference is given to compounds of Formula I or any subgroup thereof which inhibit FAP activity with an $IC_{50}$ value of less than 10 μM, preferably less than 1 μM, most preferably less than 0.1 μM.

Said inhibition may be effected in vitro and/or in vivo, and when effected in vivo, is preferably effected in a selective manner, as defined herein.

Particular reference is given to compounds of Formula I or any subgroup thereof which are at least 100× more selective for FAP compared to DPPIV, DPP9 and DPP2; in particular at least 1000× more selective for FAP compared to DPPIV, DPP9 and DPP2.

Particular reference is also given to compounds of Formula I or any subgroup thereof which are at least 10× more selective for FAP compared to PREP, in particular at least 20 to 50× more selective for FAP compared to PREP.

The term "FAP-related disorder" as used herein, means any disease or other deleterious condition in which FAP is known to play a role. The term "FAP-related disorder" also means those diseases or conditions that are alleviated by treatment with a FAP inhibitor. Accordingly, another embodiment of the present invention relates to treating or lessening the severity of one or more diseases in which FAP is known to play a role. A non-limiting list of examples of FAP-related disorders can include proliferative diseases selected from the group comprising breast cancer, colorectal cancer, ovarian cancer, prostate cancer, pancreatic cancer, kidney cancer, lung cancer, melanoma, fibrosarcoma, bone and connective tissue sarcomas, renal cell carcinoma, giant cell carcinoma, squamous cell carcinoma, and adenocarcinoma. In addition, the list of FAP-related disorders that are envisaged here, includes diseases characterised by tissue remodeling and/or chronic inflammation. These include but are not limited to fibrotic disease, wound healing, keloid formation, osteoarthritis, rheumatoid arthritis and related disorders involving cartilage degradation, atherosclerotic disease and Chron's disease. Furthermore, FAP related disorders involving endocrinological dysfunction (including but not limited to disorders of glucose metabolism) and diseases involving blood clotting disorders are part of this list.

The invention also provides methods for the prevention and/or treatment of a FAP-related disorder; said method comprising administering to a subject in need thereof a compound according to this invention, or a composition comprising said compound.

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

The invention will now be illustrated by means of the following synthetic and biological examples, which do not limit the scope of the invention in any way.

EXAMPLES

Compounds of formula (I) can be prepared as indicated in general Scheme 1. The variables are as defined above for formula I Scheme 1. General scheme for the synthesis of compounds defined by formula I

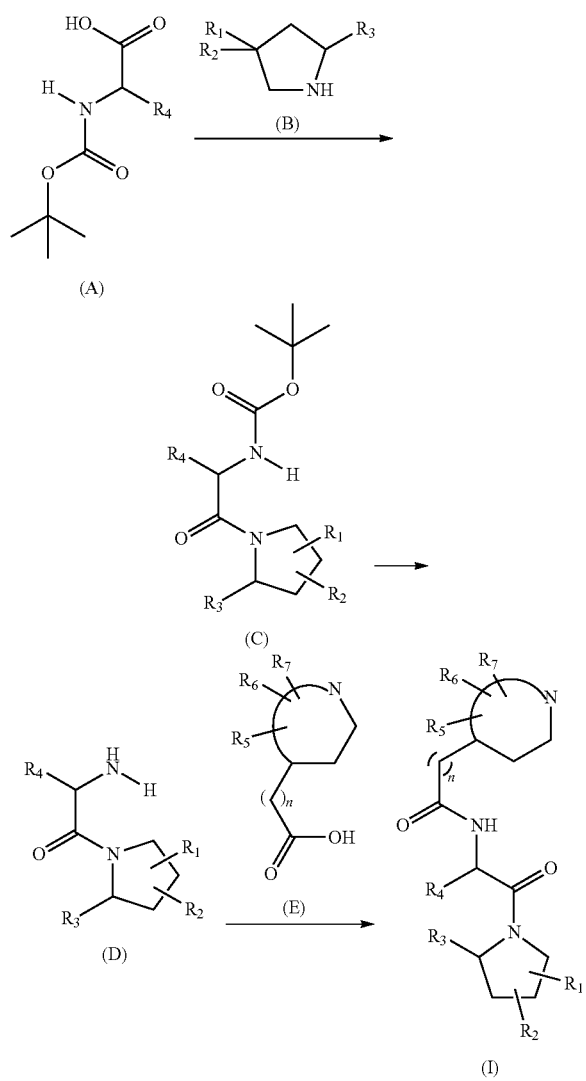

Scheme 1. General scheme for the synthesis of compounds defined by formula I

This can be carried out as mentioned below,

The reaction of Boc-aminocarboxylate (A) with compound (B) can be done using standard techniques for peptide coupling, known to a person skilled in the art, to afford compound (C). This is either pyrrolidine or a pyrrolidine derivative. In cases where the pyrrolidine is a pyrrolidinecarboxamide an additional dehydration step (e.g. using trifluoroacetic anhydride and pyridine, vide infra) has to follow the coupling step.

The chosen protecting group of (C), including the Boc- and Z-group can be deprotected using a suitable acid or other deprotecting agent, known to a person skilled in the art, to generate compound (D).

The reaction of compound (D) with compound (E) can be done using standard peptide coupling procedures, or using a corresponding acyl halide or active ester of (E) which is made in situ or in a separate reaction using procedures known to a person skilled in the art.

Alternatively, compounds of formula (I) can also be prepared by converting one or more groups $R_1$, $R_2$, $R_3$, $R_4$, $R_5$, $R_6$ or $R_7$ of another compound of formula (I) obtained as mentioned above, into a desired substituent. The selected conversion method will depend on the kind of substituents desired. For example, it can be carried out by the following methodologies (Method a to Method e).

(Method a): A compound of type (I) in which $R_5$, $R_6$ or $R_7$ in formula (I) is a hydrogen atom can be prepared by eliminating a protective group from a corresponding Compound (I) in which $R_5$, $R_6$ or $R_7$ is a protective group. Removal of the protective group can be carried out by conventional methodology, known to a person skilled in the art (e.g. acid treatment, base treatment, catalytic reduction, etc.).

(Method b): A compound of type (I) in which $R_3$ is a boronic acid function, can be prepared by removing a protective group from a corresponding compound of formula (I) in which $R_3$ is a protected boronate (e.g. a dialkyl ester, a pinanediol diester)[15]

(Method c): A compound of type (I) in which $R_3$ is a carbonitrile function, can be prepared by dehydration of a corresponding compound of formula (I) in which $R_3$ is a carboxamide function.

(Method d): A compound of type (I) in which $R_4$ is a proteinogenic or non-proteinogenic amino acid side chain, can be obtained by eliminating a protective group from a corresponding Compound (I) in which $R_4$ is a protected proteinogenic or non-proteinogenic amino acid side chain. Removal of the protective group can be carried out by conventional methodology, known to a person skilled in the art (e.g. acid treatment, base treatment, catalytic reduction, etc.).

(Method e) A compound of type (I) can be made by reacting compound (II) with a suitable protected compound (V), using standard peptide coupling procedures, or using a corresponding acyl halide or active ester of (II) which is made in situ or in a separate reaction using procedures known to a person skilled in the art. Followed by reaction with (IV) using standard peptide coupling procedures, or using a corresponding acyl halide or active ester of (II) which is made in situ or in a separate reaction using procedures known to a person skilled in the art.

Compounds of formula (B) are commercially available or can be prepared according to methods known to one skilled in the art or by methods disclosed herein.

For example, (S)-4,4-difluoropyrrolidine-2-carboxamide hydrochloride can be made as described in general procedure A. This is starting from (S)-1-tert-butyl 2-methyl 4-oxopyrrolidine-1,2-dicarboxylate which is fluorinated with diethylaminosulfur trifluoride (DAST) and subsequently hydrolyzed with potassium hydroxide. The amide is made from this acid, reacting it with dicyclohexylcarbodiimide and N-hydroxysuccinimide, subsequent removal of the Boc group yields the hydrochloride salt (B).

For example, prolinamide was bought from commercial suppliers (Fluorochem).

For example, the pinanediol ester of pyrrolidineboronic acid can be made as described in reference 12.

(2S,4S)-4-fluoropyrrolidine-2-carboxamide can be prepared as described analogously to (S)-4,4-difluoropyrrolidine-2-carboxamide, starting from 1-tert-butyl 4-hydroxypyrrolidine-1,2 dicarboxylate.

Compounds of formula (E) of the present invention, can for example be obtained directly from commercial sources or be prepared from commercially available compounds as indicated in Scheme 2a for substituted quinoline-4-carboxylates or in Scheme 2b for the preparation of 2-aminopyridine-4-carboxylate derivatives and Scheme 2c for 2-(hetero)aryl-4-carboxylate derivatives.

Non-limiting list of commercially available compounds for preparing a compound of formula E:

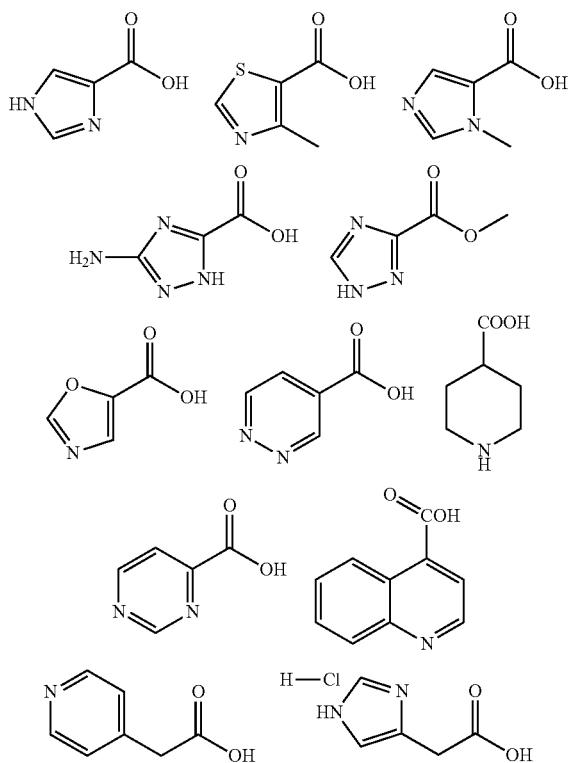

Scheme 2a. Synthesis of compounds of Type II with a substituted quinoline-4-carboxylate basic structure.

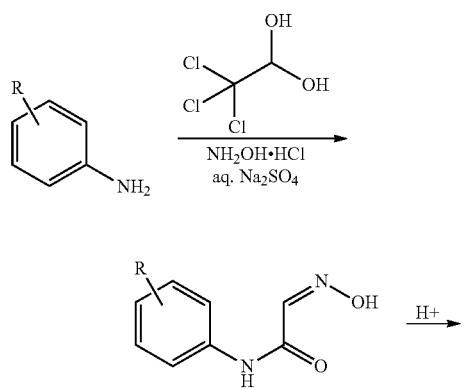

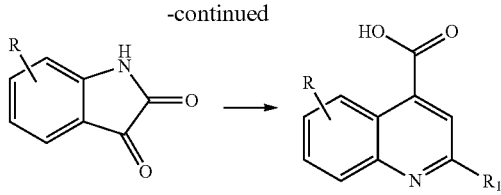

The quinoline-4-carboxylic acid [E] can be prepared using the classical Sandmeyer isatin synthesis followed by the Pfitzinger reacton. The aniline was reacted with chloral hydrate and hydroxylamine hydrochloride to afford the substituted isonitrosoacetanilide which was cyclized using a suitable acid catalyst to afford the isatin as described in. Alternatively the isatin can be bought from commercial sources. The isatin can then be converted into the corresponding substituted quinoline-4-carboxylic acid using the Pfitzinger reaction as in reference 17. In some instances the Pfitzinger reaction yielded a quinoline-2,4-dicarboxylic acid which was decarboxylated to the quinoline-4-carboxylic acid by reacting it in water for 2 h using a pressured tube at 200° C.

Scheme 2b: Synthesis of 2-aminopyridine-4-carboxylate derivatives.

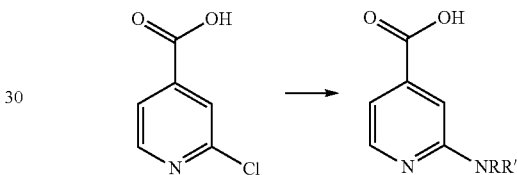

The 2-aminopyridine-4-carboxylic acids can be prepared by nucleophilic aromatic substitution of 2-chloropyridine-4-carboxylic acid with the corresponding primary or secondary amines.

Scheme 2c: Synthesis of 2-(hetero)aryl-4-carboxylate derivatives.

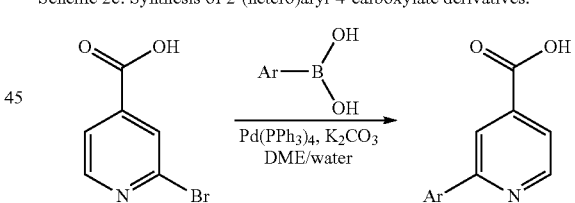

The 2-(hetero)aryl-4-carboxylate derivatives can be prepared by the palladium catalyzed coupling of 2-bromopyridine-4-carboxylic acid with the corresponding boronic acid.

Experimental Section

The experimental section is divided into three parts:
1. Synthetic procedures
2. In vitro and in vivo assay protocols
3. Biochemical evaluation results 1 Synthetic Procedures Reagents were obtained from Sigma-Aldrich, Acros organics or Fluorochem and were used without further purification, unless otherwise mentioned. Characterization of all compounds was done with 1H NMR and mass spectrometry. $^1$H NMR spectra were recorded on a 400 MHz Bruker Avance III nanobay spectrometer with ultrashield. In some NMR spectra, only the most important rotamer shown. Chemical shifts are in ppm and coupling constants are in Hz. ES mass spectra were obtained from an Esquire 3000plus iontrap mass spectrometer from Bruker Daltonics. Purity was verified using two diverse HPLC systems using, respectively, a mass and UV-detector. Water (A) and CH$_3$CN (B) were used as eluents. LC-MS spectra were recorded on an Agilent 1100 Series HPLC system using a Alltech Prevail C18 column (2.1×50 mm, 3 µm) coupled with an Esquire 3000plus as MS detector and a 'method A' 5-100% B, 20 min gradient was used with a flow rate from 0.2 mL/min. Formic acid 0.1% was added to solvents A and B. When necessary, the products were purified with flash chromatography on a Biotage® ISOLERA One flash system equipped with a internal variable dual-wavelength diode array detector (200-400 nm). For normal phase purifications SNAP cartridges (10-340 g; flow rate 10 mL/min.-100 mL/min.) were used, reversed phase purifications were done making use of KP-C18 containing cartridges. Dry sample loading was done by self packing Samplet® cartridges using silica or Celite 545 respectively for normal- and reversed phase purifications. Gradients used varied by purification. However typical gradients used for normal phase were 30 min. gradient of 0-50% EtOAc in hexane to 100 hexane or 0-5% MeOH in DCM to 20% MeOH in DCM and for reversed phase a gradient of 10% ACN in water to 50% ACN in water. Waters acquity UPLC system coupled to a waters TQD ESI mass spectrometer and waters TUV detector. A waters acquity UPLC BEH C18 1.7 µm 2.1×50 mm column was used. Solvent A: water with 0.1% formic acid, Solvent B: acetonitrile with 0.1% formic acid. Method I: In 1.75 min from 95% A, 5% B to 95% B, 5% A, then 0.25 min 95% B, 5% A. The wavelength for UV detection was 254 nm. Method II: In 4.75 min from 95% A, 5% B to 95% B, 5% A, then 0.25 min 95% B, 5% A. The wavelength for UV detection was 214 nm. HRMS: The dry samples were dissolved in 1 ml methanol and diluted 1/100 in CH$_3$CN/H$_2$O 0.1% formic acid. 10 µl of each sample was injected using the CapLC system (Waters, Manchester, UK) and electrosprayed through the Nanomate (Advion, Ithaca, N.Y.) nanoelectrospray source. The Nanomate was operated in positive ion mode at an electrospray potential of 1.5 kV. Samples were injected with an interval of 3 minutes Positive ion mode accurate mass spectra were acquired using a Q-TOF II instrument (Waters, Manchester, UK). The MS was calibrated prior to use with a 0.2% H$_3$PO$_4$ solution. The spectra were lock mass corrected using the know mass of the nearest H$_3$PO$_4$ cluster or the phthalate background ions. The Waters acquity UPLC system coupled to a waters TQD ESI mass spectrometer was also used for LC/MS/MS measurements.

This section will be further divided into two parts:
1.1: Synthesis of intermediates of formula (D), via intermediates of formula (A), (B) and (C), as defined in Scheme 1.
1.2: Synthesis of target products and intermediates of formula (I), via intermediates (D) and (E), as defined in Scheme 1.

1.1: Synthesis of Intermediates of Formula (D), Via Intermediates of Formula (A), (B) and (C)

1.1.1 Synthesis of (S)-1-(2-Aminoacetyl)pyrrolidine-2-carbonitrile 2,2,2-trifluoroacetate The synthetic pathway toward this compound is depicted in Scheme 3.

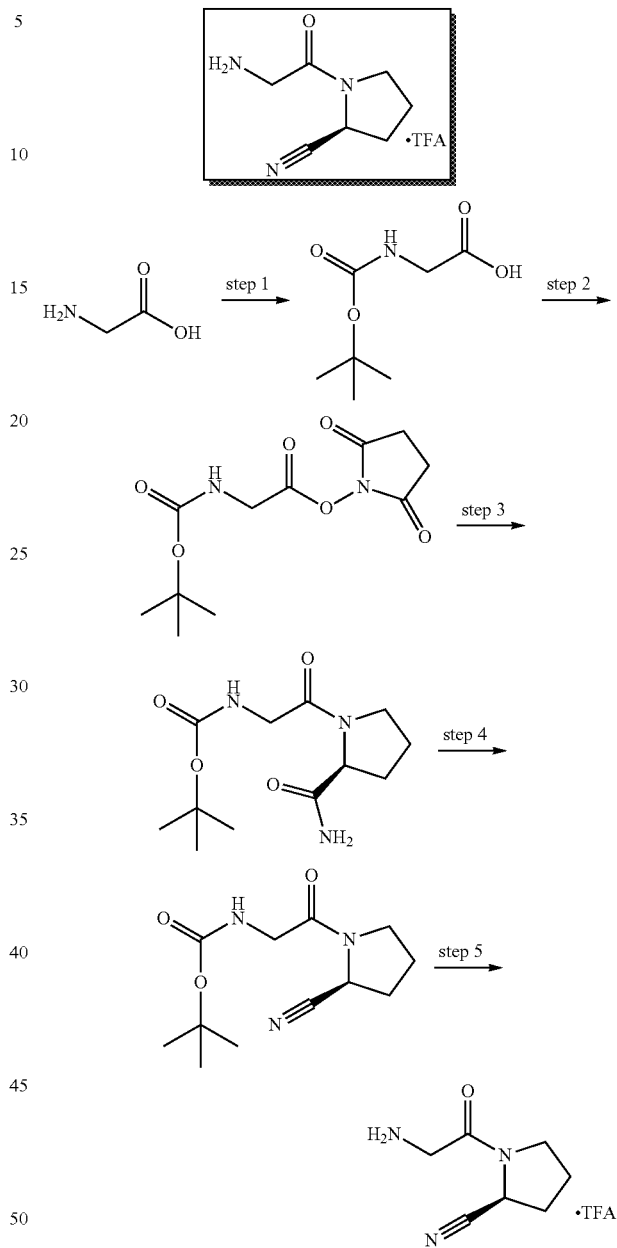

Step 1: 2-(tert-Butoxycarbonylamino)acetic acid

Glycine (3 g, 40.0 mmol) was dissolved in a dioxane-water (1:1) (100 mL) mixture. Triethylamine (5.54 mL, 40.0 mmol) and di-tert-butyl dicarbonate (8.72 g, 40.0 mmol) were added and the mixture was stirred for 2 h at room temperature. After evaporation of the volatiles, redissolving in water, the solution was washed with diethylether (25 mL). The pH was set to 2 with 2N HCl. The mixture was extracted with ethyl acetate (2×5 mL), dried over sodium sulfate and concentrated in vacuo, yielding a white crystalline product. Yield: 6.9 g, 99%

MS (ESI) m/z 198.1 [M+Na]$^+$.

Step 2: 2,5-Dioxopyrrolidine-1-yl 2-(tert-butoxycarbonylamino)acetate

N-Boc-glycine (7.31 g, 41.7 mmol) was dissolved in 100 mL of DCM and to the cooled (15° C.) solution N-hydroxysuccinimide (5.28 g, 45.9 mmol) was added. N,N'-dicyclohexylcarbodiimide (9.47 g, 45.9 mmol) was added to the formed suspension under vigorous stirring. After a few seconds, a cloudy white suspension formed, the mixture was allowed to reach room temperature and stirred for 1 h. It was subsequently filtrated over celite, washed with 50 mL saturated sodium bicarbonate, dried over sodium sulfate and concentrated in vacuo to yield a crystalline powder. Yield: 7.02 g, 61.8%

$^1$H NMR (400 MHz, DMSO-d$_6$): δ 1.38 (s, 9H), 2.80 (s, 4H), 4.07 (d, J=6 Hz, 2H), 7.43 (br s, 1H).
MS (ESI) m/z 567.2 [2M+Na]$^+$.

Step 3: (S)-tert-Butyl 2-(2-carbamoylpyrrolidine-1-yl)-2-oxoethylcarbamate

A solution of the N-hydroxysuccinimidate obtained from step 2 (8.22 g, 46.9 mmol) in dichloromethane (100 mL) was cooled in a cooling bath to 15° C. After 15 min, a solution of (S)-pyrrolidine-2-carboxamide (5.1 g, 44.7 mmol, bought from commercial supplier Fluorochem) and 2.1 eq of Hünig's base in 50 mL of dichloromethane were added. After 3 h, the resulting solution was washed with 1N hydrochloric acid, with saturated sodium bicarbonate, brine, dried over sodium sulfate, filtrated and evaporated to dryness. The crude mixture was purified using flash chromatography with 5% methanol in DCM.
Yield: 8.61 g, 71%
$^1$H NMR (400 MHz, DMSO-d$_6$): δ 1.38 (s, 9H), 1.72-2.22 (m, 4H), 3.38-3.45 (m, 1H), 3.49-3.55 (m, 1H), 3.74 (d, J=5.7 Hz, 2H), 4.18 (dd, J=8.8, 2.8 Hz, 1H), 5.43 (br s, 1H), 5.54 (br_s, 1H), 6.83 (br s, 1H)
MS (ESI) m/z 294.2 [M+Na]$^+$.

Step 4: (S)-tert-butyl 2-(2-cyanopyrrolidine-1-yl)-2-oxoethylcarbamate

The amide obtained from step 3 (1.77 g, 6.52 mmol) was dissolved in 80 mL of dichloromethane. Pyridine (5.27 mL, 65.2 mmol) was added to the cooled solution (−15° C.), followed by the dropwise addition of trifluoroacetic anhydride (1.012 mL, 7.18 mmol) solution in 15 mL of dichloromethane. The resulting transparent yellowish solution was stirred for 90 min. The mixture was washed with 1M HCl (3×30 mL), saturated sodium bicarbonate (1×40 mL) and brine. The organic layer was dried over Na$_2$SO$_4$, and concentrated to afford the crude product which was purified using column chromatography (hexane/ethyl acetate gradient) to afford the product as a yellowish oil.
Yield: (1.21 g, 73%).
$^1$H NMR (400 MHz, DMSO-d$_6$): δ 1.37 (s, 9H), 1.73-1.89 (m, 3H), 1.94-2.00 (m, 1H), 3.34-3.43 (m, 1H), 3.49-3.53 (m, 1H), 3.73 (d, J=5.6 Hz, 2H), 4.23 (dd, J=36, 7.6 Hz, 1H), 6.68 (br s, 1H).
MS (ESI) m/z 276.1[M+Na]$^+$.

Step 5: (S)-1-(2-aminoacetyl)pyrrolidine-2-carbonitrile 2,2,2-trifluoroacetate The nitrile obtained from step 4 (1.21 g, 4.78 mmol) was dissolved in acetonitrile (9.95 mL, 191.3 mmol) and cooled to 0° C. Trifluoroacetic acid (7.1 mL, 96.63 mmol) was added dropwise. The solution was stirred overnight, concentrated and washed with ether (2×15 mL) to yield the crude product as an orange oily substance Yield: 2.00 g, 99%.
$^1$H NMR (400 MHz, DMSO-d$_6$): δ 1.92-2.09 (m, 2H), 2.10-2.21 (m, 2H), 3.39-3.47 (m, 1H), 3.57-3.64 (m, 1H), 3.86 (q, J=18.2 Hz, 2H), 4.83 (dd, J=7.0, 4.34 Hz, 1H), 8.2 (br s, 3H)
MS (ESI) m/z 154.2 [M+H]$^+$

1.1.2 Synthesis of (S)-1-(2-aminoacetyl)-4,4-difluoropyrrolidine-2-carbonitrile 2,2,2-trifluoroacetate starting from (2S,4R)-1-tert-butyl 2-methyl 4-hydroxypyrrolidine-1,2-dicarboxylate The synthetic pathway toward this compound is depicted in Scheme 4.

Scheme 4: Synthesis of a glycyl(2-cyano-4,4-difluoropyrrolidine) intermediate of formula (D)

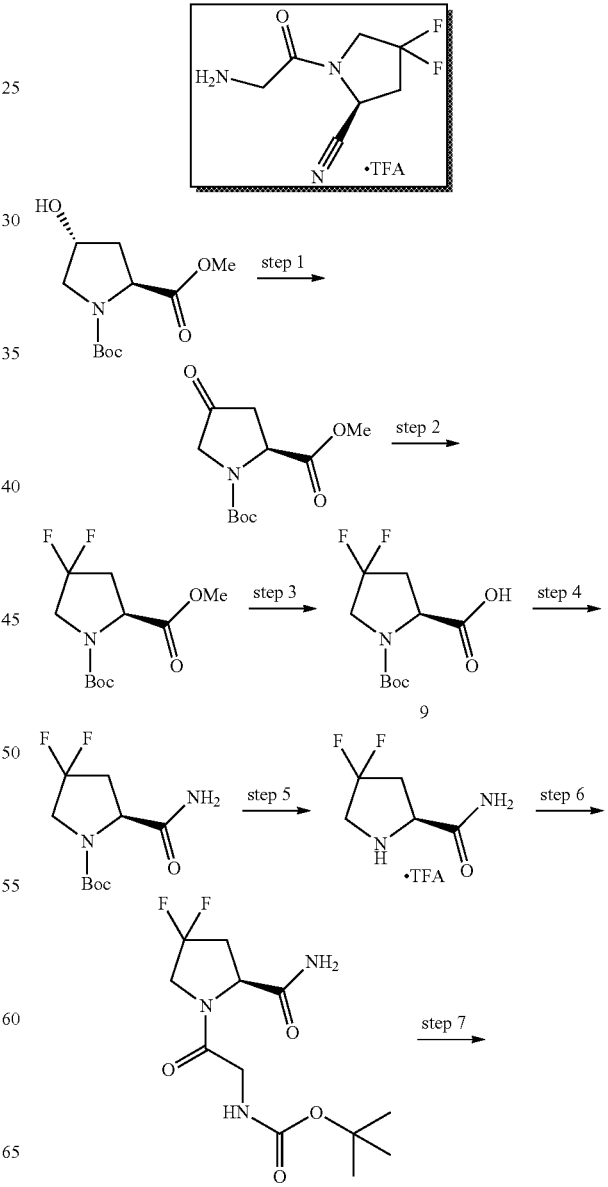

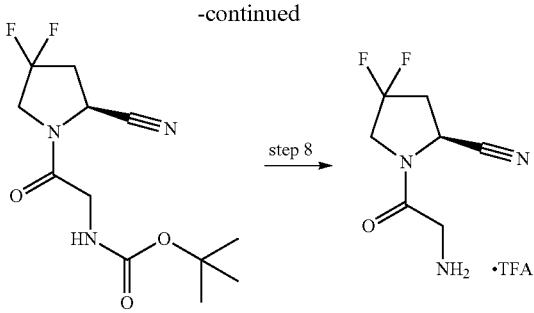

Step 1: (S)-1-tert-butyl 2-methyl 4-oxopyrrolidine-1,2-dicarboxylate 1,3,5-Trichloro-1,3,5-triazinane-2,4,6-trione (3.78 g, 16.27 mmol) was added to a cooled (0° C.) solution of (S)-1-tert-butyl 2-methyl 4-oxopyrrolidine-1,2-dicarboxylate (3.8 g, 15.49 mmol) in DCM (25 mL), followed by the addition of catalytic TEMPO (0.024 g, 0.155 mmol). After 5 min the mixture was allowed to reach room temperature, stirred for another 30 minutes and filtrated over Celite. The organic layer was washed with 20 mL saturated potassium carbonate solution, washed with brine, dried over anhydrous sodium sulfate, filtrated and evaporated. The crude compound 1 was used without further purification.

Yield: 2.77 g, 74%.
$^1$H NMR (400 MHz, CDCl$_3$): δ 1.46 (s, 9H), 2.57 (dd, J=18.8, 2.4, 1H), 2.90 (s, 1H), 3.75 (s, 3H), 3.88 (br s, 2H), 4.77 (dd, J=36.8, 8 Hz, 1H).
MS (ESI) m/z 376.2 [M+MeOH+H]$^+$.

Step 2: (S)-1-tert-butyl 2-methyl 4,4-difluoropyrrolidine-1,2-dicarboxylate

A solution of the (S)-1-tert-butyl 2-methyl 4-oxopyrrolidine-1,2-dicarboxylate (0.23 g, 0.946 mmol), obtained from step 1, in CH$_2$Cl$_2$ (3.0 mL), in a 25-mL flask equipped with a N$_2$ inlet tube and stirring bar, was treated with a solution of diethylaminosulfur trifluoride (0.197 ml, 1.607 mmol) in CH$_2$Cl$_2$ (2.0 mL) at room temperature. Ethanol (0.011 ml, 0.189 mmol) was added (for in situ generation of catalytic quantities of HF) and the mixture was stirred for 18 h at room temperature. The solution was poured into saturated sodium bicarbonate and after CO$_2$ evolution ceased it was extracted into CH$_2$Cl$_2$ (3×15 mL), dried (Na2SO4), filtered, and evaporated in vacuo. Chromatography on silica gel in DCM afforded a yellowish oil.

Yield: 0.150 g, 61%.
$^1$H NMR (400 MHz, CDCl$_3$): δ 1.44 (br s, 9H), 2.45 (dq, J=13.6, 5.2 Hz, 1H), 2.61-2.81 (m, 1H), 3.75 (s, 3H), 3.60-3.90 (m, 2H), 4.45-4.55 (m, 1H).
MS (ESI) m/z 266.1 [M+H]$^+$

Step 3: (S)-1-(tert-butoxycarbonyl)-4,4-difluoropyrrolidine-2-carboxylic acid (S)-1-tert-butyl 2-methyl 4,4-difluoropyrrolidine-1,2-dicarboxylate (1.51 g, 5.69 mmol), obtained from step 2, was dissolved in 6 mL of 1M potassium hydroxide solution. The solution was stirred overnight. The mixture was washed with ether, acidified, extracted with ethyl acetate, washed with brine, dried over sodium sulfate, filtered and evaporated to yield slightly brownish crystals. The crude mixture was used without further purification. Yield: 1.23 g, 86%
$^1$H NMR (400 MHz, DMSO-d$_6$): δ 1.38 (s, 9H), 2.32-2.48 (m, 1H), 2.78-2.98 (m, 1H), 3.65-3.77 (m, 2H), 4.31-4.37 (m, 1H), 13.0 (br s, 1H).
MS (ESI) m/z 250.8 [M−H]$^−$
LC-MS (I) R$_t$ 1.51 min, m/z 252.5 [M+H]$^+$ (90%).

Step 4: (S)-tert-butyl 2-carbamoyl-4,4-difluoropyrrolidine-1-carboxylate

In a 50 mL round-bottomed flask (S)-1-(tert-butoxycarbonyl)-4,4-difluoropyrrolidine-2-carboxylic acid (1.6 g, 6.37 mmol), obtained from step 4, was dissolved in 10 mL of dichloromethane at 15° C. Then 1-hydroxypyrrolidine-2,5-dione (0.806 g, 7.01 mmol) was added. To the formed suspension N,N-dicyclohexylcarbodiimide (1.445 g, 7.01 mmol) was added at vigorous stirring. In a few seconds a cloudy white suspension forms. The mixture was allowed to reach RT and stirred for 30 min, followed by the addition of 7N ammonia in methanol (2.002 ml, 14.01 mmol) and stirring for another 20 min. Before evaporation of volatile components 1 spoon of Celite was added to the flask. Cold ethyl acetate was added to the residue and filtered over Celite. The filtrate was washed with saturated sodium bicarbonate. The formed slightly yellowish crystals were used without further purification.

Yield: 1.15 g, 72%
$^1$H NMR (400 MHz, CDCl$_3$): δ 1.45 (s, 9H), 2.77-2.44 (m, 1H), 2.82-3.02 (m, 1H), 3.56-3.78 (m, 1H), 3.80-4.00 (m, 1H), 4.52 (br_s, 1H), 5.54 (br s, 1H), 6.77 (br_s, 1H).
LC-MS (I) R$_t$ 1.34 min, m/z 251.5 [M+H]$^+$ (89%).
MS (ESI) m/z 251.2 [M+H]$^+$

Step 5: (S)-4,4-difluoropyrrolidine-2-carboxamide trifluoroacetate 9.54 mL of trifluoroacetic acid was added to a solution of (S)-tert-butyl 2-carbamoyl-4,4-difluoropyrrolidine-1-carboxylate (1.25 g, 5 mmol) in 10 mL of dichloromethane. The solution was stirred for 1 hour before evaporation. The residue was washed with ether to yield white crystals.

Yield: 0.84 g, 90%
$^1$H NMR (400 MHz, DMSO-d$_6$): δ 2.42-2.61 (m, 1H), 2.86-3.00 (m, 1H), 3.71 (dd, J=19.54, 7.48 Hz, 2H), 4.46 (t, J=8.59 Hz, 1H), 7.82 (s, 1H), 8.07 (s, 1H), 10.01 (br_s, 2H).
MS (ESI) m/z 155.2 [M+H]$^+$

Step 6: (S)-tert-butyl 2-(2-carbamoyl-4,4-difluoropyrrolidin-1-yl)-2-oxoethylcarbamate HATU (12.47 g, 32.8 mmol) was dissolved in 20 mL DMF and added to a solution of 2-(tert-butoxycarbonylamino)acetic acid (5.75 g, 32.8 mmol), as obtained in Scheme 4 from step 1, and DIPEA (5.43 ml, 32.65 mmol) in 30 mL DCM. After 15 min a solution of (S)-4,4-difluoropyrrolidine-2-carboxamide hydrochloride (5.1 g, 27.3 mmol) and DIPEA (9.06 ml, 54.38 mmol) in 40 mL DCM was added. After 3 h the cloudy mixture was filtered of. The filtrate was cooled and filtrated again. The combined residues were washed with DCM and water.

Yield: 8.39 g, 77%
$^1$H NMR (400 MHz, DMSO-d$_6$) δ 1.39 (s, 9H), 2.30-2.43 (m, 1H), 2.65-2.78 (m, 1H), 3.71 (dd, J=17.2, 5.32 Hz, 1H), 3.81 (dd, J=17.2, 5.68 Hz, 1H), 3.96 (dd, J=24.58, 11.16 Hz, 1H), 4.09 (dd, J=25.40, 12.76 Hz, 1H), 4.46 (dd, J=9.72, 4.13 Hz, 1H), 6.89 (br tr J=5.6 Hz), 7.13-7.73 (m, 2H).
LC-MS (I) R$_t$ 1.28 min, m/z 308.5 [M+H]$^+$ (94%).
MS (ESI) m/z 308.1 [M+H]$^+$

Step 7: (S)-tert-butyl 2-(2-cyano-4,4-difluoropyrrolidin-1-yl)-2-oxoethylcarbamate In a 50 mL round-bottomed flask (S)-tert-butyl 2-(2-carbamoyl-4,4-difluoropyrrolidin-1-yl)-2-oxoethylcarbamate (41) (0.720 g, 2.343 mmol) was dissolved in dry THF at −15° C. Then pyridine was added, followed by the dropwise addition of the solution of 2,2,2-trifluoroacetic anhydride (0.094 ml, 0.664 mmol) in 5 mL of DCM after the complete addition, the mixture was allowed to reach RT. The reaction mixture was stirred for 90 minutes. The reaction mixture was washed with 1M solution of aqueous solution of hydrochloric acid. Then the organic layer was washed three times with saturated sodium bicarbonate, brine, dried over sodium sulfate and evaporated. The crude mixture was purified using column chromatography (hexane-ethyl acetate 2-3) yielding a yellowish oil Yield: 0.678 g, 70%

$^1$H NMR (400 MHz, CDCl$_3$) δ 1.45 (s, 9H), 2.70-2.83 (m, 2H), 3.80-4.04 (m, 4H), 4.94-5.00 (m, 1H), 5.29 (br s, 1H).

LC-MS (I) R$_t$ 1.52 min, m/z 290.6 [M+H]$^+$ (94%).

MS (ESI) m/z 290.1 [M+H]$^+$

Step 8: (S)-1-(2-aminoacetyl)-4,4-difluoropyrrolidine-2-carbonitrile hydrochloride (S)-1-(2-aminoacetyl)-4,4-difluoropyrrolidine-2-carbonitrile trifluoroacetate To a cooled (0° C.) solution of (S)-tert-butyl 2-(2-cyano-4,4-difluoropyrrolidin-1-yl)-2-oxoethylcarbamate (7.3 g, 25.2 mmol), obtained from step 7, in 150 mL of ACN was added trifluoroacetic acid (38.9 mL, 0.505 mol) dropwise. The mixture was stirred overnight and the volatiles were evaporated. The residue was washed with ether.

(S)-1-(2-aminoacetyl)-4,4-difluoropyrrolidine-2-carbonitrile hydrochloride

The residue was stirred for 30 min at 0° C. in diethylether and dry HCl was bubbled in the reaction flask. A white solid precipitated out. The solid was collected via vacuum filtration and rinsed with cold ether and dried under vacuum to yield a whitish powder.

$^1$H NMR (400 MHz, D$_2$O): (5/1 mixture of trans/cis amide rotamers) δ 2.84-3.05 (m, 2H), 4.03-4.24 (m, 2H), 4.01 (s, 2H), 5.17 (dd, J=8.4, 4.1 Hz, 0.8H), 5.37 (d, J=8.4 Hz, 0.2H)

Yield: 70%

MS (ESI) m/z: 190.2 [M+H]$^+$

2.2 Synthesis of Final Products of Formula (I), Via Intermediates (D) and (E), as Defined in Scheme 1

Example 1

(S)—N-(2-(2-cyano-4,4-difluoropyrrolidin-1-yl)-2-oxoethyl)quinine-4-carboxamide

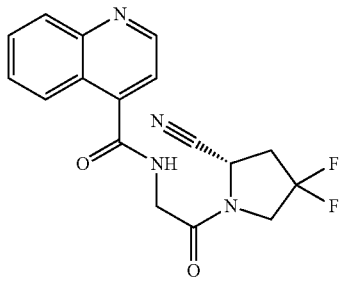 [SMILES: N#C[C@@H]1CC(F)(F)CN1C(=O)CNC(=O)c1ccnc2ccccc12]

Commercially available quinoline-4-carboxylic acid (0.065 g, 0.377 mmol) was dissolved in 7 ml of DMF, N-ethyl-N-isopropylpropan-2-amine (0.210 ml, 1.168 mmol), HOBT (0.058 g, 0.377 mmol) and TBTU (0.121 g, 0.377 mmol) were added. After 15 min a solution of (S)-1-(2-aminoacetyl)-4,4-difluoropyrrolidine-2-carbonitrile trifluoroacetate (0.085 g, 0.377 mmol) (prepared as described under A.2 of the experimental part) in DMF was added. The mixture was stirred overnight at room temperature. The volatiles were evaporated, the residue was dissolved in ethyl acetate and washed with 1 N citric acid, saturated sodium bicarbonate and brine. The solution was dried over sodium sulfate, filtrated and evaporated. It was purified using column chromatography (1-4 hexane-ethyl acetate). Yield: 64 mg, 45%

$^1$H NMR (400 MHz, CDCl$_3$): (8.5/1.5 mixture of trans/cis amide rotamers) δ 2.72-2.83 (m, 2H), 3.91-4.07 (m, 2H), 4.21 (dd, J=17.4, 4.2 Hz, 0.85H), 4.33 (dd, J=17.4, 4.3 Hz, 0.15H), 4.39 (dd, J=17.4, 5.6 Hz, 0.85H), 4.70 (dd, J=17.4, 5.7 Hz, 0.15H), 4.92-4.99 (m, 0.85H), 5.15 (d, J=9 Hz, 0.15H), 7.30 (s, 1H), 7.49 (dd, J=10.11, 4.30 Hz, 1H), 7.60 (dd, J=11.22, 4.11 Hz, 1H), 7.74 (t, J=7.69 Hz, 1H), 8.12 (d, J=8.42 Hz, 1H), 8.23 (t, J=9.99 Hz, 1H), 8.96-8.86 (m, 1H).

MS (ESI) m/z 345.0 [M+1]$^+$

LC-MS (I-B) R$_t$ 10.8 min, m/z 345.0 [M+H]$^+$ (98%).

Example 2

(S)—N-(2-(2-cyano-4,4-difluoropyrrolidin-1-yl)-2-oxoethyl)-1-naphthamide

Reference Compound No 1

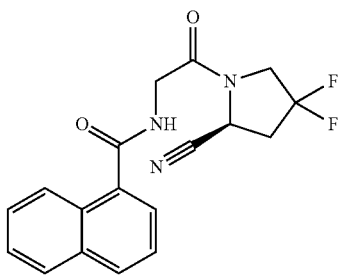 [SMILES: N#C[C@@H]1CC(F)(F)CN1C(=O)CNC(=O)c1cccc2ccccc12]

The title compound was prepared in a manner similar to that described in Example 1.

Yield: 43 mg, 36%

$^1$H NMR (400 MHz, CDCl3): δ 2.61-2.73 (m, 2H), 3.83-4.07 (m, 3H), 4.34 (dd, J=17.6, 6.0 Hz, 1H), 4.85-4.95 (m, 1H), 7.10 (t, J=5.6 Hz, 1H), 7.40 (dd, J=8.4 Hz, J=7.2 Hz, 1H), 7.50-7.57 (m, 2H), 7.65 (dd, J=7.0 Hz, J'=10 Hz, 1H), 7.86 (dd, J=7.2, 2.16 Hz, 1H), 7.90 (d, J=8.2 Hz, 1H), 8.32 (dd, J=7.52 Hz, J'=1.92 Hz, 1H)

LC-MS (I-B) R$_t$ 15.9 min, m/z 344.1 [M+H]$^+$ (97%)

Example 3

(S)—N-(2-(2-cyanopyrrolidine-1-yl)-2-oxoethyl)quinoline-4-carboxamide

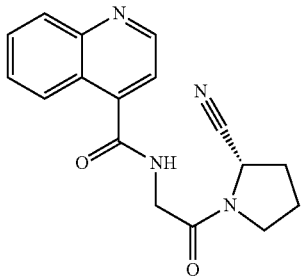 [SMILES: N#C[C@@H]1CCCN1C(=O)CNC(=O)c1ccnc2ccccc12]

Commercially available quinoline-4-carboxylic acid (0.078 g, 0.449 mmol) was dissolved in 7 ml of DMF, N-ethyl-N-isopropylpropan-2-amine (0.242 ml, 1.347 mmol), HOBT (0.069 g, 0.449 mmol) and TBTU (0.144 g, 0.449 mmol) were added. After 15 min a solution of (S)-1-(2-aminoacetyl)pyrrolidine-2-carbonitrile 2,2,2-trifluoroacetate (0.120 g, 0.449 mmol) (prepared as described under A.1 of the experimental part) in DMF was added. The mixture was stirred overnight at room temperature. The volatiles were evaporated, the residue was dissolved in ethyl acetate and extracted with 1 N citric acid, saturated sodium bicarbonate and brine. The solution was dried over sodium sulfate, filtrated and evaporated. It was purified using column chromatography (1-5 hexane-ethyl acetate).

Yield: 66 mg, 38%

$^1$H NMR (400 MHz, CDCl3): (8.5/1.5 mixture of trans/cis amide rotamers) δ 2.12-2.38 (m, 4H), 3.50-3.58 (m, 1H), 3.68-3.74 (m, 1H), 4.27 (dd, J=17.6, 4.1 Hz, 0.85H), 4.33 (dd, J=17.3, 4.3 Hz, 0.15H), 4.43 (dd, J=18.0, 5.0 Hz, 0.85H), 4.60 (dd, J=17.3, 5.4 Hz, 0.15H), 4.75-4.78 (m, 1H), 7.14 (br s, 1H), 7.49 (d, J=6 Hz, 1H), 7.62 (d tr, J=7.7 Hz, J=1.3 Hz, 1H), 7.77 (d tr, J=7.6, 1.4 Hz, 1H), 8.15 (d, J=8.49 Hz, 1H), 8.28 (dd, J=8.07, 0.79 Hz, 1H), 8.95 (d, J=4.3 Hz, 1H)

MS (ESI) m/z 331.1 [M+Na]$^+$

LC-MS (I-B) R$_t$ 9.7 min, m/z 309.0 [M+H]$^+$ (97%).

Example 4

(S)—N-(2-(2-cyanopyrrolidine-1-yl)-2-oxoethyl)-2-methylquinoline-4-carboxamide

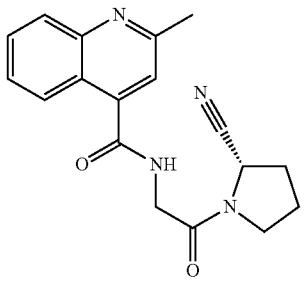 [SMILES: Cc1cc(C(=O)NCC(=O)N2CCC[C@H]2C#N)c2ccccc2n1]

The title compound was prepared in a manner similar to that described in Example 3, using commercially available 2-methylquinoline-4-carboxylic acid.

Yield: 58 mg, 37%

$^1$H NMR (400 MHz, CDCl$_3$): (8.5/1.5 mixture of trans/cis amide rotamers) δ 2.23-2.41 (m, 4H), 2.78 (s, 3H), 3.53-3.58 (m, 1H), 3.68-3.74 (m, 1H), 4.26 (dd, J=18.0, 4.1 Hz, 0.85H), 4.33 (dd, J=18.0, 4.3 Hz, 0.15H), 4.42 (dd, J=18.0, 5.1 Hz, 0.85H), 4.60 (dd, J=18.0, 5.4 Hz, 0.15H), 4.76 (d, J=9 Hz, 0.15H), 4.78-4.83 (m, 0.85H), 7.02 (br s, 1H), 7.43 (s, 1H), 7.55 (tr, J=7.7 Hz, 1H), 7.74 (d tr, J=7.6, 1.4 Hz, 1H), 8.06 (br d, J=8.0 Hz, 1H), 8.28 (br d, J=8.3 Hz, 1H), 8.95 (d, J=4.3 Hz, 1H)

MS (ESI) m/z 323.1 [M+H]$^+$

LC-MS (I-B) R$_t$ 8.5 min, m/z 323.1 [M+H]$^+$ (95%).

Example 5

(S)—N-(2-(2-cyanopyrrolidine-1-yl)-2-oxoethyl)quinoline-3-carboxamide

Reference Compound No 3

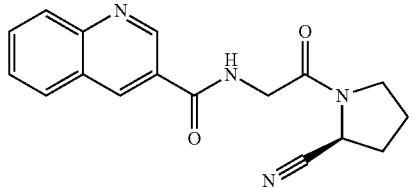 [SMILES: N#C[C@@H]1CCCN1C(=O)CNC(=O)c1cnc2ccccc2c1]

The title compound was prepared in a manner similar to that described in Example 3, using commercially available quinoline-3-carboxylic acid.

Yield: 47 mg, 36%

$^1$H NMR (400 MHz, CDCl3): (9/1 mixture of trans/cis amide rotamers) δ 2.18-2.39 (m, 4H), 3.50-3.59 (m, 1H), 3.70-3.78 (m, 1H), 4.18 (dd, J=17.7, 3.6 Hz, 0.9H), 4.26 (dd, J=17.7, 3.6 Hz, 0.1H), 4.35 (dd, J=18.0, 4.3 Hz, 0.1H), 4.56 (dd, J=17.7, 6.0 Hz, 0.9H), 4.77-4.82 (m, 1H), 7.56 (d tr, J=7.5, 1.1 Hz, 1H), 7.73-7.79 (m, 2H), 7.96 (br_s, 1H), 8.05 (br_d, J=8.0 Hz, 1H), 8.53 (d, J=2.0 Hz, 1H), 9.23 (d, J=2.0 Hz, 1H)

MS (ESI) m/z 331.1 [M+Na]$^+$

LC-MS (I-B) R$_t$ 11.2 min, m/z 309.1 [M+H]$^+$ (98%).

Example 6

(S)—N-(2-(2-cyanopyrrolidine-1-yl)-2-oxoethyl)isonicotinamide

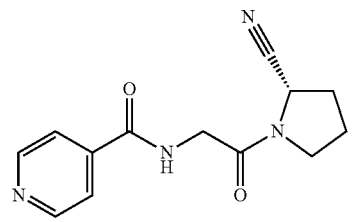 [SMILES: N#C[C@@H]1CCCN1C(=O)CNC(=O)c1ccncc1]

The title compound was prepared in a manner similar to that described in Example 3 using pyridine-4-carboxylic acid.

Yield: 41 mg, 34%

$^1$H NMR (400 MHz, CDCl$_3$): δ 2.13-2.36 (m, 4H), 3.45-3.54 (m, 1H), 3.66-3.74 (m, 1H), 4.05-4.12 (m, 1H), 4.46-4.53 (m, 1H), 4.72-4.76 (m, 1H), 7.61 (d, J=6 Hz, 2H), 8.63 (d, J=6 Hz, 2H)

MS (ESI) m/z 259.1 [M+H]$^+$

LC-MS (I-B) R$_t$ 3.7 min, m/z 259.1 [M+H]$^+$ (96%)

Example 7

(S)—N-(2-(2-cyanopyrrolidine-1-yl)-2-oxoethyl)quinoline-8-carboxamide

Reference Compound No 6

The title compound was prepared in a manner similar to that described in Example 3 using quinoline-8-carboxylic acid.

Yield: 39 mg, 48%

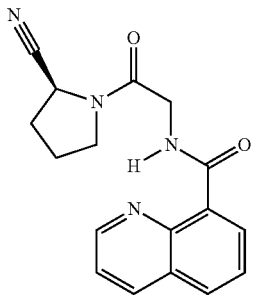 [SMILES: N#C[C@@H]1CCCN1C(=O)CNC(=O)c1cccc2cccnc12]

$^{1}$H NMR (400 MHz, CDCl$_{3}$): (9/1 mixture of trans/cis amide rotamers) δ 2.08-2.41 (m, 4H), 3.66-3.55 (m, 1H), 3.71-3.79 (m, 1H), 4.36 (dd, J=17.8, 4.2 Hz, 1H), 4.50-4.62 (dd, J=17.8, 5.1 Hz, 0.9H), 4.72 (dd, J=18.0, 4.2 Hz, 0.1H), 4.86 (br_d, J=6.2 Hz, 1H), 5.03 (d, J=7 Hz, 0.1H), 7.51 (dd, J=8.3, 4.3 Hz, 1H), 7.68 (t, J=8 Hz 1H), 7.99 (dd, J=8.1, 1.5 Hz, 1H), 8.28 (dd, J=8.3, 1.8 Hz, 1H), 8.84 (dd, J=7.4, 1.6 Hz, 1H), 9.06 (dd, J=4.3, 1.8 Hz, 1H), 11.97-12.07 (br_s, 1H).

UPLC I (ESI) R$_{t}$ 1.31 min, m/z 309.5 [M+H]$^{+}$ (96%).

Example 8

(S)—N-(2-(2-cyanopyrrolidine-1-yl)-2-oxoethyl)-3-hydroxy-2-methylquinoline-4-carboxamide hydrochloride The title compound was prepared in a manner similar to that described in Example 3 using 3-hydroxychinaldin-4-carboxylic acid.

Yield: 28 mg, 29%

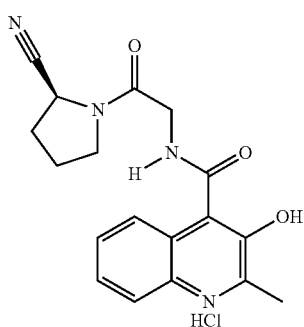 [SMILES: Cc1nc2ccccc2c(C(=O)NCC(=O)N2CCC[C@H]2C#N)c1O ; Cl]

$^{1}$H NMR (400 MHz, MeOD): δ 2.19-2.39 (m, 4H), 2.95 (s, 3H), 3.64-3.68 (m, 1H), 3.79-3.88 (m, 1H), 4.44 (d, J=5.8 Hz, 2H), 4.86-4.90 (m, 1H), 7.84-7.98 (m, 2H), 8.10 (d, J=7.9 Hz, 1H), 8.30 (d, J=7.5 Hz, 1H).

UPLC I (ESI) R$_{t}$ 1.11 min, m/z 339.6 [M+H]$^{+}$ (95%).

Example 9

(S)—N-(2-(2-Cyanopyrrolidine-1-yl)-2-oxoethyl)-6-fluoroquinoline-4-carboxamide

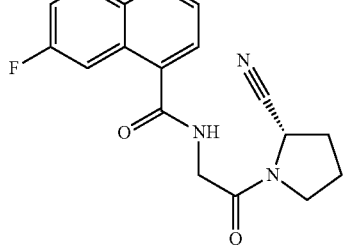

This compound was prepared relying on the general approach, consisting of coupling an intermediate of formula (D) and a non-commercially available intermediate of formula (E). The latter was obtained from a Pfitzinger-type reaction on a commercially available isatin ('step1'), followed by decarboxylation of the quinoline dicarboxylate product of the Pfitzinger-type reaction. This approach is summarized in Scheme 5.

Scheme 5. Synthesis of compounds of formula (I) involving a Pfitzinger-type condensation/decarboxylation.

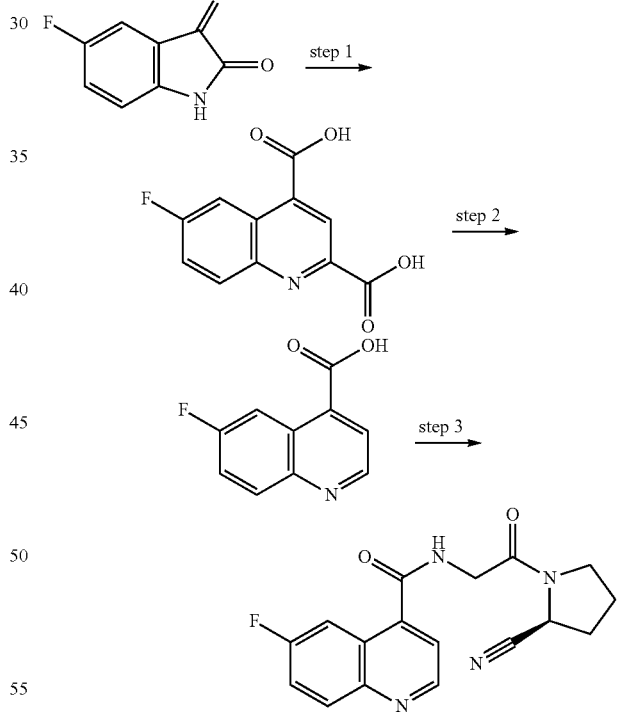

Step 1: 6-Fluoroquinoline-2,4-dicarboxylic acid

To 5-fluoroindoline-2,3-dione (0.454 g, 2.75 mmol) was a 3M NaOH (5.46 mL, 16.52 mmol) solution added. The reaction mixture was heated until refluxing, and 2-oxopropanoate (0.364 g, 3.30 mmol) was added. After refluxing at 110° C. for 4 h, the mixture was cooled to room temperature. The pH was adjusted to 3-4 with 1M HCl, and the precipitate was filtered and washed with water to yield whitish crystals Yield: 0.453 g, 70%
¹H NMR (400 MHz, DMSO-d₆): δ 7.89 (ddd, J=9.27, 8.15, 2.92 Hz, 1H), 8.35 (dd, J=9.33, 5.81 Hz, 1H), 8.57 (s, 1H), 8.60 (dd, J=11.05, 2.86 Hz, 1H).
MS (ESI) m/z 236.1 [M+H]⁺.

Step 2: 6-Fluoroquinoline-4-carboxylic acid

6-Fluoroquinoline-2,4-dicarboxylic acid (0.103 g, 0.437 mmol) was transferred in a pressure tube, 6 mL water was added. The closed tube was heated to 200° C. for 4 h. After slow cooling of the tube, the resulting precipitate was filtered and washed with water to yield white crystals
Yield: 0.076 g, 90%
¹H NMR (400 MHz, DMSO-d₆): δ 7.79 (ddd, J=9.24, 8.20, 2.94 Hz, 1H), 8.03 (d, J=4.31 Hz, 1H), 8.21 (dd, J=5.86 Hz, J=9.27 Hz, 1H), 8.52 (dd, J=11.19, 2.90 Hz, 1H), 9.05 (d, J=4.38 Hz, 1H).
MS (ESI) m/z 192.1 [M+H]⁺, 189.9 [M−H].

Step 3: (S)—N-(2-(2-Cyanopyrrolidine-1-yl)-2-oxo-ethyl)-6-fluoroquinoline-4-carboxamide 6-Fluoroquinoline-4-carboxylic acid (17) (0.054 g, 0.282 mmol) was dissolved in a 1:1 mixture of dry DCM and THF (5 mL). 1-chloro-N,N,2-trimethylprop-1-en-1-amine (0.052 mL, 0.395 mmol) was added to this solution, and the mixture was stirred for 30 minutes at rt. Then, a solution of (S)-1-(2-aminoacetyl)pyrrolidine-2-carbonitrile 2,2,2-trifluoroacetate (0.075 g, 0.282 mmol) prepared as described in general procedure B and triethylamine (80 µL, 0.571 mmol) in 3 mL dry THF was added, and the mixture was stirred for 2 h. After evaporation of volatiles, the residue was dissolved in DCM (15 mL), washed with saturated sodium bicarbonate and brine. The organic layer was dried over sodium sulfate, filtrated and purified using flash chromatography (95-5 ethyl acetate-methanol) to yield white crystals
Yield: 0.019 g, 20%
¹H NMR (400 MHz, CDCl₃) (9/1 mixture of trans/cis amide rotamers) δ 2.21-2.41 (m, 4H), 3.57 (m, 1H), 3.73 (m, 1H), 4.27 (dd, J=17.81, 3.90 Hz, 1H), 4.42 (dd, J=17.86, 4.81 Hz, 1H), 4.73 (d, J=8.8 Hz, 0.1H), 4.81 (m, 0.9H), 7.06 (br_s, 1H), 7.51-7.56 (m, 1H), 7.56-7.59 (m, 1H), 8.01 (dd, J=10.00, 2.81 Hz, 1H), 8.17 (dd, J=9.25, 5.45 Hz, 1H), 8.95 (d, J=4.36 Hz, 1H).
UPLC I (ESI) R_t 1.29 min, m/z 325.3 [M−H]⁺ (100%).
MS (ESI) m/z 327.2 [M+H]⁺.

Example 10

(S)-6-Chloro-N-(2-(2-cyanopyrrolidine-1-yl)-2-oxo-ethyl)quinoline-4-carboxamide

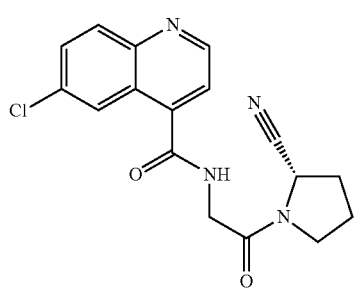 [SMILES: N#C[C@@H]1CCCN1C(=O)CNC(=O)c1ccnc2ccc(Cl)cc12]

The title compound was prepared in a manner similar to that described in Example 9

Step 1: 6-Chloroquinoline-2,4-dicarboxylic acid

¹H NMR (400 MHz, DMSO-d₆): δ 7.82 (dd, J=9.0, 2.4 Hz, 1H), 8.20 (d, J=9.0 Hz, 1H), 8.37 (s, 1H), 9.01 (d, J=2.3 Hz, 1H).
MS (ESI) m/z 252.6 [M+H]⁺.

Step 2: 6-Chloroquinoline-4-carboxylic acid

¹H NMR (400 MHz, DMSO-d₆): δ 7.57 (d, J=4.32 Hz, 1H), 7.66 (dd, J=8.96, 2.53 Hz, 1H), 7.95 (d, J=8.99 Hz, 1H), 8.80 (d, J, 4.33 Hz, 1H), 8.96 (d, J=2.47 Hz, 1H).
MS (ESI) m/z 205.8 [M−H]⁺.

Step 3: (S)-6-Chloro-N-(2-(2-cyanopyrrolidine-1-yl)-2-oxoethyl)quinoline-4-carboxamide Yield: 0.011 g, 10%.
¹H NMR (400 MHz, CDCl₃): δ 2.24-2.44 (m, 4H), 3.59 (m, 1H), 3.75 (m, 1H), 4.31 (dd, J=17.95, 3.96 Hz, 1H), 4.45 (dd, J=17.89, 4.76 Hz, 1H), 4.83 (m, 1H), 7.07 (br_s, 1H), 7.59 (d, J=4.32 Hz, 1H), 7.74 (dd, J=9.00, 2.33 Hz, 1H), 8.12 (d, J=8.98 Hz, 1H), 8.36 (d, J=2.23 Hz, 1H), 9.00 (d, J=4.34 Hz, 1H).
UPLC I (ESI) R_t 1.41 min, m/z 343.5 [M+H]⁺ (95%).
MS (ESI) m/z 343.5 [M+H]⁺.

Example 11

(S)—N-(2-(2-Cyanopyrrolidine-1-yl)-2-oxoethyl)-6-(trifluoromethoxy)quinoline-4-carboxamide

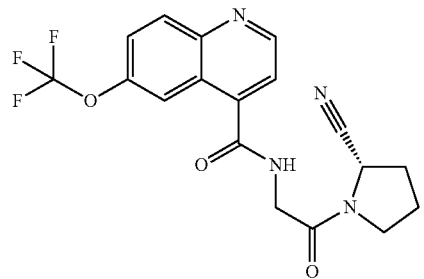 [SMILES: N#C[C@@H]1CCCN1C(=O)CNC(=O)c1ccnc2ccc(OC(F)(F)F)cc12]

The title compound was prepared in a manner similar to that described in Example 9

Step 1: 6-(Trifluoromethoxy)quinoline-2,4-dicarboxylic acid

Yield: 0.190 g, 73%
¹H NMR (400 MHz, DMSO-d₆): δ 7.95 (d, J=9.38 Hz, 1H), 8.41 (d, J=9.23 Hz, 1H), 8.58 (s, 1H), 8.96 (s, 1H).
MS (ESI) m/z 323.9 [M+Na]⁺

Step 2: 6-(Trifluoromethoxy)quinoline-4-carboxylic acid

Yield: 0.132 g, 86%
¹H NMR (400 MHz, DMSO-d₆): δ 7.64 (d, J=5.3 Hz, 1H), 8.01 (dd, J=2.80 Hz, J=9.0 Hz, 1H), 8.27 (d, J=8.8 Hz 1H), 8.74 (d, J=4.5 Hz 1H), 9.03 (d, J=2.8 Hz, 1H).
MS (ESI) m/z 258.0 [M+H]⁺, 255.7 [M−H]⁺.

Step 3: (S)—N-(2-(2-Cyanopyrrolidine-1-yl)-2-oxo-ethyl)-6-(trifluoromethoxy)quinoline-4-carboxamide Yield: 0.015 g, 15%
¹H NMR (400 MHz, CDCl₃): (9/1 mixture of trans/cis amide rotamers) δ 2.20-2.42 (m, 4H), 3.57 (m, 1H), 3.7 (m, 1H), 4.30 (dd, J=17.9, 3.9 Hz, 1H), 4.43 (dd, J=17.9, 4.8 Hz, 1H), 4.74 (d, J=8.8 Hz, 0.1H), 4.81 (m, 0.9H), 7.20 (br_s, 1H), 7.70-7.74 (m, 1H), 7.75 (d, J=4.6 Hz, 1H), 8.28 (s, 1H), 8.34 (d, J=9.3 Hz, 1H), 9.11, (d, J=4.6 Hz, 1H). UPLC I (ESI) R$_t$ 1.57 min, m/z 393.5 [M+H]⁺ (100%).
MS (ESI) m/z 393.5 [M+H]⁺.

Example 12

(S)-8-Chloro-N-(2-(2-cyanopyrrolidine-1-yl)-2-oxo-ethyl)quinoline-4-carboxamide

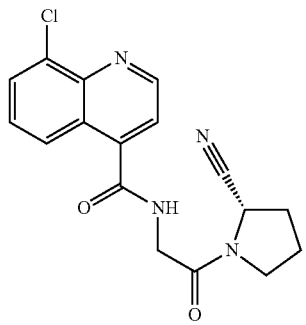

The title compound was prepared in a manner similar to that described in Example 9

Step 1: 8-Chloroquinoline-2,4-dicarboxylic acid

Yield: 0.188 g, 68%
¹H NMR (400 MHz, DMSO-d₆): δ7.70 (dd, J=8.4, 8.04 Hz, 1H), 8.11 (dd, J=8.04, 1.8 Hz, 1H), 8.70 (ddd, J=8.04, 2.63, 1.8 Hz, 1H), 8.74 (d, J=2.63 Hz, 1H).
MS (ESI) m/z 273.9 [M+Na]⁺.

Step 2: 8-Chloroquinoline-4-carboxylic acid

Yield: 0.081 g, 54%
¹H NMR (400 MHz, DMSO-d₆): δ 7.71 (dd, J=8.58, 7.57 Hz, 1H), 8.03 (d, J=4.34 Hz, 1H), 8.06 (dd, J=7.53, 1.21 Hz, 1H), 8.67 (dd, J=8.62, 1.22 Hz, 1H), 9.16 (d, J=4.34 Hz, 1H).
MS (ESI) m/z 208.5 [M+H]⁺.

Step 3: (S)₈-Chloro-N-(2-(2-cyanopyrrolidine-1-yl)-2-oxoethyl)quinoline-4-carboxamide Yield: 0.019 g, 20%
¹H NMR (400 MHz, CDCl₃): (9/1 mixture of trans/cis amide rotamers) δ 2.32 (m, 4H), 3.56 (m, 1H), 3.73 (m, 1H), 4.29 (dd, J=17.9, 3.9 Hz, 1H), 4.41 (dd, J=17.81, 4.83 Hz, 1H), 4.69 (d, J=8.8 Hz, 0.1H), 4.81 (m, 0.9H), 7.02 (br s, 1H), 7.54-7.58 (m, 1H), 7.62 (d, J=4.3 Hz, 1H), 7.92 (dd, J=7.5, 1.2 Hz, 1H), 8.24 (dd, J=8.5, 1.2 Hz, 1H), 9.12 (d, J=4.30 Hz, 1H). UPLC I (ESI) R$_t$ 1.36 min, m/z 343.8 [M+H]⁺ (96%).
MS (ESI) m/z 343.8 [M+H]⁺.

Example 13

(S)-8-Bromo-N-(2-(2-cyanopyrrolidine-1-yl)-2-oxo-ethyl)quinoline-4-carboxamide

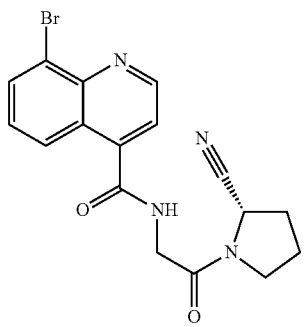 [SMILES: N#C[C@@H]1CCCN1C(=O)CNC(=O)c1ccnc2c(Br)cccc12]

The title compound was prepared in a manner similar to that described in Example 9
Step 1
Yield: 0.350 g, 85%
¹H NMR (400 MHz, DMSO-d₆): δ 7.70-7.74 (m, 1H), 8.29-8.31 (m, 1H), 8.50 (s, 1H), 8.79-8.81 (dd, J=8.6, 1.2 Hz, 1H), 14.02 (s, 2H)
MS (ESI) m/z 297.3 [M+H]+
Step 2
Yield: 0.210 g, 90%
¹H NMR (400 MHz, CDCl₃): δ 8.04 (s, 1H), 8.15 (d, J=7.52 Hz, 1H), 8.70 (s, 1H), 8.87 (d, J=8.61 Hz, 1H), 9.20 (d, J=4.39 Hz, 1H)
MS (ESI) m/z 253.4 [M+H]+

(S)-8-Bromo-N-(2-(2-cyanopyrrolidine-1-yl)-2-oxo-ethyl)quinoline-4-carboxamide

Yield: 0.011 g, 12%.
¹H NMR (400 MHz, CDCl₃): (9/1 mixture of trans/cis amide rotamers) δ 2.16-2.45 (m, 4H), 3.59 (m, 1H), 3.75 (m, 1H), 4.31 (dd, J=17.85, 4.01 Hz, 1H), 4.44 (dd, J=17.86, 4.80 Hz, 1H), 4.72 (d, J=7.1 Hz, 0.1H), 4.83 (d, J=5.15 Hz, 0.9H), 7.04 (br s, 1H), 7.52 (dd, J=13.81, 6.28 Hz, 1H), 7.63 (d, J=4.30 Hz, 1H), 8.16 (dd, J=7.49, 1.21 Hz, 1H), 8.31 (dd, J=8.47, 1.20 Hz, 1H), 9.14 (d, J=4.29 Hz, 1H).
UPLC I (ESI) R$_t$ 1.39 min, m/z 386.2 [M+H]⁺ (100%).
MS (ESI) m/z 388.1 [M+H]⁺.

Example 14

(S)—N-(2-(2-cyanopyrrolidine-1-yl)-2-oxoethyl)-6-methoxyquinoline-4-carboxamide

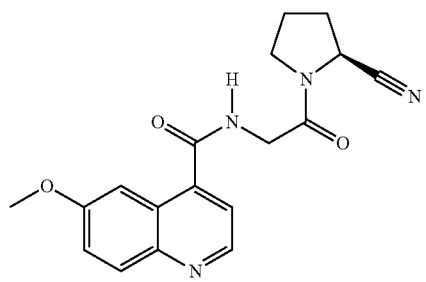 [SMILES: COc1ccc2nccc(C(=O)NCC(=O)N3CCC[C@H]3C#N)c2c1]

The title compound was prepared in a manner similar to that described in Example 9

Step 1: 6-methoxyquinoline-2,4-dicarboxylic acid $^1$H NMR (400 MHz, DMSO-d$_6$): δ 3.95 (s, 3H), 7.57-7.63 (dd, J=9.3, 2.8 Hz, 1H), 8.13-8.19 (d, J=9.2 Hz, 1H), 8.24-8.29 (d, J=2.8 Hz, 1H), 8.47-8.54 (s, 1H)
UPLC I (ESI) R$_t$ 1.01 min, m/z 248.5 [M+H]$^+$ (99%).

Step 2: 6-methoxyquinoline-4-carboxylic acid

The starting material was reacted in a pressured tube for 1.5 hour at 200° C. with stirring. And worked up as described in example 9.
1H NMR (400 MHz, DMSO-d$_6$): δ 3.85-3.96 (s, 3H), 7.45-7.55 (dd, J=9.0, 3.0 Hz, 1H), 7.88-7.99 (d, J=4.5 Hz, 1H), 7.99-8.08 (d, J=9.2 Hz, 1H), 8.13-8.23 (d, J=3.0 Hz, 1H), 8.83-8.92 (d, J=4.5 Hz, 1H).
UPLC I (ESI) R$_t$ 0.44 min, m/z 204.5 [M+H]$^+$ (99%).

Step 3: (S)—N-(2-(2-cyanopyrrolidine-1-yl)-2-oxo-ethyl)-6-methoxyquinoline-4-carboxamide Yield: 32 mg, 34%
$^1$H NMR (400 MHz, CDCl3) δ 2.22-2.42 (m, 4H), 3.51-3.60 (m, 1H), 3.70-3.78 (m, 1H), 3.93-3.99 (s, 3H), 4.28-4.36 (dd, J=17.8, 4.2 Hz, 1H), 4.36-4.44 (dd, J=17.9, 4.7 Hz, 1H), 4.77-4.82 (m, 1H), 7.01-7.07 (s, 1H), 7.39-7.44 (dd, J=9.2, 2.8 Hz, 1H), 7.49-7.53 (d, J=4.4 Hz, 1H), 7.66-7.70 (d, J=2.8 Hz, 1H), 8.01-8.07 (d, J=9.2 Hz, 1H), 8.79-8.85 (d, J=4.4 Hz, 1H).
UPLC I (ESI) R$_t$ 1.18 min, m/z 339.7 [M+H]$^+$ (95%).

Example 15

(S)-7-bromo-N-(2-(2-cyanopyrrolidine-1-yl)-2-oxo-ethyl)quinoline-4-carboxamide

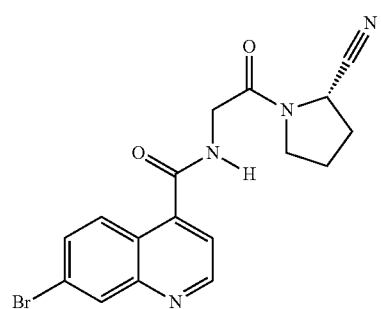 [SMILES: N#C[C@@H]1CCCN1C(=O)CNC(=O)c1ccnc2cc(Cl)ccc12]

The title compound was prepared in a manner similar to that described in Example 9

Step 1: 7-bromoquinoline-2,4-dicarboxylic acid $^1$H NMR (400 MHz, DMSO-d$_6$): δ 7.90-8.04 (dd, J=9.1, 2.1 Hz, 1H), 8.40-8.53 (m, 2H), 8.74-8.79 (d, J=9.2 Hz, 1H)
UPLC I (ESI) R$_t$ 1.27 min, m/z 296.8, 298.8 [M+H]$^+$ (99%).

Step 2: 7-bromo-4-quinoline-carboxylic acid

The starting material was reacted in a pressured tube for 50 min at 200° C. with stirring. And worked up as described in example 9

$^1$H NMR (400 MHz, DMSO-d$_6$): δ 7.54-7.60 (d, J=4.4 Hz, 1H), 7.69-7.75 (dd, J=8.4, 7.5 Hz, 1H), 7.98-8.05 (dd, J=7.6, 1.2 Hz, 1H), 8.07-8.16 (dd, J=8.4, 1.2 Hz, 1H), 8.91-9.01 (d, J=4.3 Hz, 1H).
UPLC I (ESI) R$_t$ 1.19 min, m/z 252.4, 254.4 [M+H]$^+$ (99%).

Step 3: (S)-7-bromo-N-(2-(2-cyanopyrrolidine-1-yl)-2-oxoethyl)quinoline-4-carboxamide Yield: 33 mg, 54%
$^1$H NMR (400 MHz, CDCl$_3$): (9/1 mixture of trans/cis amide rotamers) δ 2.11-2.40 (m, 4H), 3.48-3.58 (m, 1H), 3.65-3.74 (ddd, J=9.8, 7.4, 3.0 Hz, 1H), 4.20-4.29 (dd, J=17.8, 4.0 Hz, 1H), 4.28-4.34 (dd, J=17.8 Hz, J=4.1 Hz, 0.1H), 4.32-4.42 (dd, J=17.8, 4.8 Hz, 1H), 4.52-4.58 (dd, J=17.5 Hz, J=5.3 Hz, 0.1H), 4.70 (d, J=8.0 Hz, 0.1H), 4.74-4.80 (m, 0.9H), 7.01-7.07 (m, 1H), 7.50-7.55 (d, J=4.4 Hz, 1H), 7.65-7.71 (dd, J=9.0, 2.0 Hz, 1H), 8.15-8.22 (d, J=9.0 Hz, 1H), 8.29-8.34 (d, J=2.0 Hz, 1H), 8.93-8.97-(d, J=4.3 Hz, 1H).
$^{13}$C NMR (101 MHz, CDCl3) δ 166.84, 166.74, 150.88, 149.41, 140.77, 132.24, 131.39, 126.77, 124.46, 123.16, 119.05, 117.71, 46.75, 45.63, 42.50, 29.95, 25.09.
UPLC I (ESI) R$_t$ 1.44 min, m/z 386.4, 389.4 [M+H]$^+$ (99%).

Example 16

(S)-7-chloro-N-(2-(2-cyanopyrrolidine-1-yl)-2-oxo-ethyl)quinoline-4-carboxamide

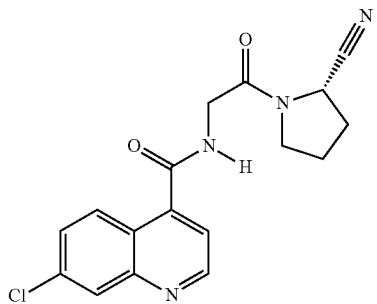

The title compound was prepared in a manner similar to that described in Example 9

Step 1: 7-chloroquinoline-2,4-dicarboxylic acid $^1$H NMR (400 MHz, DMSO-d$_6$): δ 7.85-7.92 (dd, J=9.1, 2.3 Hz, 1H), 8.28-8.33 (d, J=2.3 Hz, 1H), 8.45-8.53 (s, 1H), 8.82-8.89 (d, J=9.2 Hz, 1H).
UPLC I (ESI) R$_t$ 1.24 min, m/z 252.3 [M+H]$^+$ (96%).

Step 2: 7-chloroquinoline-4-carboxylic acid

The starting material was reacted in a pressured tube for 1.5 hour at 200° C. with stirring. And worked up as described in example 9.
$^1$H NMR (400 MHz, DMSO-d$_6$): δ 7.74-7.83 (dd, J=9.2, 2.3 Hz, 1H), 7.93-8.02 (d, J=4.4 Hz, 1H), 8.15-8.24 (d, J=2.3 Hz, 1H), 8.71-8.83 (d, J=9.1 Hz, 1H), 9.06-9.15 (d, J=4.4 Hz, 1H), 13.34-14.27 (br s, 1H).
UPLC I (ESI) R$_t$ 1.15 min, m/z 208.4 [M+H]$^+$ (98%).

Step 3: (S)-7-chloro-N-(2-(2-cyanopyrrolidine-1-yl)-2-oxoethyl)quinoline-4-carboxamide Yield: 43 mg, 62%

$^1$H NMR (400 MHz, DMSO-$d_6$): (9/1 mixture of trans/cis amide rotamers) δ 1.92-2.34 (m, 4H), 3.50-3.59 (td, J=9.0, 6.8 Hz, 1H), 3.70-3.78 (ddd, J=9.4, 7.6, 3.7 Hz, 1H), 4.14-4.22 (dd, J=17.0, 5.7 Hz, 1H), 4.22-4.30 (dd, J=17.0, 6.2 Hz, 0.9H), 4.36-4.42 (dd, J=16.8, 5.8 Hz, 0.1H), 4.83-4.88 (dd, J=7.3, 3.6 Hz, 0.9H), 5.28-5.30 (dd, J=7.0, 2.4 Hz, 0.1H), 7.59-7.65 (d, J=4.3 Hz, 1H), 7.72-7.79 (dd, J=9.0, 2.3 Hz, 1H), 8.13-8.21 (d, J=2.2 Hz, 1H), 8.38-8.45 (d, J=8.9 Hz, 1H), 9.02-9.07 (d, J=4.3 Hz, 1H), 9.11-9.17 (t, J=5.9 Hz, 1H).

$^{13}$C NMR (101 MHz, CDCl3) δ 166.89, 166.76, 150.94, 149.21, 140.69, 136.16, 128.88 (2-carbon atoms), 126.78, 122.88, 118.92, 117.72, 46.75, 45.63, 42.50, 29.95, 25.09.

UPLC I (ESI) $R_t$ 1.40 min, m/z 343.6 [M+H]$^+$ (99%).

Example 17

(S)—N-(2-(2-cyanopyrrolidine-1-yl)-2-oxoethyl)quinoline-5-carboxamide

Reference Compound No 7

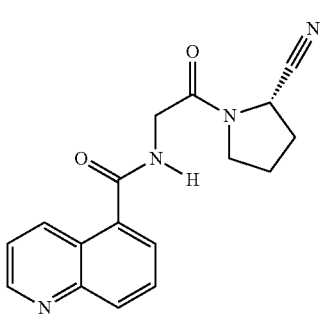 [SMILES: N#C[C@@H]1CCCN1C(=O)CNC(=O)c1cccc2ncccc12]

The title compound was prepared in a manner similar to that described in Example 3 starting from the commercially available quinoline-5-carboxylic acid Yield: 24 mg, 40%

$^1$H NMR (400 MHz, CDCl$_3$): (9/1 mixture of trans/cis amide rotamers) δ 2.12-2.43 (m, 4H), 3.52-3.60 (td, J=8.5, 6.1 Hz, 1H), 3.68-3.77 (ddd, J=9.6, 7.1, 2.8 Hz, 1H), 4.21-4.31 (dd, J=17.8, 4.0 Hz, 1H), 4.37-4.46 (dd, J=17.8, 4.9 Hz, 0.9H), 4.56-4.63 (dd, J=17.2, 5.6 Hz, 0.1H), 4.76-4.83 (m, 1H), 6.98-7.01 (s, OH), 7.01-7.10 (s, 1H), 7.45-7.50 (dd, J=8.6, 4.1 Hz, 1H), 7.67-7.74 (m, 1H), 7.78-7.84 (dd, J=7.2, 1.4 Hz, 1H), 8.18-8.26 (m, 1H), 8.76-8.85 (dt, J=8.5, 1.3 Hz, 1H), 8.93-9.00 (dd, J=4.1, 1.7 Hz, 1H).

UPLC I (ESI) $R_t$ 0.94 min, m/z 309.6 [M+H]$^+$ (98%).

Example 18

(S)—N-(2-(2-cyanopyrrolidine-1-yl)-2-oxoethyl)-2-phenylisonicotinamide

The title compound is prepared as described in scheme 2b

Step 1: 2-phenylisonicotinic acid 2-bromoisonicotinic acid (0.210 g, 1.040 mmol) was dissolved in degassed DME (Volume: 8 ml) under nitrogen. Tetrakis(triphenylphosphine)palladium(0) (0.060 g, 0.052 mmol) was added, the resulting reaction mixture was stirred for 15 min. Then aqueous potassium carbonate (4.16 ml, 8.32 mmol) and phenylboronic acid (0.171 g, 1.403 mmol) were added subsequently. The resulting RM was refluxed at 95° C. for 18 h and then cooled to rt. After filtration over celite the reaction mixture was acidified to pH 3-4 and the white precipitate was filtered off and washed with water This resulted in a white powder after recrystallization from 2-methoxyethanol.

Yield: 0.106 g, 57%.

$^1$H NMR (400 MHz, DMSO-$d_6$): δ 7.44-7.60 (m, 3H), 7.71-7.86 (dd, J=4.9, 1.5 Hz, 1H), 8.05-8.19 (m, 2H), 8.23-8.35 (t, J=1.2 Hz, 1H), 8.79-8.93 (dd, J=5.1, 0.8 Hz, 1H), 13.56-13.97 (s, 1H).

UPLC I (ESI) $R_t$ 1.37 min, m/z 200.5 [M+H]$^+$ (92%).

Step 2: (S)—N-(2-(2-cyanopyrrolidine-1-yl)-2-oxoethyl)-2-phenylisonicotinamide

Yield: 0.037 g, 52%.

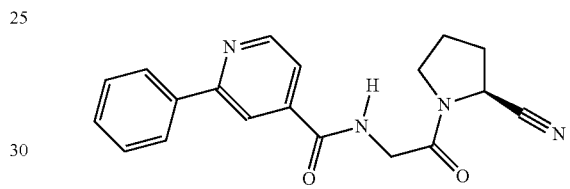

$^1$H NMR (400 MHz, CDCl$_3$): (9/1 mixture of trans/cis amide rotamers) δ 2.15-2.43 (m, 4H), 3.49-3.58 (td, J=8.6, 7.6, 5.9 Hz, 1H), 3.67-3.75 (ddd, J=14.9, 8.4, 4.0 Hz, 1H), 4.17-4.26 (dd, J=18.0, 3.7 Hz, 1H), 4.31-4.40 (dd, J=18.0, 4.7 Hz, 0.9H), 4.46-4.53 (dd, J=17.6, 5.2 Hz, 0.1H), 4.71-4.75 (d, J=8.3 Hz, 0.1H), 4.77-4.83 (dd, J=8.0, 2.4 Hz, 0.9H), 7.36-7.41 (s, 1H), 7.42-7.53 (m, 3H), 7.56-7.60 (dd, J=5.0, 1.6 Hz, 1H), 8.02-8.07 (m, 2H), 8.10-8.13 (dd, J=1.6, 0.9 Hz, 1H), 8.79-8.83 (dd, J=5.0, 0.9 Hz, 1H)

UPLC I (ESI) $R_t$ 1.45 min, m/z 335.6 [M+H]$^+$ (98%).

Example 19

(S)—N-(2-(2-cyanopyrrolidine-1-yl)-2-oxoethyl)-2-(3,4-dimethoxyphenyl)isonicotinamide Yield: 0.130 g, 49%.

The title compound was prepared in a manner similar to that described in Example 14.

Step 1: 2-(3,4-dimethoxyphenyl)isonicotinic acid $^1$H NMR (400 MHz, DMSO-$d_6$): δ 3.78-3.84 (s, 3H), 3.85-3.89 (s, 3H), 7.01-7.14 (d, J=8.4 Hz, 1H), 7.61-7.78 (m, 3H), 8.20-8.33 (t, J=1.2 Hz, 1H), 8.72-8.87 (dd, J=5.0, 0.9 Hz, 1H), 13.53-13.88 (s, 1H).

UPLC I (ESI) $R_t$ 1.21 min, m/z 260.5 [M+H]$^+$ (93%).

Step 2: (S)—N-(2-(2-cyanopyrrolidine-1-yl)-2-oxo-ethyl)-2-(3,4-dimethoxyphenyl)isonicotinamide

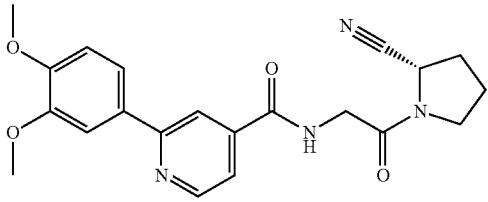 [SMILES: COc1ccc(-c2cc(C(=O)NCC(=O)N3CCC[C@H]3C#N)ccn2)cc1OC]

¹H NMR (400 MHz, CDCl₃): (9/1 mixture of trans/cis amide rotamers) δ 2.16-2.42 (m, 4H), 3.50-3.60 (m, 1H), 3.68-3.78 (m, 1H), 3.92-3.97 (s, 3H), 3.99-4.03 (s, 3H), 4.21 (dd, J=18.0, 3.7 Hz, 1H), 4.36 (dd, J=18.0, 4.7 Hz, 0.9H), 4.46-4.52 (dd, J=17.3, 5.1 Hz, 0.1H), 4.72-4.74 (d, J=8.1 Hz, 0.1H), 4.76-4.83 (dd, J=8.1, 2.8 Hz, 0.9H), 6.97 (d, J=8.4 Hz, 1H), 7.33-7.40 (t, J=3.9 Hz, 1H), 7.48-7.52 (dd, J=5.1, 1.6 Hz, 1H), 7.57-7.61 (dd, J=8.4, 2.1 Hz, 1H), 7.66-7.73 (d, J=2.1 Hz, 1H), 8.00-8.11 (s, 1H), 8.69-8.82 (dd, J=5.0, 0.9 Hz, 1H).
UPLC I (ESI) R_t 1.34 min, m/z 395.5 [M+H]⁺ (100%).
Yield: 0.034 g, 42%.

Example 20

(S)-2-(4-cyanophenyl)-N-(2-(2-cyanopyrrolidine-1-yl)-2-oxoethyl)isonicotinamide

The title compound was prepared in a manner similar to that described in Example 14.

Step 1: 2-(4-cyanophenyl)isonicotinic acid

Yield: 0.154 g, 58%.
¹H NMR (400 MHz, DMSO-d₆): δ 7.82-7.91 (dd, J=4.8, 1.1 Hz, 1H), 7.95-8.06 (m, 2H), 8.30-8.39 (m, 2H), 8.39-8.45 (t, J=1.1 Hz, 1H), 8.87-8.94 (d, J=4.8 Hz, 1H), 13.83-14.15 (br_s, 1H).
UPLC I (ESI) R_t 1.44 min, m/z 225.4 [M+H]⁺ (96%).

Step 2: (S)-2-(4-cyanophenyl)-N-(2-(2-cyanopyrroli-dine-1-yl)-2-oxoethyl)isonicotinamide Yield: 0.045 g, 44%.

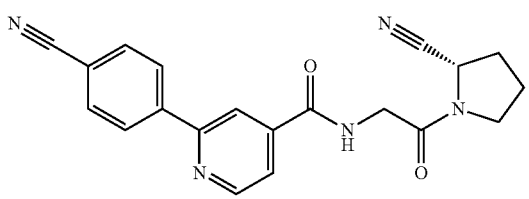 [SMILES: N#Cc1ccc(-c2cc(C(=O)NCC(=O)N3CCC[C@H]3C#N)ccn2)cc1]

¹H NMR (400 MHz, CDCl₃): (9/1 mixture of trans/cis amide rotamers) δ 2.18-2.42 (m, 4H), 3.51-3.58 (m, 1H), 3.70-3.81 (m, 1H), 4.13-4.23 (dd, J=17.8, 3.5 Hz, 0.9H), 4.28-4.34 (dd, J=17.4, 3.6 Hz, 0.1H), 4.43-4.53 (dd, J=17.8, 5.7 Hz, 1H), 4.71-4.73 (dd, J=9.6, 1.9 Hz, 0.1H), 4.74-4.84 (m, 0.9H), 7.61 (dd, J=5.0, 1.5 Hz, 1H), 7.72-7.81 (m, 3H), 8.05-8.16 (m, 3H), 8.76 (d, J=5.0 Hz, 1H).
UPLC I (ESI) R_t 1.44 min, m/z 360.6 [M+H]⁺ (100%).

Example 21

(S)—N-(2-(2-cyanopyrrolidine-1-yl)-2-oxoethyl)-1-methyl-1H-imidazole-5-carboxamide The title compound was prepared in a manner similar to that described in Example 3 using 1-methyl-1H-imidazole-5-carboxylic acid.
Yield: 46 mg, 59%

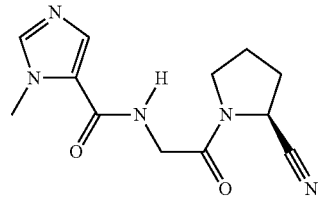 [SMILES: Cn1cncc1C(=O)NCC(=O)N1CCC[C@H]1C#N]

¹H NMR (400 MHz, CDCl₃): (9/1 mixture of trans/cis amide rotamers) δ 2.12-2.40 (m, 4H)), 3.44-3.54 (td, J=9.0, 8.4, 6.3 Hz, 1H), 3.64-3.71 (ddd, J=9.4, 7.0, 3.0 Hz, 1H), 3.84-3.97 (s, 3H), 4.05-4.13 (dd, J=17.7, 3.9 Hz, 0.9H), 4.15-4.23 (m, 0.1H), 4.24-4.33 (dd, J=17.7, 5.2 Hz, 0.9H), 4.34-4.43 (dd, J=17.3, 5.2 Hz, 0.1H), 4.68-4.72 (dd, J=7.8, 1.9 Hz, 0.1H), 4.75-4.81 (m, 0.9H), 7.02-7.08 (d, J=5.6 Hz, 1H), 7.44-7.51 (s, 1H), 7.51-7.57 (s, 1H).
UPLC I (ESI) R_t 0.29 min, m/z 262.6 [M+H]⁺ (98%)

Example 22

(S)—N-(2-(2-cyanopyrrolidine-1-yl)-2-oxoethyl)-4-methylthiazole-5-carboxamide

The title compound was prepared in a manner similar to that described in Example 3 using 4-methylthiazole-5-carboxylic acid.
Yield: 57 mg, 48%

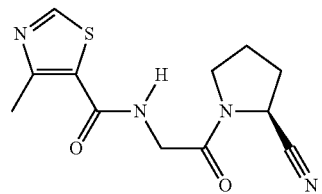 [SMILES: Cc1ncsc1C(=O)NCC(=O)N1CCC[C@H]1C#N]

¹H NMR (400 MHz, CDCl₃): (9/1 mixture of trans/cis amide rotamers) δ 2.14-2.38 (m, 4H), 2.73-2.76 (s, 3H), 3.44-3.54 (m, 1H), 3.64-3.71 (ddd, J=9.3, 7.2, 3.3 Hz, 1H), 4.05-4.16 (dd, J=18.0, 3.4 Hz, 0.9H), 4.18-4.26 (dd, J=17.4, 3.5 Hz, 0.1H), 4.27-4.38 (dd, J=17.8, 5.1 Hz, 0.9H), 4.40-4.47 (dd, J=17.4, 5.1 Hz, 0.1H), 4.71-4.74 (d, J=7.7 Hz, 0.1H), 4.74-4.79 (d, J=7.7 Hz, 0.9H), 7.04-7.13 (d, J=7.3 Hz, 1H), 8.67-8.71 (s, 1H).
UPLC I (ESI) R_t 1.08 min, m/z 279.6 [M+H]⁺ (100%)

Example 23

(S)—N-(2-(2-cyanopyrrolidine-1-yl)-2-oxoethyl)-4-methyloxazole-5-carboxamide

The title compound was prepared in a manner similar to that described in Example 3 using 4-methyloxazole-5-carboxylic acid.
Yield: 34 mg, 36%

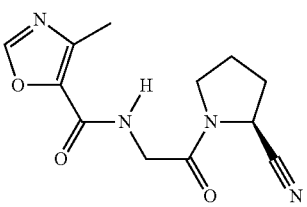 [SMILES: Cc1ncoc1C(=O)NCC(=O)N1CCC[C@H]1C#N]

¹H NMR (400 MHz, CDCl₃): (9/1 mixture of trans/cis amide rotamers) δ 2.18-2.40 (m, 4H, 2.45-2.58 (s, 3H), 3.43-3.56 (m, 1H), 3.64-3.72 (ddd, J=9.5, 7.1, 2.8 Hz, 1H), 4.09-4.16 (dd, J=17.9, 4.0 Hz, 0.9H), 4.17-4.22 (m, 0.1H), 4.22-4.31 (dd, J=17.9, 4.9 Hz, 0.9H), 4.39-4.46 (dd, J=17.3, 5.6 Hz, 0.1H), 4.74-4.83 (d, 8.0 Hz, 0.1H), 4.76-4.83 (dd, J=8.0, 2.6 Hz, 0.9H), 7.12-7.19 (s, 1H), 7.75-7.83 (s, 1H).

UPLC I (ESI) R$_t$ 1.04 min, m/z 263.4 [M+H]⁺ (96%)

Example 24

(S)—N-(2-(2-cyanopyrrolidine-1-yl)-2-oxoethyl)piperidine-4-carboxamide

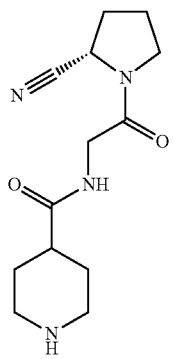 [SMILES: N#C[C@@H]1CCCN1C(=O)CNC(=O)C1CCNCC1]

Step 1: 1-(tert-butoxycarbonyl)piperidine-4-carboxylic acid

The piperidine-4-carboxylic acid (1 g, 7.74 mmol) was added to a stirred solution of guanidine hydrochloride (0.111 g, 1.161 mmol) and di-tert-butyl dicarbonate (4.22 g, 19.36 mmol) in EtOH (7 mL) at 35-40° C. The mixture was stirred overnight. Then the Ethanol was evaporated and the residue was dissolved in CH₂Cl₂ (or EtOAc) and filtered to separate the catalyst. the filtrate was evaporated and washed with hexane to yield a white powder.

¹H NMR (400 MHz, MeOD): δ 1.38-1.52 (s, 9H), 1.47-1.61 (m, 2H), 1.83-1.94 (dq, J=13.9, 3.6 Hz, 2H), 2.43-2.55 (tt, J=11.0, 4.0 Hz, 1H), 2.83-2.96 (br s, 2H), 3.94-4.02 (td, J=4.0, 1.3 Hz, 2H).

MS (ESI) m/z 230.4 [M+H]⁺

Step 2: (S)-tert-butyl 4-(2-(2-cyanopyrrolidine-1-yl)-2-oxoethylcarbamoyl)piperidine-1-carboxylate The title compound was prepared in a manner similar to that described in Example 3 using 1-(tert-butoxycarbonyl)piperidine-4-carboxylic acid UPLC I (ESI) R$_t$ 1.47 min, m/z 365.6 [M+H]⁺ (90%)

Step 3: (S)—N-(2-(2-cyanopyrrolidine-1-yl)-2-oxoethyl)piperidine-4-carboxamide

To a solution of (S)-tert-butyl 4-(2-(2-cyanopyrrolidine-1-yl)-2-oxoethylcarbamoyl)piperidine-1-carboxylate (0.100 g, 0.274 mmol) in 2 ml Acetonitrile was 4-methylbenzenesulfonic acid hydrate (0.073 g, 0.384 mmol) added and the mixture was stirred for 24 h. After evaporation of the volatiles, the sample was purified by preparative HPLC to yield an reddish oil.

Yield: 20 mg, 35%

¹H NMR (400 MHz, MeOD): (9/1 mixture of trans/cis amide rotamers) δ 1.58-1.76 (m, 2H), 1.77-1.89 (m, 2H), 2.11-2.22 (m, 2H), 2.19-2.31 (m, 2H), 2.39-2.54 (tt, J=11.6, 3.8 Hz, 1H), 2.58-2.73 (td, J=12.5, 2.9 Hz, 2H), 3.06-3.12 (t, J=3.3 Hz, 1H), 3.09-3.15 (t, J=3.4 Hz, 1H), 3.48-3.61 (dt, J=9.5, 7.5 Hz, 1H), 3.63-3.77 (m, 1H), 3.92-4.04 (d, J=17.1 Hz, 1H), 3.99-4.12 (d, J=17.1 Hz, 1H), 4.72-4.80 (dd, J=6.1, 4.6 Hz, 0.1H), 5.03-5.07 (m, 0.1H). ¹³C NMR (101 MHz, MeOD): δ 178.10, 169.80, 119.55, 47.9, 46.90, 46.11, 43.66, 42.70, 42.48, 30.97, 29.85, 26.13, 23.76.

UPLC I (ESI) R$_t$ 0.26 min, m/z 265.5 [M+H]⁺ (97%)

Example 25

(S)-5-chloro-N-(2-(2-cyanopyrrolidine-1-yl)-2-oxoethyl)quinoline-4-carboxamide

The title compound was prepared in a manner similar to that described in Example 9

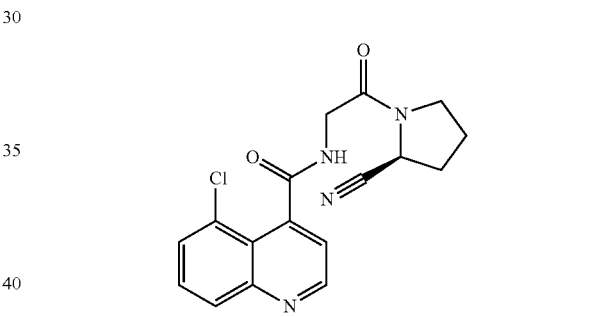

Step 1: 5-chloroquinoline-2,4-dicarboxylic acid

¹H NMR (400 MHz, DMSO-d₆) δ 8.22-8.16 (dd, J=7.3, 2.4 Hz, 1H), 7.98-7.90 (s, 1H), 7.88-7.81 (m, 2H);

UPLC I (ESI) R$_t$ 0.60 min, m/z 252.4 [M+H]⁺ (95%)

Step 2: 5-chloroquinoline-4-carboxylic acid

¹H NMR (400 MHz, DMSO-d₆) δ 8.83-8.76 (d, J=4.3 Hz, 1H), 7.98-7.92 (dd, J=7.4, 2.4 Hz, 1H), 7.70-7.63 (m, 2H), 7.25-7.19 (d, J=4.4 Hz, 1H); UPLC I (ESI) R$_t$ 1.13 min, m/z 208.5 [M+H]⁺ (98%)

(S)-5-chloro-N-(2-(2-cyanopyrrolidine-1-yl)-2-oxoethyl)quinoline-4-carboxamide

Yield: 58 mg, 42%

¹H NMR (400 MHz, CDCl₃) δ 8.97 (d, J, 4.27 Hz, 1H), 8.12 (t, J=4.86 Hz, 1H), 7.68 (dd, J=4.89, 0.86 Hz, 2H), 7.47 (d, J=4.27 Hz, 1H), 6.89 (s, 1H), 4.79 (d, J=6.74 Hz, 1H), 4.32 (br d, J=20.2H), 3.77-3.67 (m, 1H), 3.60-3.51 (m, 1H), 2.41-2.20 (m, 4H);

UPLC I (ESI) R$_t$ 1.26 min, m/z 343.6 [M+H]⁺ (96%); LC-MS (I-B) R$_t$ 11.6 min, m/z 343.1 [M+H]⁺ (96%).

Example 26

(S)-5-bromo-N-(2-(2-cyanopyrrolidine-1-yl)-2-oxo-ethyl)quinoline-4-carboxamide The title compound was prepared in a manner similar to that described in Example 9

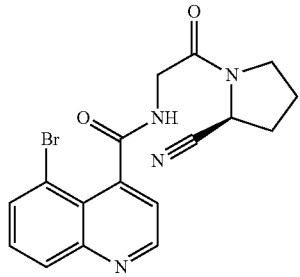 [SMILES: N#C[C@@H]1CCCN1C(=O)CNC(=O)c1ccnc2cccc(Br)c12]

Step 1: 5-bromoquinoline-2,4-dicarboxylic acid $^1$H NMR (400 MHz, DMSO-d$_6$) δ 8.27 (dd, J=8.5, 1.1 Hz, 1H), 8.16 (dd, J=7.6, 1.1 Hz, 1H), 8.07 (s, 1H), 7.83 (dd, J=8.4, 7.7 Hz, 1H); UPLC I (ESI) R$_t$ 1.02 min, m/z 296.5, 298.5 [M+H]$^+$ (95%)

Step 2: 5-bromoquinoline-4-carboxylic acid

The starting material was reacted in a pressured tube for 50 minutes at 205° C. with stirring.

$^1$H NMR (400 MHz, DMSO-d$_6$) δ 9.01-8.91 (d, J=4.3 Hz, 1H), 8.16-8.07 (dd, J=8.4, 1.2 Hz, 1H), 8.05-7.98 (dd, J=7.6, 1.2 Hz, 1H), 7.75-7.69 (dd, J=8.4, 7.5 Hz, 1H), 7.60-7.54 (d, J=4.4 Hz, 1H); UPLC I (ESI) R$_t$ 1.36 min, m/z 252.4, 254.4 [M+H]$^+$ (98%).

Step 3: (S)-5-bromo-N-(2-(2-cyanopyrrolidine-1-yl)-2-oxoethyl)quinoline-4-carboxamide Yield: 39 mg, 42%

$^1$H NMR (400 MHz, CDCl$_3$) δ 8.95 (d, J=4.24 Hz, 1H), 8.16 (dd, J=8.51, 1.25 Hz, 1H), 7.90 (dd, J=7.51, 1.33 Hz, 1H), 7.60 (dd, J=8.47, 7.51 Hz, 1H), 7.49 (d, J=4.25 Hz, 1H), 6.97 (s, 1H), 4.74-4.81 (m, 1H), 4.34 (s, 2H), 3.72 (ddd, J=11.35, 6.78, 2.48 Hz, 1H), 3.59-3.50 (m, 1H), 2.43-2.13 (m, 4H);

UPLC I (ESI) R$_t$ 1.29 min, m/z 387.5, 389.5 [M+H]$^+$ (96%); LC-MS (I-B) R$_t$ 11.9 min, m/z 387.1, 388.9 [M+H]$^+$ (96%); HRMS calcd for: C$_{17}$H$_{16}$N$_4$O$_2$Br [M+H]+, 387.0457; found, 387.0448.

Example 27

(S)—N-(2-(2-cyanopyrrolidine-1-yl)-2-oxoethyl)-5-methylquinoline-4-carboxamide The title compound was prepared in a manner similar to that described in Example 3.

Yield: 72 mg, 47%

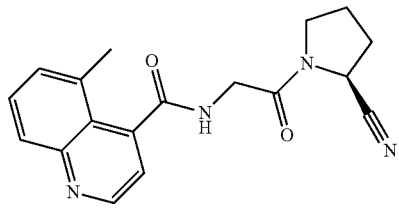 [SMILES: Cc1cccc2nccc(C(=O)NCC(=O)N3CCC[C@H]3C#N)c12]

$^1$H NMR (400 MHz, CDCl3) δ 8.93-8.84 (m, 1H), 8.04-7.96 (m, 1H), 7.62 (dd, J=7.06, 8.49 Hz, 1H), 7.38 (dt, J=1.20, 7.04 Hz, 1H), 7.35 (d, J=4.24 Hz, 1H), 7.06 (t, J=4.50 Hz, 1H), 4.75 (dd, J=1.99, 7.79 Hz, 0.1H), 4.72-4.67 (m, 0.9H), 4.56 (dd, J=5.53, 17.38 Hz, 0.1H), 4.37 (dd, J=4.95, 17.82 Hz, 0.9H), 4.32 (dd, J=5.53, 17.38 Hz, 0.1H) 4.23 (dd, J=3.95, 17.81 Hz, 0.9H), 3.70 (ddd, J=2.77, 7.09, 11.25 Hz, 1H), 3.52 (dt, J=7.63, 10.69 Hz, 1H), 2.65 (s, 3H), 2.42-2.09 (m, 4H).

$^{13}$C NMR (101 MHz, CDCl3) δ 170.38, 166.83, 149.68, 149.13, 141.90, 134.49, 130.19, 129.73, 128.76, 123.43, 119.96, 117.89, 46.78, 45.74, 42.61, 30.05, 25.19, 21.31.

UPLC I (ESI) R$_t$ 1.07 min, m/z 323.5 [M+H]$^+$ (99%); LC-MS (I-B) R$_t$ 10.0 min, m/z 323.1 [M+H]$^+$ (98%)

Example 28

(S)—N-(2-(2-cyano-4,4-difluoropyrrolidine-1-yl)-2-oxoethyl)-6-methoxyquinoline-4-carboxamide The title compound was prepared in a manner similar to that described in Example 1.

Yield: 61 mg, 33%

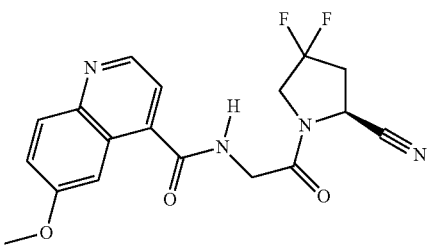 [SMILES: COc1ccc2nccc(C(=O)NCC(=O)N3CC(F)(F)C[C@H]3C#N)c2c1]

$^1$H NMR (400 MHz, CDCl$_3$) (9/1 mixture of trans/cis amide rotamers) δ 8.63 (d, J=4.43 Hz, 1H), 7.90 (d, J=9.19 Hz, 1H), 7.54 (d, J=2.75 Hz, 1H), 7.47-7.40 (br s, 1H), 7.35 (d, J=4.40 Hz, 1H), 7.31 (dd, J=2.78, 9.24 Hz, 1H), 5.19-5.12 (m, 0.1H), 4.91 (dd, J=4.58, 8.37 Hz, 0.9H), 4.52 (d, J=5.77 Hz, 0.1H), 4.30 (dd, J=5.71, 17.35 Hz, 0.9H), 4.12 (dd, J=4.73, 17.33 Hz, 1H), 4.08-3.86 (m, 2H), 3.86 (s, 3H), 2.83-2.65 (m, 4H).

$^{13}$C NMR (101 MHz, CDCl$_3$) δ 168.18, 167.71, 158.77, 147.05, 144.85, 139.04, 131.13, 127.88, 125.54, 123.14, 119.15, 116.40, 102.85, 55.83, 52.05 (t, J=32.25 Hz), 44.41, 42.20, 37.26 (t, J=25.29 Hz).

UPLC I (ESI) R$_t$ 1.28 min, m/z 375.6 [M+H]$^+$ (99%); LC-MS (I-B) (ESI) R$_t$ 11.6 min, m/z 374.9 [M+H]$^+$(98%).

Example 29

(S)—N-(2-(2-cyanopyrrolidine-1-yl)-2-oxoethyl)-5-phenylquinoline-4-carboxamide

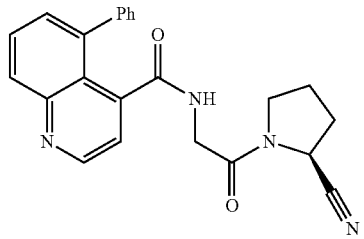 [SMILES: N#C[C@@H]1CCCN1C(=O)CNC(=O)c1ccnc2cccc(-c3ccccc3)c12]

To a solution containing this acid 5-phenylquinoline-4-carboxylic acid (0.04 g, 0.160 mmol) and HOBT (Hydroxybenzotriazole) (0.027 g, 0.177 mmol) in 1,4-dioxane (5 mL) was added a solution of EDC (1-ethyl-3-(3-dimethylaminopropyl)carbodiimide HCl) (0.034 g, 0.177 mmol) in CH2Cl2 (5 mL). The mixture was stirred for 10 min at room temperature. To the resulting solution was added the appropriate amine (S)-1-(2-aminoacetyl)pyrrolidine-2-carbonitrile 4-methylbenzenesulfonate (0.063 g, 0.193 mmol) and DIPEA (0.059 ml, 0.337 mmol) in CH2Cl2 (4 mL), with stirring.

After 2 h, the reaction mixture was diluted with CH2Cl2 and washed with saturated aqueous NaHCO3 solution (10 mL), 0.2N aqueous citric acid solution (10 mL) and brine (10 mL). The combined organic layers were dried over MgSO4, filtered, and concentrated. The mixture was purified using column chromatography with dichloromethane-methanol as an eluent.

Yield: 52 mg, 84%

9/1 mixture of trans/cis amide rotamers, major rotamer: $^1$H NMR (400 MHz, CDCl3) δ 8.98 (d, J=4.21 Hz, 1H), 8.20 (dd, J=1.30, 8.46 Hz, 1H), 7.80 (dd, J=7.14, 8.47 Hz, 1H), 7.52 (dd, J=1.35, 7.16 Hz, 1H), 7.49-7.46 (m, 1H), 7.43 (s, 1H), 7.33 (dd, J=8.72, 11.73 Hz, 2H), 7.05 (s, 1H), 6.49-6.43 (m, 2H), 4.77-4.71 (m, 1H), 4.43 (dd, J=4.80, 17.69 Hz, 1H), 4.29 (dd, J=4.01, 17.76 Hz, 1H), 3.44 (ddd, J=3.19, 7.76, 10.27 Hz, 1H), 3.32-3.10 (m, 1H), 2.44-2.10 (m, 4H).

minor rotamer: $^1$H NMR (400 MHz, CDCl3) δ 8.95 (d, J=4.26 Hz, 1H), 8.16 (dd, J=1.24, 8.46 Hz, 1H), 7.60 (dd, J=7.55, 8.47 Hz, 1H), 7.55 (d, J=4.33 Hz, 1H), 7.49 (d, J=4.27 Hz, 1H), 7.43 (s, 1H), 7.33 (dd, J=8.72, 11.73 Hz, 2H), 6.94 (s, 1H), 6.49-6.43 (m, 2H), 4.79 (d, J=5.81 Hz, 1H), 4.43 (dd, J=4.80, 17.69 Hz, 1H), 4.29 (dd, J=4.01, 17.76 Hz, 1H), 3.76-3.66 (m, 1H), 3.62-3.50 (m, 1H), 2.44-2.10 (m, 4H).

$^{13}$C NMR (101 MHz, CDCl3) δ 167.91, 166.54, 149.70, 141.36, 139.43, 133.70, 131.05, 129.81, 129.32, 128.11, 127.02, 122.45, 121.11, 118.86, 117.70, 100.00, 46.55, 45.37, 42.20, 29.98, 24.97.

LC-MS (I-B) (ESI) R$_t$ 13.3 min, m/z 385.1 [M+H]$^+$ (96%).

Example 30

(S)—N-(2-(2-cyanopyrrolidine-1-yl)-2-oxoethyl)-7-(phenylamino)quinoline-4-carboxamide The title compound was prepared in a manner similar to that described in Example 29.
Yield: 78 mg, 73%

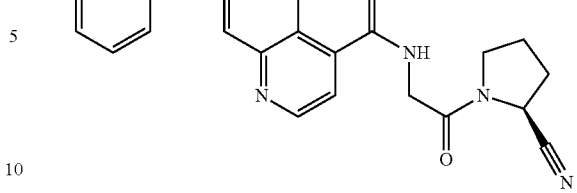

$^1$H NMR (400 MHz, CDCl3) δ 8.67 (d, J=4.43 Hz, 1H), 8.07 (d, J=9.10 Hz, 1H), 7.57 (d, J=2.39 Hz, 1H), 7.42 (t, J=4.78 Hz, 1H), 7.33-7.27 (m, 2H), 7.20 (ddd, J=1.60, 2.58, 8.15 Hz, 4H), 7.02 (tt, J=1.21, 7.35 Hz, 1H), 6.53 (s, 1H), 4.75 (dd, J=1.94, 7.81 Hz, 0.1H), 4.72-4.66 (m, 0.9H), 4.50 (dd, J=5.62, 17.21 Hz, 0.1H), 4.33 (dd, J=5.36, 17.59 Hz, 0.9H), 4.24 (dd, J=3.96, 17.21 Hz, 0.1H), 4.13 (dd, J=4.18, 17.59 Hz, 0.9H), 3.62 (ddd, J=3.23, 7.04, 9.02 Hz, 1H), 3.44 (td, J=4.49, 8.52, 9.05 Hz, 1H), 2.32-2.08 (m, 4H).

$^{13}$C NMR (101 MHz, CDCl3) δ 167.88, 167.29, 150.41, 150.23, 145.40, 141.28, 140.57, 129.56, 126.41, 122.81, 120.71, 119.91, 119.07, 118.12, 115.97, 110.03, 46.77, 45.72, 42.42, 29.93, 25.16.

LC-MS (I-B) (ESI) R$_t$ 11.8 min, m/z 400.0 [M+H]$^+$ (98%).

Example 31

(S)—N-(2-(2-cyanopyrrolidine-1-yl)-2-oxoethyl)-7-phenylquinoline-4-carboxamide

The title compound was prepared in a manner similar to that described in Example 29.
Yield: 86 mg, 74%

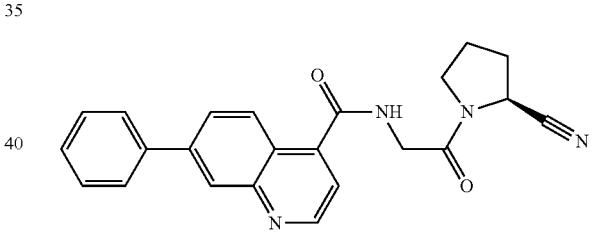

$^1$H NMR (400 MHz, CDCl3) (9/1 mixture of trans/cis amide rotamers) δ 8.96 (d, J=4.35 Hz, 1H), 8.38-8.33 (m, 2H), 7.89 (dd, J=2.01, 8.66 Hz, 1H), 7.79-7.71 (m, 2H), 7.55-7.46 (m, 3H), 7.47-7.37 (m, 1H), 7.22 (t, J=4.58 Hz, 1H), 7.12 (t, J=4.28 Hz, 0.1H), 4.77 (dd, J=2.41, 7.67 Hz, 1H), 4.60 (dd, J=5.54, 17.33 Hz, 0.1H), 4.43 (dd, J=5.07, 17.75 Hz, 0.9H), 4.34 (dd, J=3.51, 17.28 Hz, 0.1H), 4.26 (dd, J=4.02, 17.77 Hz, 0.9H), 3.72 (ddd, J=2.95, 7.09, 9.42 Hz, 1H), 3.59-3.50 (m, 1H), 2.51-2.12 (m, 4H).

$^{13}$C NMR (101 MHz, CDCl3) δ 167.35, 166.97, 150.32, 149.12, 142.68, 140.57, 139.78, 129.07, 128.16, 127.50, 127.47, 127.39, 125.73, 123.49, 118.69, 117.83, 46.72, 45.65, 42.48, 29.94, 25.10.

LC-MS (I-B) (ESI) R$_t$ 14.6 min, m/z 385.1 [M+H]$^+$ (95%).

Example 32

(S)—N-(2-(2-cyanopyrrolidine-1-yl)-2-oxoethyl)-7-methylquinoline-4-carboxamide

The title compound was prepared in a manner similar to that described in Example 3.
Yield: 55 mg, 56%

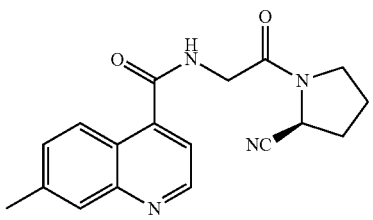 [SMILES: Cc1ccc2c(C(=O)NCC(=O)N3CCC[C@H]3C#N)ccnc2c1]

¹H NMR (400 MHz, CDCl₃) δ 8.89 (d, J=4.36 Hz, 1H), 8.17 (d, J=8.64 Hz, 1H), 7.92-7.88 (m, 1H), 7.47-7.41 (m, 2H), 7.16 (t, J=4.64 Hz, 1H), 4.79-4.73 (m, 1H), 4.58 (dd, J=5.36, 17.37 Hz, 0.1H), 4.40 (dd, J=5.05, 17.76 Hz, 0.9H), 4.31 (dd, J=3.70, 17.23 Hz, 0.1H), 4.24 (dd, J=3.98, 17.77 Hz, 0.9H), 3.70 (ddd, J=2.85, 6.84, 10.97 Hz, 1H), 3.58-3.49 (m, 1H), 2.57 (s, 3H), 2.39-2.17 (m, 4H).
¹³C NMR (101 MHz, CDCl3) δ 167.66, 167.14, 149.91, 149.10, 140.66, 140.60, 130.21, 128.98, 124.96, 122.52, 118.18, 117.96, 46.81, 45.75, 42.56, 30.03, 25.20, 21.93.
UPLC I (ESI) R$_t$ 1.14 min, m/z 323.5 [M+H]⁺ (98%); LC-MS (I-B) R$_t$ 10.1 min, m/z 323.0 [M+H]⁺ (97%)

Example 33

(S)—N-(2-(2-cyanopyrrolidine-1-yl)-2-oxoethyl)-2-(4-methoxyphenyl)-3H-Imidazo[4,5-b]pyridine-7-carboxamide The title compound was prepared in a manner similar to that described in Example 3.
Yield: 67 mg, 75%

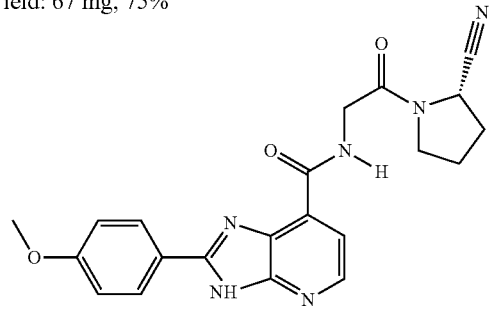

¹H NMR (400 MHz, DMSO) (9/1 mixture of trans/cis amide rotamers) δ 10.15 (s, 1H), 8.44 (d, J=5.02 Hz, 1H), 8.37 (d, J=8.74 Hz, 2H), 7.72 (d, J=4.99 Hz, 1H), 7.17 (d, J=8.78 Hz, 2H), 5.32-5.26 (m, 0.1H), 4.89 (dd, J=4.13, 6.70 Hz, 0.9H), 4.58 (dd, J=4.45, 17.77 Hz, 0.1H), 4.45 (dd, J=4.92, 17.95 Hz, 0.9H), 4.36 (dd, J=4.78, 17.81 Hz, 1H), 3.88 (s, 3H), 3.74 (ddd, J=3.71, 7.64, 11.08 Hz, 1H), 3.55 (td, J=6.92, 9.11 Hz, 1H), 2.23-1.96 (m, 4H).
¹³C NMR (101 MHz, DMSO) δ 170.68, 166.32, 162.77, 161.25, 153.30, 149.94, 142.98, 132.23, 128.45, 120.49, 118.63, 115.75, 114.05, 54.98, 45.82, 44.80, 41.88, 29.03, 24.26.
UPLC I (ESI) R$_t$ 1.50 min, m/z 405.6 [M+H]⁺ (96%); LC-MS (I-B) R$_t$ 14.6 min, m/z 405.0 [M+H]⁺ (97%).

Example 34

(S)—N-(2-(2-cyanopyrrolidine-1-yl)-2-oxoethyl)-1H-pyrrolo[2,3-b]pyridine-4-carboxamide The title compound was prepared in a manner similar to that described in Example 3.
Yield: 50 mg, 35%

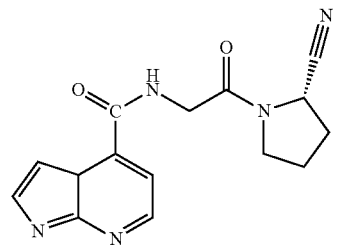 [SMILES: N#C[C@@H]1CCCN1C(=O)CNC(=O)C1=CC=NC2=NC=CC12]

¹H NMR (400 MHz, DMSO) (9/1 mixture of trans/cis amide rotamers) δ 11.88 (s, 1H), 8.68 (t, J=5.69 Hz, 1H), 8.33 (d, J=4.91 Hz, 1H), 7.61 (dd, J=2.51, 3.44 Hz, 1H), 7.42 (d, J=4.92 Hz, 1H), 6.86 (dd, J=1.86, 3.43 Hz, 1H), 5.29 (d, J=7.22 Hz, 0.1H), 4.80 (dd, J=3.62, 7.39 Hz, 0.9H), 4.38 (dd, J=5.71, 16.63 Hz, 0.1H), 4.22 (dd, J=6.09, 16.95 Hz, 0.9H), 4.14 (dd, J=5.47, 16.93 Hz, 1H), 3.73 (ddd, J=3.72, 7.57, 9.60 Hz, 1H), 3.54 (td, J=6.79, 8.95 Hz, 1H), 2.34-2.01 (m, 4H).
UPLC I (ESI) R$_t$ 1.08 min, m/z 298.6 [M+H]⁺ (96%); LC-MS (I-B) (ESI) R$_t$ 9.2 min, m/z 298.0 [M+H]⁺ (97%).

Example 35

(S)—N-(2-(2-cyanopyrrolidine-1-yl)-2-oxoethyl)-[1,2,4]triazolo[1,5-a]pyrimidine-7-carboxamide The title compound was prepared in a manner similar to that described in Example 3.
Yield: 54 mg, 57%

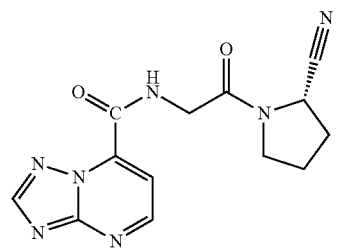 [SMILES: N#C[C@@H]1CCCN1C(=O)CNC(=O)c1ccnc2ncnn12]

¹H NMR (400 MHz, DMSO) δ 9.59 (d, J=6.96 Hz, 1H), 9.28 (s, 1H), 8.86 (s, 1H), 7.87 (d, J=6.95 Hz, 1H), 4.79 (dd, J=3.72, 7.35 Hz, 1H), 4.18 (d, J=5.11 Hz, 2H), 3.76-3.67 (m, 1H), 3.52 (q, J=8.33 Hz, 1H), 2.36-1.97 (m, 4H).
UPLC I (ESI) R$_t$ 1.02 min, m/z 300.6 [M+H]⁺ (96%); LC-MS (I-B) (ESI) R$_t$ 9.0 min, m/z 300.0 [M+H]⁺ (97%).

Example 36

N—((R)-1-((S)-2-cyanopyrrolidine-1-yl)-3-hydroxy-1-oxopropan-2-yl)quinoline-4-carboxamide

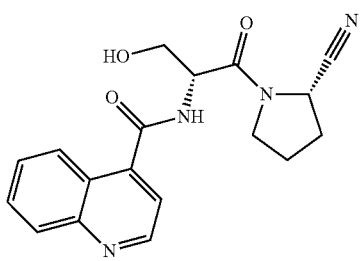 [SMILES: N#C[C@@H]1CCCN1C(=O)[C@@H](CO)NC(=O)c1ccnc2ccccc12]

Step 1: tert-butyl (R)-3-(tert-butyldimethylsilyloxy)-1-((S)-2-cyanopyrrolidine-1-yl)-1-oxopropan-2-yl-carbamate A mixture of DIPEA (0.542 ml, 3.11 mmol) and (S)-pyrrolidine-2-carbonitrile 4-methylbenzenesulfonate (0.269 g, 1.002 mmol) in DCM was added to a mixture of (R)-2-(tert-butoxycarbonylamino)-3-(tert-butyldimethylsilyloxy)propanoic acid (0.320 g, 1.002 mmol) and HATU (0.381 g, 1.002 mmol) in DMF. After 3 h the mixture was washed with 1N citric acid and saturated sodium bicarbonate and brine. The organic layer was dried sodium sulfate, filtered and purified by column chromatography using hexane-ethylacetate as eluents.

$^1$H NMR (400 MHz, CDCl3) δ 5.31-5.22 (d, J=8.4 Hz, 1H), 4.72-4.66 (m, 1H), 4.66-4.56 (td, J=8.9, 5.3 Hz, 1H), 3.86-3.70 (m, 3H), 3.69-3.61 (t, J=9.1 Hz, 1H), 2.36-2.07 (m, 4H), 1.50-1.37 (s, 9H), 0.88-0.78 (s, 9H), 0.03-0.02 (s, 3H), 0.015-0.00 (s, 3H)

UPLC I (ESI) R$_t$ 2.25 min, m/z 398.67 [M+H]$^+$ (96%).

Step 2: (S)-1-((R)-2-amino-3-hydroxypropanoyl)pyrrolidine-2-carbonitrile 4-methylbenzenesulfonate Toxic Acid (0.174 g, 0.916 mmol) was added to a cold (0° C.) solution of tert-butyl (R)-3-(tert-butyldimethylsilyloxy)-1-((S)-2-cyanopyrrolidine-1-yl)-1-oxopropan-2-ylcarbamate (0.260 g, 0.654 mmol) in acetonitrile (about 0.4M) at 0° C. after 30 min the mixture was allowed to warm till room temperature and stirred for 24 h. The volatiles were evaporated and the mixture was washed with cold ethyl acetate to remove N-tert-butyl acetamide, the white precipitate (S)-1-((R)-2-amino-3-hydroxypropanoyl)pyrrolidine-2-carbonitrile 4-methylbenzenesulfonate (0.220, 0.619 mmol, 95% yield)

$^1$H NMR (400 MHz, D$_2$O) δ 7.73-7.66 (m, 2H), 7.40-7.35 (m, 2H), 4.84-4.81 (m, 1H), 4.43 (dd, J=5.5, 4.3 Hz, 1H), 4.02-3.91 (m, 1H), 3.99 (dd, J=12.6, 4.3 Hz, 1H), 3.94 (dd, J=12.6, 5.6 Hz, 1H), 3.62 (dt, J=9.8, 7.9 Hz, 1H), 2.41 (s, 3H), 2.39-2.16 (m, 4H).

UPLC I (ESI) R$_t$ 0.20 min, m/z 184.4 [M+H]$^+$ (94%).

Step 3: N—((R)-1-((S)-2-cyanopyrrolidine-1-yl)-3-hydroxy-1-oxopropan-2-yl)quinoline-4-carboxamide Quinoline-4-carbonyl chloride hydrochloride (0.071 g, 0.310 mmol) was added to a solution of the amine tosyl salt (S)-1-((R)-2-amino-3-hydroxypropanoyl)pyrrolidine-2-carbonitrile 4-methylbenzenesulfonate (0.110 g, 0.310 mmol) and DIPEA (0.168 ml, 0.959 mmol) in DCM and stirred until completion as followed with LC-MS (usually 2 to 3 hours). On completion of the reaction, it was diluted with DCM-isopropanol (4-1), washed with saturated aqueous NaHCO3 solution (10 mL), 0.1N aqueous citric acid solution (10 mL), and brine (10 mL). The organic layer was dried over Na$_2$SO4, filtered, and concentrated and purified with flash chromatography using an ethylacetate-methanol gradient.

Yield: 42 mg, 40%

$^1$H NMR (400 MHz, CDCl3) (10/3 mixture of trans/cis amide rotamers) δ 8.91 (d, J=4.35 Hz, 0.3H), 8.89 (d, J=4.33 Hz, 1H), 8.19 (dd, J=1.29, 8.69 Hz, 1H), 8.19-8.16 (m, 0.3H), 8.13 (d, J=8.75 Hz, 0.3H), 8.11 (dd, J=1.09, 8.75 Hz, 1H), 7.77-7.74 (m, 0.3H), 7.73 (ddd, J=1.39, 6.87, 8.40 Hz, 1H), 7.63-7.59 (m, 0.3H), 7.58 (dd, J=1.30, 6.82, 8.36 Hz, 1H), 7.51 (d, J=7.87 Hz, 1H), 7.46 (d, J=4.31 Hz, 1.3H), 7.43 (d, J=7.26 Hz, 0.3H), 5.62 (dd, J=2.08, 7.73 Hz, 0.3H), 5.11 (dt, J=4.58, 7.87 Hz, 1H), 4.94 (dt, J=3.82, 7.23 Hz, 0.3H), 4.60-4.55 (m, 1H), 4.15 (dd, J=3.43, 11.74 Hz, 0.3H), 4.02 (dd, J=4.18, 11.36 Hz, 1.3H), 3.97-3.89 (m, 2.3H), 3.73-3.62 (m, 2H), 3.59-3.50 (m, 0.6H), 2.46-2.10 (m, 5.2H).

major conformer: $^{13}$C NMR (101 MHz, CDCl3) δ 169.42, 167.55, 149.86, 148.70, 140.63, 130.31, 129.98, 128.14, 125.17, 124.37, 119.00, 117.90, 77.36, 63.36, 53.19, 47.01, 30.08, 25.24.

minor conformer: $^{13}$C NMR (101 MHz, CDCl3) δ 170.61, 168.09, 149.86, 148.76, 140.21, 130.34, 130.10, 128.18, 125.02, 124.37, 119.07, 117.90, 77.36, 62.35, 52.11, 46.65, 32.30, 23.27.

UPLC I (ESI) R$_t$ 1.10 min, m/z 339.6 [M+H]$^+$ (95%); LC-MS (I-B) (ESI) R$_t$ 10.5 min, m/z 339.0 [M+H]$^+$ (95%).

Example 37

N—((R)-1-((S)-2-cyanopyrrolidine-1-yl)-1-oxopropan-2-yl)quinoline-4-carboxamide

The title compound was prepared in a manner similar to that described in Example 36.

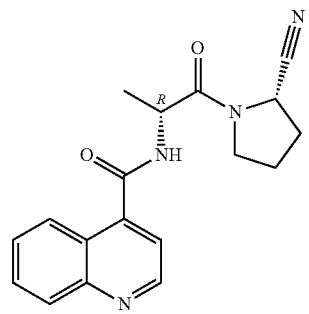

Step 1: tert-butyl (R)-1-((S)-2-cyanopyrrolidine-1-yl)-1-oxopropan-2-ylcarbamate A mixture of DIPEA (1,145 ml, 6.55 mmol) and (S)-pyrrolidine-2-carbonitrile 4-methylbenzenesulfonate (0.567 g, 2,114 mmol) in DCM was added to a mixture of (R)-2-(tert-butoxycarbonylamino)propanoic acid (0.4 g, 2.114 mmol) and HATU (0.804 g, 2.114 mmol) in DMF. After 3 h the mixture was washed with 1N citric acid and saturated sodium bicarbonate and brine. The organic layer was dried sodium sulfate, filtered and purified by column chromatography with a gradient DCM to DCM-MeOH (95-5). (0.47 g, 83%)

$^1$H NMR (400 MHz, CDCl$_3$) δ 5.26 (d, J=7.9 Hz, 1H), 4.78 (dd, J=6.8, 3.7 Hz, 1H), 4.47-4.37 (m, 1H), 3.77-3.58 (m, 2H), 2.33-2.12 (m, 4H), 1.42 (s, J=6.3 Hz, 9H), 1.35 (d, J=6.9 Hz, 3H).

UPLC I (ESI) R$_t$ 1.44 min, m/z 268.5 [M+H]$^+$ (96%).

Step 2: (S)-1-((R)-2-aminopropanoyl)pyrrolidine-2-carbonitrile 4-methylbenzenesulfonate $^1$H NMR (400 MHz, D2O) δ 7.73-7.65 (d, J=8.0 Hz, 3H), 7.40-7.34 (d, J=7.9 Hz, 3H), 4.79-4-75 (m, 1H), 4.39-4.29 (q, J=7.1 Hz, 1H), 3.83-3.73 (dt, J=10.6, 5.7 Hz, 1H), 3.60-3.49 (q, J=8.8 Hz, 1H), 2.45-2.36 (s, 3H), 2.37-2.12 (m, 4H), 1.54-1.44 (dd, J=7.1 Hz, 3H).

UPLC I (ESI) R$_t$ 0.25 min, m/z 168.4 [M+H]$^+$ (95%).

Step 3: N—((R)-1-((S)-2-cyanopyrrolidine-1-yl)-1-oxopropan-2-yl)quinoline-4-carboxamide Quinoline-4-carbonyl chloride hydrochloride (0.067 g, 0.295 mmol) was added to a mixture of DIPEA (0.160 ml, 0.913 mmol) and (S)-1-((R)-2-aminopropanoyl)pyrrolidine-2-carbonitrile 4-methylbenzenesulfonate (0.100 g, 0.295 mmol) in DCM. After 3 h the mixture was washed with 1N citric acid and saturated sodium bicarbonate and brine. The organic layer was dried sodium sulfate, filtered and purified by column chromatography using a mixture of ethylacetate and methanol as eluents.
Yield: 48 mg, 50%
$^1$H NMR (400 MHz, CDCl3) (10/3 mixture of trans/cis amide rotamers) δ 8.94 (d, J=4.31 Hz, 1H), 8.24 (dd, J=1.16, 8.99 Hz, 1H), 8.16-8.11 (m, 1H), 7.76 (ddd, J=1.41, 6.93, 8.38 Hz, 1H), 7.62 (ddd, J=1.36, 6.84, 8.32 Hz, 1H), 7.49 (d, J=4.29 Hz, 1H), 7.19 (d, J=7.55 Hz, 1H), 5.04 (qd, J=2.10, 6.79 Hz, 1H), 4.68 (dd, J=2.00, 8.01 Hz, 1H), 4.00-3.91 (m, 1H), 3.59-3.51 (m, 1H), 2.49-2.10 (m, 4H), 1.52 (d, J=6.83 Hz, 3H).
$^{13}$C NMR (101 MHz, CDCl3) δ 171.10, 166.71, 149.92, 148.79, 141.13, 130.17, 130.02, 127.96, 125.29, 124.50, 118.86, 117.97, 47.67, 47.06, 46.59, 30.15, 25.23, 18.31.
minor conformer: $^1$H NMR (400 MHz, CDCl3) δ 8.93 (d, J=4.30 Hz, 1H), 8.20 (dd, J=1.15, 8.41 Hz, 1H), 8.16-8.11 (m, 1H), 7.76 (ddd, J=1.41, 6.93, 8.38 Hz, 1H), 7.62 (ddd, J=1.36, 6.84, 8.32 Hz, 1H), 7.46 (d, J=4.29 Hz, 1H), 6.93 (d, J=7.24 Hz, 1H), 5.38 (dd, J=2.16, 7.68 Hz, 1H), 5.01-4.95 (m, 1H), 4.00-3.91 (m, 1H), 3.68-3.61 (m, 1H), 2.49-2.10 (m, 4H), 1.62 (d, J=6.87 Hz, 3H).
$^{13}$C NMR (101 MHz, CDCl3) δ 171.07, 166.63, 149.88, 148.76, 141.09, 130.23, 130.07, 128.03, 125.12, 124.43, 118.91, 117.97, 47.56, 47.06, 46.59, 29.82, 23.23, 17.93.
UPLC I (ESI) R$_t$ 1.18 min, m/z 323.6 [M+H]$^+$ (96%); LC-MS (I-B) (ESI) R$_t$ 10.2 min, m/z 323.0 [M+H]$^+$ (97%).

Example 38

(S)—N-(2-(2-cyanopyrrolidine-1-yl)-2-oxoethyl)-1,7-naphthyridine-4-carboxamide

The title compound was prepared in a manner similar to that described in Example 29.
Yield: 58 mg, 57%

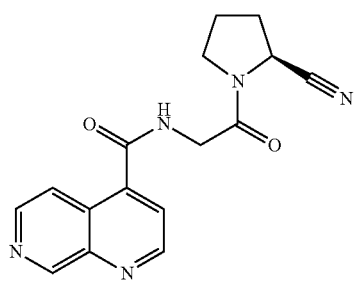 [SMILES: N#C[C@@H]1CCCN1C(=O)CNC(=O)c1ccnc2cnccc12]

Mixture of cis/trans amide conformers (1.5/8.5) Major rotamer: $^1$H NMR (400 MHz, CDCl3) δ 9.44 (d, J=1.02 Hz, 1H), 8.97 (d, J=4.29 Hz, 1H), 8.59 (d, J=5.90 Hz, 1H), 8.12 (dd, J=0.98, 5.86 Hz, 1H), 7.72 (d, J=4.34 Hz, 1H), 7.64-7.57 (m, 1H), 4.76-4.69 (m, 1H), 4.41 (dd, J=5.58, 17.60 Hz, 1H), 4.19 (dd, J=4.00, 17.59 Hz, 1H), 3.69 (ddd, J=3.37, 6.58, 11.84 Hz, 1H), 3.58-3.46 (m, 1H), 2.39-2.07 (m, 4H). Minor rotamer: $^1$H NMR (400 MHz, CDCl3) δ 9.48 (d, J=0.94 Hz, 1H), 9.02 (d, J=4.29 Hz, 1H), 8.61 (d, J=4.26 Hz, 1H), 8.10 (d, 5.86 Hz, 1H), 7.70 (d, J=4.12 Hz, 1H), 7.44 (t, J=4.78 Hz, 1H), 4.79 (dd, J=2.04, 7.77 Hz, 1H), 4.54 (dd, J=5.44, 17.23 Hz, 1H), 4.29 (dd, J=3.98, 17.27 Hz, 1H), 3.69 (ddd, J=3.37, 6.58, 11.84 Hz, 1H), 3.58-3.46 (m, 1H), 2.39-2.07 (m, 4H).
$^{13}$C NMR (101 MHz, CDCl3) δ 167.24, 166.00, 154.45, 151.46, 144.79, 143.45, 139.40, 127.89, 122.74, 118.00, 117.76, 46.82, 45.79, 42.45, 29.91, 25.16.
UPLC I (ESI) R$_t$ 1.03 min, m/z 310.7 [M+H]$^+$ (96%); LC-MS (I-B) R$_t$ 9.0 min, m/z 309.9 [M+H]$^+$ (96%)

Example 39

(S)—N-(2-(2-cyanopyrrolidine-1-yl)-2-oxoethyl)-2-(pyridin-4-yl)acetamide

The title compound was prepared in a manner similar to that described in Example 3.
Yield: 40 mg, 29%

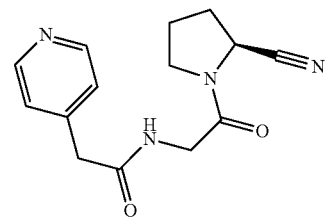 [SMILES: N#C[C@@H]1CCCN1C(=O)CNC(=O)Cc1ccncc1]

$^1$H NMR (400 MHz, MeOD) δ 8.49-8.44 (d, J=4.5, J=1.6 Hz, 2H), 7.46-7.41 (d, J=4.5, J'=1.6 Hz, 2H), 5.05-5.02 (m, 0.14H), 4.79-4.74 (t, J=5.4 Hz, 0.86H), 4.26-4.16 (m, 0.2H), 4.12-4.00 (m, 1.8H), 3.73-3.66 (m, 3H), 3.57-3.49 (dt, J=9.6, 7.6 Hz, 1H), 2.28-2.12 (m, 4H).
$^{13}$C NMR (101 MHz, MeOD) δ 172.5, 169.6, 150.1, 147.3, 126.4, 119.5, 48.0, −46.9, 42.9, 42.5, 31.0, 26.1.
UPLC I (ESI) R$_t$ 0.28 min, m/z 273.6 [M+H]$^+$ (97%); LC-MS (I-B) R$_t$ 1.5 min, m/z 273.0 [M+H]$^+$ (97%)

Example 40

(S)—N-(2-(2-cyanopyrrolidine-1-yl)-2-oxoethyl)-2-(1H-Imidazol-4-yl)acetamide

The title compound was prepared in a manner similar to that described in Example 3.
Yield: 72 mg, 66%

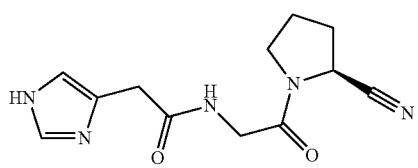 [SMILES: N#C[C@@H]1CCCN1C(=O)CNC(=O)Cc1c[nH]cn1]

$^1$H NMR (400 MHz, MeOD) δ 7.68-7.63 (s, 1H), 7.05-6.99 (s, 1H), 4.78-4.73 (t, J=5.3 Hz, 1H), 4.10-3.98 (m, 2H), 3.71-3.64 (ddd, J=9.7, 6.4, 4.7 Hz, 1H), 3.63-3.58 (s, 2H), 3.56-3.47 (dt, J=9.5, 7.5 Hz, 1H), 2.36-2.06 (m, 4H).
UPLC I (ESI) R$_t$ 0.29 min, m/z 262.6 [M+H]$^+$ (99%); LC-MS (I-B) R$_t$ 1.2 min, m/z 262.0 [M+H]$^+$ (96%)

Example 41

(S)—N-(2-(2-cyanopyrrolidine-1-yl)-2-oxoethyl)-1H-1,2,3-triazole-5-carboxamide

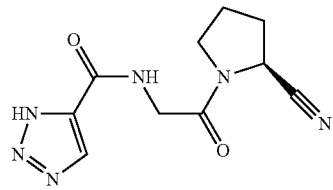 [SMILES: N#C[C@@H]1CCCN1C(=O)CNC(=O)c1cnn[nH]1]

1H-1,2,3-triazole-4-carboxylic acid (0.092 g, 0.814 mmol) was dispersed in dry dioxane (3 mL) in a round bottom flask with nitrogen. To this 1-chloro-N,N,2-trimethylprop-1-en-1-amine (0.151 ml, 1.139 mmol) was added and the reaction was stirred for 30 minutes at room temperature. The starting material dissolves over time. Then (S)-1-(2-aminoacetyl)pyrrolidine-2-carbonitrile hydrochloride (0.247 g, 1.302 mmol) with N-ethyl-N-isopropylpropan-2-amine (0.307 ml, 1.709 mmol) was added and the mixture was stirred for 2 h, evaporated to dryness and redissolved in ethyl acetate. Followed by washing with 0.1N citric acid and saturated sodium bicarbonate and brine. After drying over sodium sulfate, filtration and evaporation, the product was purified using column chromatography.

Yield: 34 mg, 40%

$^1$H NMR (400 MHz, DMSO) (9/1 mixture of trans/cis amide rotamers) δ 15.53 (s, 1H), 8.58-8.44 (s, 1H), 8.39 (s, 1H), 5.28-5.22 (m, 0.1H), 4.77 (dd, J=3.76, 7.32 Hz, 1H), 4.30 (dd, J=5.61, 16.77 Hz, 0.2H), 4.10 (d, J=5.76 Hz, 2H), 3.68 (ddd, J=4.04, 7.68, 9.39 Hz, 1H), 3.50 (td, J=6.84, 9.09 Hz, 1H), 2.31-1.88 (m, 4H).

UPLC I (ESI) R$_t$ 0.72 min, m/z 249.6 [M+H]$^+$ (96%); LC-MS (I-B) R$_t$ 4.0 min, m/z 249.0 [M+H]$^+$ (96%)

Example 42

(S)—N-(2-(2-cyanopyrrolidine-1-yl)-2-oxoethyl)-1H-1,2,4-triazole-3-carboxamide

The title compound was prepared in a manner similar to that described in Example 3.

Yield: 53 mg, 40%

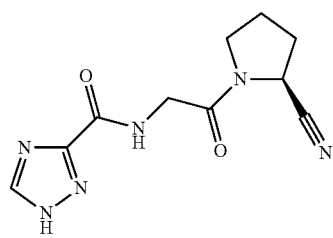 [SMILES: N#C[C@@H]1CCCN1C(=O)CNC(=O)c1nc[nH]n1]

$^1$H NMR (400 MHz, D$_2$O) (9/1 mixture of trans/cis amide rotamers) δ 8.56 (s, 1H), 5.12 (dd, J=2.05, 7.76 Hz, 0.1H), 4.85-4.81 (m, 0.9H), 4.43 (d, J=2.63 Hz, 0.2H), 4.32 (s, 2H), 3.79 (ddd, J=4.53, 7.02, 9.82 Hz, 1H), 3.63 (dt, J=7.65, 9.63 Hz, 1H), 2.48-2.10 (m, 4H).

UPLC I (ESI) R$_t$ 0.77 min, m/z 271.5 [M+Na]$^+$ (97%); LC-MS (I-B) R$_t$ 2.8 min, m/z 249.0 [M+H]$^+$ (97%)

Example 43

(S)—N-(2-(2-cyanopyrrolidine-1-yl)-2-oxoethyl)-3-hydroxyquinoline-4-carboxamide

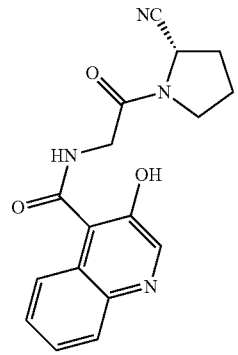 [SMILES: N#C[C@@H]1CCCN1C(=O)CNC(=O)c1c(O)cnc2ccccc12]

To a 50 mL round bottom flask, was added 3-hydroxyquinoline-4-carboxylic acid (0.1 g, 0.529 mmol), acetonitrile (Volume: 10 ml) and N-ethyl-N-isopropylpropan-2-amine (0.157 g, 1.216 mmol) at room temperature with stirring until a solution was observed. Then, di(1H-imidazol-1-yl)methanone (0.094 g, 0.581 mmol) was added in one portion and the mixture was held for 4 h. Then the amine(S)-1-(2-aminoacetyl)pyrrolidine-2-carbonitrile 2,2,2-trifluoroacetate (0.198 g, 0.740 mmol) was added in one portion. The mixture was heated to 75° C., held at 75° C. for 5 h, cooled to room temperature, and stirred at room temperature overnight. The volatiles were evaporated and the residue was redissolved in EtOAc, washed with 0.3N citric acid, saturated sodium bicarbonate, brine, dried over sodium sulfate, filtered and evaporated. The crude product was purified using column chromatography with ethyl acetate-methanol (95-5) mixture to yield the product (0.076 g, 44%)

$^1$H NMR (400 MHz, CDCl3): (8.5/1.5 mixture of trans/cis amide rotamers) δ 8.77 (d, J=3.51 Hz, 1H), 8.24-8.17 (m, 1H), 8.10 (dd, J=1.49, 7.97 Hz, 1H), 7.64 (ddd, J=8.47, 7.06, 1.58 Hz, 1H), 7.59 (ddd, J=8.28, 6.92, 1.48 Hz, 1H), 7.41 (s, 1H), 4.82 (d, J=7.01 Hz, 1H), 4.77-4.71 (m, 0.2H), 4.47 (dd, J=17.1, 4.8 Hz, 0.15H), 4.47 (dd, J=17.76, 4.8 Hz, 0.85H), 4.42-4.36 (m, 0.15H), 4.28 (dd, J=17.84, 3.76 Hz, 0.85H), 3.78-3.69 (m, 1H), 3.57 (m, 1H), 2.43-2.20 (m, 4H); UPLC I (ESI) R$_t$ 1.19 min, m/z 325.6 [M+H]$^+$ (98%)

Example 44

(S)-5-bromo-N-(2-(2-cyano-4,4-difluoropyrrolidin-1-yl)-2-oxoethyl)quinoline-4-carboxamide The title compound was prepared in a manner similar to that described in Example 1 and Example 26.

Yield: 37 mg, 30%

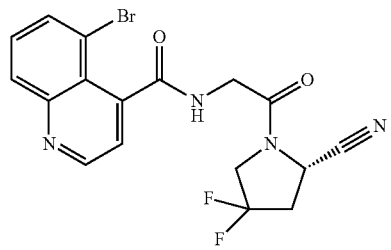 [SMILES: N#C[C@@H]1CC(F)(F)CN1C(=O)CNC(=O)c1ccnc2cccc(Br)c12]

1H NMR (400 MHz, CDCl3) (9/1 mixture of trans/cis amide rotamers) δ 9.10 (dd, J=4.46, 6.43 Hz, 0.9H), 8.88 (s, 0.1H), 8.41 (d, J=8.76 Hz, 1H), 8.05 (d, J=8.73 Hz, 1H), 7.96 (d, J=8.55 Hz, 1H), 7.84 (dd, J=1.06, 7.58 Hz, 1H), 7.55 (dd, J=7.47, 8.49 Hz, 1H), 5.34 (d, J=8.83 Hz, 0.1H), 5.03 (dd, J=5.05, 8.22 Hz, 0.9H), 4.64 (dd, J=6.13, 17.08 Hz, 0.1H), 4.56 (dd, J=6.74, 17.53 Hz, 0.9H), 4.30 (dd, J=4.51, 17.10 Hz, 0.1H), 4.17 (dd, J=4.17, 17.48 Hz, 0.9H), 4.14-4.05 (m, 1H), 4.04-3.95 (m, 1H), 2.84-2.73 (m, 2H). UPLC I (ESI) $R_t$ 1.83 min, m/z 423.5, 425.3 [M+H]$^+$ (96%); LC-MS (I-B) $R_t$ 15.8 min, m/z 265.9, 267.9 (95%)

Example 45

(S)—N-(2-(2-cyanopyrrolidine-1-yl)-2-oxoethyl)-5-methoxyquinoline-4-carboxamide

The title compound was prepared in a manner similar to that described in Example 29.

Yield: 22 mg, 44%

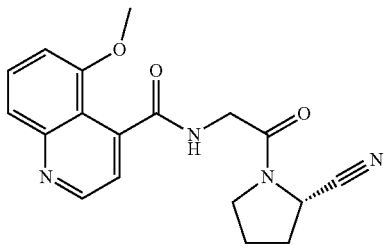 [SMILES: COc1cccc2nccc(C(=O)NCC(=O)N3CCC[C@H]3C#N)c12]

1H NMR (400 MHz, CDCl3) (9/1 mixture of trans/cis amide rotamers) δ 9.01 (d, J=5.51 Hz, 1H), 8.70 (dd, J=0.83, 8.64 Hz, 1H), 8.21 (d, J=8.64 Hz, 1H), 7.74 (dt, J=0.92, 8.66 Hz, 1H), 7.66 (dd, J=7.62, 8.60 Hz, 1H), 6.92 (dd, J=1.01, 7.73 Hz, 1H), 4.88 (d, J=6.04 Hz, 0.1H), 4.85-4.81 (m, 0.9H), 4.58 (dd, J=6.21, 17.03 Hz, 0.1H), 4.42 (dd, J=5.53, 17.72 Hz, 0.9H), 4.34-4.27 (m, 0.1H), 4.25 (dd, J=4.34, 17.75 Hz, 0.9H), 4.02 (s, 3H), 3.78-3.68 (m, 1H), 3.63-3.49 (m, 1H), 2.41-2.17 (m, 4H). 13C NMR (101 MHz, CDCl3) δ 167.50, 164.82, 155.19, 149.17, 147.28, 132.81, 130.53, 122.20, 121.83, 118.15, 118.00, 105.71, 56.01, 46.80, 45.81, 42.34, 30.08, 25.29.

UPLC I (ESI) $R_t$ 1.61 min, m/z 339.6 [M+H]$^+$ (97%); LC-MS (I-B) $R_t$ 14.0 min, m/z 339.1 [M+H]$^+$ (97%)

Example 45

(R)-1-(2-(quinoline-4-carboxamido)acetyl)pyrrolidin-2-ylboronic acid

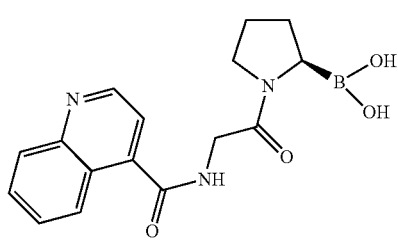 [SMILES: O=C(NCC(=O)N1CCC[C@H]1B(O)O)c1ccnc2ccccc12]

Step 1: N-(2-oxo-2-((2R)-2-((3aS,7aR)-3a,5,5-trimethylhexahydro-4,6-methanobenzo[d][1,3,2]dioxaborol-2-yl)pyrrolidin-1-yl)ethyl)quinoline-4-carboxamide (2R)-2-((3aS,7aR)-3a,5,5-trimethylhexahydro-4,6-methanobenzo[d][1,3,2]dioxaborol-2-yl)pyrrolidine hydrochloride (0.190 g, 0.665 mmol) was added to a mixture of 2-(quinoline-4-carboxamido)acetic acid (0.153 g, 0.665 mmol), HATU (0.253 g, 0.665 mmol) and DIPEA (0.360 ml, 2.062 mmol) in dichloromethane (5 mL). The mixture was stirred for 3 h and washed with 0.5N citric acid, saturated sodium bicarbonate and brine, followed by filtration and evaporation. Purification was done using column chromatography DCM-MeOH 0-6% MeOH.

$^1$H NMR (400 MHz, CDCl3) δ 8.97 (d, J=4.36 Hz, 1H), 8.30 (ddd, J=0.72, 1.48, 8.50 Hz, 1H), 8.17 (dd, J=1.25, 8.28 Hz, 1H), 7.77 (ddd, J=1.44, 6.92, 8.47 Hz, 1H), 7.62 (ddd, J=1.29, 6.94, 8.30 Hz, 1H), 7.53 (d, J=4.34 Hz, 1H), 7.19 (t, J=4.10 Hz, 1H), 4.32-4.27 (m, 3H), 3.61-3.39 (m, 2H), 3.21 (dd, J=6.93, 10.00 Hz, 1H), 2.50-2.25 (m, 1H), 2.25-1.95 (m, 5H), 1.94-1.78 (m, 3H), 1.41 (s, 3H), 1.28-1.24 (m, 4H), 0.82 (s, 3H).

$^{13}$C NMR (101 MHz, CDCl3) δ 167.01, 165.44, 149.56, 130.42, 129.57, 128.03, 125.63, 124.73, 119.02, 86.32, 78.05, 77.36, 53.57, 51.35, 45.86, 42.35, 39.61, 38.75, 38.35, 35.62, 28.59, 27.53, 27.34, 27.20, 26.41, 24.15.

UPLC I (ESI) $R_t$ 1.82 min, m/z 462.7 [M+H]$^+$ (91%);

Step 2: (R)-1-(2-(quinoline-4-carboxamido)acetyl)pyrrolidin-2-ylboronic acid

To a stirred solution of the N-(2-oxo-2-((2R)-2-((3aS,7aR)-3a,5,5-trimethylhexahydro-4,6-methanobenzo[d][1,3,2]dioxaborol-2-yl)pyrrolidin-1-yl)ethyl)quinoline-4-carboxamide (0.27 g, 0.585 mmol) in water (8 mL) at pH=3 (adjusting as necessary with 2N aq HCl) was added phenylboric acid (0.143 g, 1.17 mmol) and methyl-tert-butylether (7 mL). The mixture was stirred for 2 days (pH was 4) water and organic layer were separated, the water layer was adjusted to pH 3, and the water layer was extracted with a mixture 4-1 of DCM-isopropanol. The DCM layer was dried over sodium sulfate, filtrated evaporated and further purified using column chromatography (DCM-MeOH 0-10% MeOH) to yield a clear oil of 0.119 g (79%) (R)-1-(2-(quinoline-4-carboxamido)acetyl)pyrrolidin-2-ylboronic acid.

$^1$H NMR (400 MHz, D2O) δ 8.92-8.84 (m, 1H), 8.15 (ddd, J=0.64, 1.43, 8.58 Hz, 1H), 8.09-8.00 (m, 1H), 7.84 (ddd, J=1.41, 6.92, 8.47 Hz, 1H), 7.70 (ddd, J=1.18, 6.94, 8.29 Hz, 1H), 7.64 (d, J=4.46 Hz, 1H), 4.32-4.27 (m, 2H), 3.67 (ddd, J=3.33, 8.37, 10.14 Hz, 1H), 3.55 (ddd, J=6.54, 8.44, 10.90 Hz, 1H), 3.12 (dd, J=7.01, 10.34 Hz, 1H), 2.13 (tdd, J=3.42, 7.02, 9.03 Hz, 2H), 2.08-1.87 (m, 1H), 1.82-1.68 (m, 1H).

13C NMR (101 MHz, D2O) δ 170.63, 168.11, 150.41, 147.54, 142.15, 131.50, 128.92, 128.64, 125.66, 124.61, 119.99, 48.94 ($^{13}$C—B splitting), 47.22, 42.32, 27.48, 27.43.

UPLC I (ESI) $R_t$ 1.01 min, m/z 328.6 [M+H]$^+$ (99%); LC-MS (I-B) $R_t$ 9.3 min, m/z 328.0 [M+H]$^+$ (98%)

2 In Vitro and In Vivo Assay Protocols.

2.1 Enzymatic Assays.

2.1.1 Enzymes

DPP IV, DPP II, DPP8 and DPP9 were obtained as described in reference 18. Recombinant murine FAP was purified from the culture supernatant of HEK293 human embryonic kidney celline as described in reference 19. Recombinant human PREP was expressed in and purified from E coli as described before in reference 20.

2.1.2 IC$_{50}$ Measurements

Enzyme activities were determined kinetically in a final volume of 200 μl for 10 minutes at 37° C. by measuring the initial velocities of pNA release (405 nm) from the substrate using a Spectramax plus microtiterplate reader (Molecular devices). One unit of enzyme activity was defined as the amount of enzyme that catalyzes the release of 1 μmol pNA from the substrate per minute under assay conditions.

All measurements were carried out in duplicate. The IC$_{50}$ value was defined as the inhibitor concentration, which caused a 50% decrease of the activity under assay conditions.

IC50, Purified Enzymes

The chromogenic substrate Gly-Pro-p-nitroanilide (100 μmol/l) was used at pH 8.3 for DPP IV, Lys-Ala-p-nitroanilide (1 mmol/l) at pH 5.5 for DPP II, Ala-Pro-p-nitroanilide (300 μmol/l) at pH 7.4 for DPP9 and Ala-Pro-p-nitroanilide (2 mmol/l) at pH 7.4 for FAP activity measurement. To evaluate the endopeptidase activity of FAP and the influence of inhibitors thereon, Z-Gly-Pro-AMC and Z-Gly-Pro-p-nitroanilide were used at a final concentration of 300 and 100 μmol/l, respectively. The substrate concentrations were chosen around the Km value obtained under the assay conditions used. Buffer compositions for the DPP assays were reported before in the purification articles—vide supra. The FAP assay buffer consisted of 50 mM Tris pH7.4 containing 100 mmol/l NaCl and 0.1 mg/ml bovine serum albumin. The PREP activity was measured as described by Brandt et al. using the chromogenic substrate Z-Gly-Pro-p-nitroanilide (0.25 mmol/l) at pH 7.5 in the presence of 10 mmol/l DTT.[18]*Test compounds were dissolved and diluted in DMSO (final concentration DMSO during assay 5% v/v) except for FAP where dilution of the inhibitor was done in water. Inhibitors are pre-incubated with the enzyme for 15 min at 37° C. before starting the assay by the addition of substrate. The concentration of enzyme and of inhibitor during the preincubation is double of the final concentration during activity measurement.

IC50, Plasma

For the measurements of endogenous FAP AND PREP activity in plasma, Z-Gly-Pro-AMC was used as a substrate at a concentration of 260 μmol/l in phosphate buffer pH 7.5 containing 1 mmol/l NaN$_3$, 1 mmol/l EDTA with or without 10 mmol/l dithiothreitol (DTT). Final dilution of the plasma in the assay is 20 times. The 'total' activity (FAP AND PREP) is measured when DTT is present, while in the absence of DTT, only FAP activity can be measured. The endogenous PREP activity is calculated as the difference between the 'total' activity and the FAP activity.

3 Biochemical Evaluation Results

3.1 Inhibitory Potency/Selectivity of Compounds

A set of reference compounds was prepared and evaluated that structurally are not of Formula (I), but nonetheless are close analogues of the compounds that correspond to Formula (I). These reference compounds serve as a control for the validity of our novel SAR data that form the basis of the present invention. Results, given as IC$_{50}$-values, are summarised in Table 3.

Relevance of the N Position

With FAP-affinities spanning almost three orders of magnitude, evaluation results of the compounds as depicted in table 3, nonetheless reveal a pivotal importance of the nitrogen's position. Of all the positional isomers synthesized, the 4-quinolinoyl ring clearly displays the best results and takes in a singular position within this series. The 4-isoquinolinoyl and 8-quinolinoyl derivatives are characterized by very low FAP-affinity.

All compounds were used in inhibition assays for FAP (DPPIV (dipeptidyl peptidase-4), DPP9, DPP2 and PREP (prolyl endopeptidase). DPP9 potencies reported can reasonably be expected to be indicative for inhibitor affinities toward the highly homologous DPP8.

TABLE 3

Reference compounds

| | | IC$_{50}$(μM) | | | | | Selectivity index |
|---|---|---|---|---|---|---|---|
| Structure | R1, R2 | FAP | DPPIV | DPP9 | DPP2 | PREP | FAP/PREP |
| 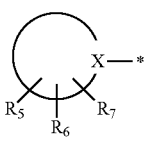<br>Ref. Cmpd No 1<br>(Example 2) | F, F | 0.110 ± 0.007 | >100 | >100 | >100 | 4.8 ± 0.4 | 43 |
| 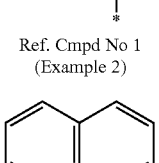<br>Ref. Cmpd No 2 | H, H | 0.67 ± 0.04 | >100 | >100 | >100 | 3.6 ± 0.2 | 5 |
| 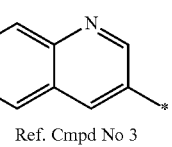<br>Ref. Cmpd No 3<br>(Example 5) | H, H | 5.3 | >100 | >100 | >100 | 9 | 1.7 |

TABLE 3-continued
Reference compounds
| | | IC$_{50}$(μM) | | | | | Selectivity index |
|---|---|---|---|---|---|---|---|
| R1, R2 | FAP | DPPIV | DPP9 | DPP2 | PREP | FAP/PREP |
| Structure | R1, R2 | FAP | DPPIV | DPP9 | DPP2 | PREP | Selectivity index FAP/PREP |
|---|---|---|---|---|---|---|---|
| 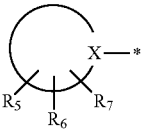 Ref. Cmpd No 4 | H, H | 15.4 ± 0.4 | >100 | >100 | >100 | >100 | >7 |
| 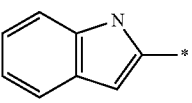 Ref. Cmpd No 5 | H, H | 3.6 ± 0.2 | >100 | >25 | >100 | 13.2 ± 0.4 | 3.6 |
| 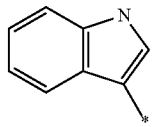 Ref. Cmpd No 6 (Example 7) | H, H | 2.17 ± 0.09 | >100 | >100 | >100 | 8.2 ± 0.8 | 3.77 |
| 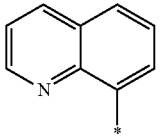 Ref Cmpd No 7 (example 17) | H, H | 0.42 ± 0.04 | >100 | >100 | >100 | 3.4 ± 0.2 | 8 |
| 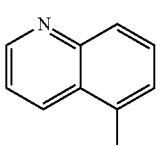 Ref Cmpd No 8 | | 4.8 ± 0.2 | >100 | >100 | >100 | 0.61 ± 0.07 | 0.13 | 0.1 |
| 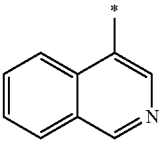 Cmpd No 2 (Example 3) | | 0.0103 ± 0.0004 | >100 | >100 | >100 | 0.86 ± 0.07 | 83.5 | 83 |
| 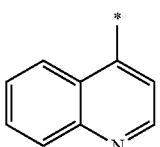 Ref Cmpd No 9 | | 0.107 ± 0.008 | >100 | >100 | >100 | 2.4 ± 0.1 | 22.4 | 22.4 |

TABLE 3-continued

Reference compounds

| R1, R2 | IC₅₀ (μM) | | | | | Selectivity index |
|---|---|---|---|---|---|---|
| | FAP | DPPIV | DPP9 | DPP2 | PREP | FAP/PREP |
| (Ref Cmpd No 10, isoquinoline) | 0.158 ± 0.004 | >100 | >100 | >100 | 11.7 ± 0.8 | 74.1 | 74 |

Table 4 represents evaluation data for compounds of the general formula that structurally accord to this invention:

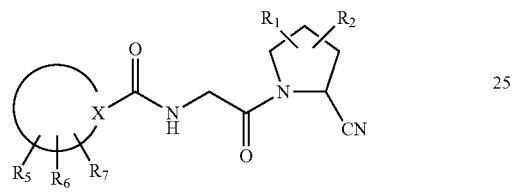

TABLE 4

Compounds according to this invention

| Structure | R1, R2 | IC₅₀ (μM) FAP | DPPIV | DPP9 | DPP2 | PREP | Selectivity index FAP/PREP |
|---|---|---|---|---|---|---|---|
| Cmpd No 1, Example 1 (quinolin-4-yl) | F, F | 0.0032 ± 0.0004 | >100 | >12.5 | >100 | >1.8 +/− 0.2 | 562 |
| Cmpd No 2, Example 3 (quinolin-4-yl) | H, H | 0.0103 ± 0.0004 | >100 | >100 | >100 | 0.86 ± 0.07 | 83 |
| Cmpd No 3, Example 4 (2-methylquinolin-4-yl) | H, H | 0.67 | >100 | >100 | >100 | 0.64 | 1 |

TABLE 4-continued
Compounds according to this invention
| R1, R2 | IC$_{50}$ (μM) FAP | DPPIV | DPP9 | DPP2 | PREP | Selectivity index FAP/PREP |
|---|---|---|---|---|---|---|
| 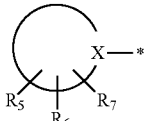<br>Cmpd No 4<br>Example 6<br>H, H | 0.063 | >100 | >100 | >100 | 11.3 | 179 |
| 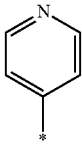<br>Cmpd No 5<br>Example 8<br>H, H | 5.9 ± 0.4 | >100 | >100 | >100 | 53.6 ± 1.3 | 9 |
| 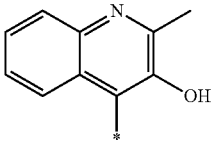<br>Cmpd No 6<br>Example 9<br>H, H | 0.0103 ± 0.0007 | >100 | >100 | >100 | 0.61 ± 0.06 | 59 |
| 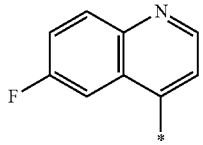<br>Cmpd No 7<br>Example 10<br>H, H | 0.014 ± 0.001 | >100 | >100 | >100 | 0.84 ± 0.07 | 60 |
| 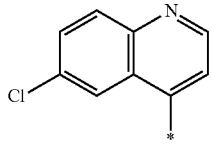<br>Cmpd No 8<br>Example 11<br>H, H | 0.012 ± 0.001 | >100 | >100 | >100 | 0.71 ± 0.05 | 59 |
| 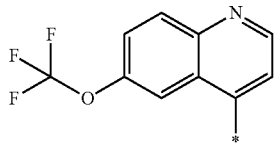<br>Cmpd No 9<br>Example 12<br>H, H | 0.19 ± 0.01 | >100 | >100 | >100 | 0.35 ± 0.03 | 1.8 |

TABLE 4-continued
Compounds according to this invention
| R1, R2 | IC$_{50}$ (μM) FAP | DPPIV | DPP9 | DPP2 | PREP | Selectivity index FAP/PREP |
|---|---|---|---|---|---|---|
| 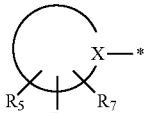<br>Cmpd No 10<br>Example 13<br>H, H | 0.37 ± 0.02 | >100 | >100 | >100 | 0.36 ± 0.02 | 1 |
| 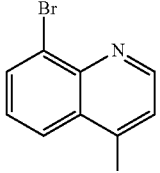<br>Cmpd No 11<br>Example 14<br>H, H | 0.0092 ± 0.0005 | >100 | >100 | >100 | 6.1 ± 0.4 | 677 |
| 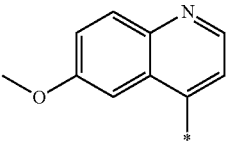<br>Cmpd No 12<br>Example 15<br>H, H | 0.0062 ± 0.0004 | >100 | >100 | >100 | 1.2 ± 0.1 | 193 |
| 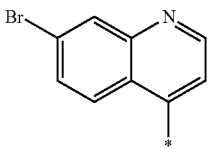<br>Cmpd No 13<br>Example 16<br>H, H | 0.0071 ± 0.0003 | >100 | >100 | >100 | 1.4 ± 0.08 | 197 |
| 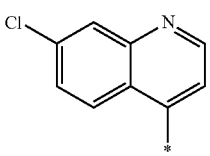<br>Cmpd No 14<br>Example 18<br>H, H | 0.29 ± 0.02 | >100 | >25 | >100 | 14.2 ± 1.0 | 49 |

TABLE 4-continued
Compounds according to this invention
| | IC$_{50}$ (μM) | | | | | | Selectivity index FAP/ |
|---|---|---|---|---|---|---|---|
| R1, R2 | | FAP | DPPIV | DPP9 | DPP2 | PREP | PREP |
| 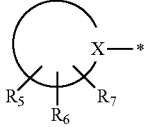<br>Cmpd No 15<br>Example 19 | H, H | 0.22 ± 0.02 | >100 | >100 | >100 | 11.8 ± 0.6 | 51 |
| 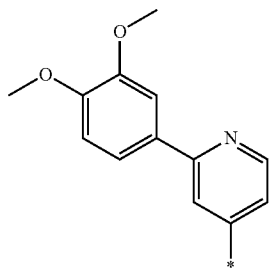<br>Cmpd No 16<br>Example 20 | H, H | 0.27 ± 0.02 | >100 | >100 | >100 | 29.1 ± 2.4 | 107 |
| 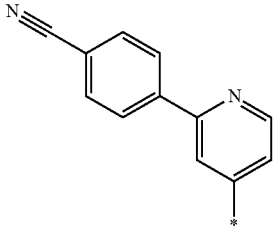<br>Cmpd No 17<br>Example 21 | H, H | 1.37 ± 0.04 | >100 | >100 | >100 | 6.6 ± 0.3 | 4.8 |
| 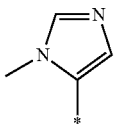<br>Cmpd No 18<br>Example 22 | H, H | 2.5 ± 0.1 | >100 | >100 | >100 | 7.2 ± 0.5 | 2.9 |
| 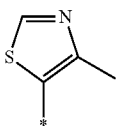<br>Cmpd No 19<br>Example 23 | H, H | 10.2 ± 0.5 | >100 | >100 | >100 | 13.7 ± 1.2 | 1.3 |

TABLE 4-continued
Compounds according to this invention
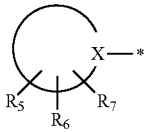
| R1, R2 | IC$_{50}$ (μM) FAP | DPPIV | DPP9 | DPP2 | PREP | Selectivity index FAP/PREP |
|---|---|---|---|---|---|---|
| H, H | 0.75 ± 0.07 | >100 | >100 | >100 | 5.9 ± 0.2 | 7.8 |
Cmpd No 20
Example 24
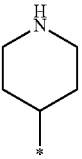
| | | | | | | |
|---|---|---|---|---|---|---|
| H, H | 0.0099 ± 0.0003 | >100 | >100 | >100 | 16.8 ± 0.5 | 1700 |
Cmpd No 21
Example 25
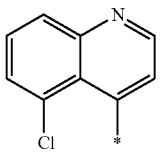
| | | | | | | |
|---|---|---|---|---|---|---|
| H, H | 0.011 ± 0.0004 | >100 | >100 | >100 | >50 | >4500 |
Cmpd No 22
Example 26
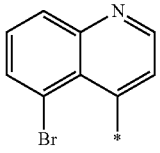
| | | | | | | |
|---|---|---|---|---|---|---|
| H, H | 0.0043 ± 0.0001 | >100 | >50 | >100 | 9.1 ± 0.6 | 2100 |
Cmpd No 23
Example 27
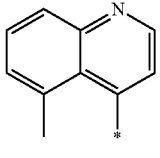
| | | | | | | |
|---|---|---|---|---|---|---|
| F, F | 0.0085 ± 0.0009 | 19 ± 1.3 | 23 ± 2 | >100 | 8.3 ± 0.7 | 970 |
Cmpd No 24
Example 28
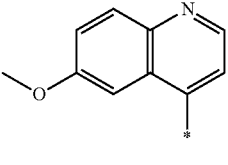
| | | | | | | |
|---|---|---|---|---|---|---|
| H, H | 0.070 ± 0.009 | >100 | >50 | >100 | 19.4 ± 0.7 | 280 |
Cmpd No 25
Example 29

TABLE 4-continued
Compounds according to this invention
| | IC$_{50}$ (μM) R1, R2 | FAP | DPPIV | DPP9 | DPP2 | PREP | Selectivity index FAP/PREP |
|---|---|---|---|---|---|---|---|
| 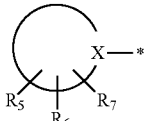<br>Cmpd No 25<br>Example 30 | H, H | 0.059 ± 0.008 | >100 | 20.8 ± 1.8 | >100 | 2.03 ± 0.04 | 34 |
| 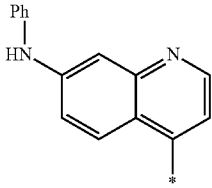<br>Cmpd No 26<br>Example 31 | H, H | 0.064 ± 0.002 | >100 | >50 | >100 | 8.7 ± 0.5 | 135 |
| 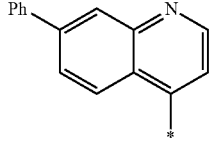<br>Cmpd No 27<br>Example 32 | H, H | 0.0069 ± 0.0003 | >100 | >100 | >100 | 0.50 ± 0.03 | 72 |
| 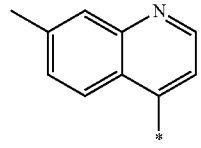<br>Cmpd No 28<br>Example 33 | H, H | <0.2 | >100 | >100 | >100 | >100 | >200 |
| 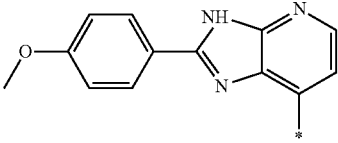<br>Cmpd No 29<br>Example 34 | H, H | 0.040 ± 0.002 | >100 | >100 | >100 | 2.7 ± 0.2 | 67 |
| 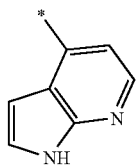<br>Cmpd No 30<br>Example 35 | H, H | 3.2 ± 0.1 | >100 | >100 | >100 | 24 ± 1 | 8 |

TABLE 4-continued
Compounds according to this invention
| | R1, R2 | IC$_{50}$ (µM) FAP | DPPIV | DPP9 | DPP2 | PREP | Selectivity index FAP/PREP |
|---|---|---|---|---|---|---|---|
| 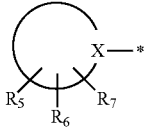<br>Cmpd No 31<br>Example 36 | | 6 ± 0.2 | >100 | >100 | >100 | >100 | >16 |
| 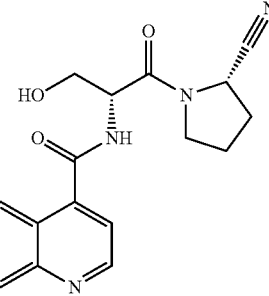<br>Cmpd No 32<br>Example 37 | | 3.4 ± 0.1 | >100 | >100 | >100 | 5.8 ± 0.6 | 1.7 |
| 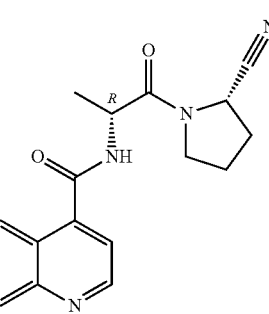<br>Cmpd No 33<br>Example 38 | H, H | 0.028 ± 0.001 | >100 | >100 | >100 | 3.4 ± 0.2 | 120 |
| 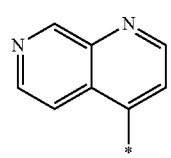<br>Cmpd No 34<br>Example 39 | H, H | 3.3 ± 0.1 | >100 | >100 | >100 | 2.0 ± 0.2 | 0.6 |
| 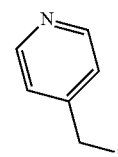<br>Cmpd No 35<br>Example 40 | H, H | 7.2 ± 0.3 | >100 | >50 | >100 | 22 ± 2 | 3 |

TABLE 4-continued

Compounds according to this invention

| R1, R2 | IC$_{50}$ (μM) FAP | DPPIV | DPP9 | DPP2 | PREP | Selectivity index FAP/PREP |
|---|---|---|---|---|---|---|
| 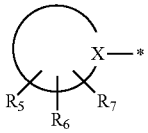 H, H | 5.7 ± 0.2 | >100 | >100 | >100 | >100 | >17 |
| Cmpd No 36 Example 41 | | | | | | |
| 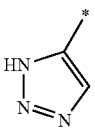 H, H | 22.4 ± 1.1 | >100 | >100 | >100 | >100 | >4.5 |
| Cmpd No 37 Example 42 | | | | | | |
| 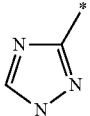 H, H | 0.16 ± 0.01 | >100 | >100 | >100 | 38 ± 2 | 230 |
| Cmpd No 38 Example 43 | | | | | | |

As evident from Table 4, all compounds according to this invention have an IC$_{50}$ for FAP which is less than 10 μM. Furthermore, most of the compounds according to this invention have an IC$_{50}$ for FAP which is less than 1 μM, whereas most of the used reference compounds have an IC$_{50}$ which is at least 10-fold higher (see table 2). In addition, apart from compound 8 and reference compound 5, most of the exemplified compounds have an IC$_{50}$ value for DPPIV, DPP9 and DPP2 which is more than 100 μM, indicating that all of said compounds have a higher selectivity for FAP than for DPPIV, DPP8, DPP9 and DPP2. Furthermore, in comparison to the used reference compounds, most compounds according to this invention have an at least 50× higher selectivity for FAP than for PREP.

3.2 Evaluation of the Inhibitory Potency Toward the Endo- and Exopeptidase Activity of FAP As explained in the 'background to the invention', FAP displays both endo- and exopeptidase activity, mediated by the same active center. The following data provide experimental evidence that the inhibitors that structurally accord to this invention, inhibit both activity types of FAP to the same extent (exemplified using Cmpd No 1 from table 4).

| Inhibition of endopeptidase activity | | |
|---|---|---|
| Cmpd No 1 (table 4): | IC$_{50}$ value using Z-Gly-Pro-AMC as a substrate: | 3.2 nmol/l |
| | IC$_{50}$ value using Z-Gly-Pro-p-NA as a substrate: | 2.3 nmol/l |
| | Compared to IC$_{50}$ value using Ala-Pro-p-NA | 3.2 nmol/l |

Conclusion:

In this in vitro setting, Cmpd No 1 inhibits endo- and exopeptidase activity to the same extent.

3.3 Functional Stability in Plasma

As explained hereinbefore, several known FAP inhibitors, including the clinically relevant Val-boroPro (talabostat), suffer from poor stability both in aqueous solution and in plasma. The 'functional' stability of compound Cmpd No 1 was determined in rat as well as in human plasma and serves as an example of the excellent potential of the compounds according to the present invention with regards to aqueous/plasma stability.

Conclusion:

Preincubation of Cmpd No 1 in rat or human plasma for over 12 h at 37° C. did not result in a shift of ICs values. Final concentrations of 2.5 and 5 nmol/l all resulted in inhibition of 50% or more in an inhibition assay as described above. The compound is very stable in plasma. (Or in case metabolites are formed, they are equally potent)

3.4 Inhibition of Plasma FAP Activity.

The potential of compounds according to the present invention to inhibit FAP activity in biologically relevant matrices is exemplified using IC$_{50}$-values for Cmpd No 1 and Cmpd No 2 in plasma. These are similar to the ones observed in the assays with purified enzyme (Table 4).

The IC$_{50}$ values for inhibition of endogenous FAP activity in plasma:

Cmpd No 2: IC$_{50}$ value using Z-Gly-Pro-AMC as a substrate: 22.6 nmol/l

Cmpd No 1: IC$_{50}$ value using Z-Gly-Pro-AMC as a substrate: 4.4 nmol/l

Conclusion:

Very limited plasma shifts were observed for Cmpd No 1 and Cmpd No 2.

3.5 Selectivity of Cmpd No 1 in Plasma

The potential of compounds according to the present invention to selectively inhibit FAP activity in biologically relevant matrices is exemplified using $IC_{50}$-values for Cmpd No 1 and Cmpd No 2 in plasma. These are similar to the ones observed in the assays with purified enzyme (Table 4).

Conclusion:

In the presence of 100 nmol/l Cmpd No 1, plasma FAP activity is inhibited >90%, while PREP activity remains >95% of the control without Cmpd No 1.

3.6 Preclinical ADME of Selected Compounds

Selected compounds were tested on LOG D, pH 7.4, kinetic solubility, plasma stability in mouse and human, as well as metabolic stability in mouse and stability in plasma (Table 6). The results of all tests until now are satisfactory.

TABLE 6

Preclinical ADME of selected compounds

| Compound No | LOG D | Kinetic solubility | Plasma stability (mouse) | Plasma stability (human) | Metabolic stability (mouse) | Stability in PBS buffer |
|---|---|---|---|---|---|---|
| No 1 | 1 | >200 µM | >24 h | | 90% after 24 h | >24 h |
| No 2 | 0.51 | >200 µM | >24 h | | | |
| No 14 | 0.8 | | >6 h | | | |
| No 22 | 0.7 | | >6 h | >6 h | 70% after 24 h | |

REFERENCES

1) Wolf, B. B.; Quan, C.; Tran, T.; Wiesman, C.; Sutherlin, C. *Mini-Rev. Med; Chem.* 2008, 8, 719-727
2) Lee, K. N.; Jackson, K. W.; Christiaensen, V. J.; Lee, J. S.; Chun, J. G.; McKee, P. A. *Blood* 2006, 107, 1397-1404. (b) Brokopp, C. E.; Schoenauer, R.; Richards, P.; Bauer, S.; Lohmann, C.; Emmert, M. Y.; Weber, B.; Winnik, S.; Aikawa, E.; Graves, K.; Genoni, M.; Vogt, P.; Lüscher, T. F.; Renner, C.; Hoerstrup, S. P.; Matter, C. M. *Eur. Heart J.* 2011, published online doi 10.1093/eurheartj/ehq519 (c) Park, J. E.; Lenter, M. C.; Zimmermann, R. N.; Garin-Chesa, P.; Old, L. J.; Rettig, W. J. *J. Biol. Chem.* 1999, 274, 36505-36512. (d) Huang, C. H.; Suen, C. S.; Lin, C. T.; Chien, C. H.; Lee, H. Y.; Chung, K. M.; Tsai, T. Y.; Jiaang, W. T.; Hwang, M. J.; Chen, X. *J. Biochem.* 2011, published online doi:10.1093/jb/mvr017
3) Keene, F. M.; Nadvi, N. A.; Yao, T. W.; Gorrell, M. D. *FEBS journal* 2011, 278, 8, 1316-1332.
4) Lo, P. C.; Chen, J.; Stefflova, K.; Warren, M. S.; Navab, R.; Bandarchi, B.; Mullins, S.; Tsao, M.; Cheng, J. D.; Zheng, G.; *J. Med. Chem.* 2009, 52, 358-368.
5) (b) Loeffler, M.; Krügeri, J. A.; Niethammer, A. G.; Reisfeld, R. A. *J. Clin. Invest.* 2006, 166, 1955-1962. (b) Hofheinz, R. D.; Al-Batran, S. E.; Hartmann, F.; Hartung, D.; Jager, G.; Renner, C.; Tanswell, P.; Kunz, U.; Amelsberg, A.; Kuthan, A.; Stehle, G. *Onkologie* 2003, 26, 44-48.
6) (a) Cheng, J. D.; Valianou, M.; Canutescu, A. A.; Jaffe, E. K.; Lee, H. O.; Wang, H.; Lai, J. H.; Bachovchin, W. W.; Weiner, L. M. *Mol. Cancer. Ther.* 2005, 4, 351-360. (b) Cheng, J. D.; Dunbrack, R. L., Jr.; Valianou, M.; Rogatko, A.; Alpaugh, R. K.; Weiner, L. M. *Cancer Res.* 2002, 62, 4767-4772. (c) Santos, A. M.; Jung, J.; Aziz, N.; Kissil, J. L. Puré, E.; *J. Clin. Invest.* 2009, 109, 3613-3625.
7) Cunningham, C.; Pavlick, A. C.; Khan, K. D.; Frenette, G. O'Day, S.; Stephenson, J.; Gonzalez, R.; Yang, Z.; Vrhovac, V.; Uprichard, M. J. *J. Clin. Oncol.* 2006, 24, 462s
8) Acharya, P. S.; Zukas, A.; Chandan, V.; Katzenstein, A. L.; Puré, E. *Hum. Pathol.* 2006, 37, 3, 352-360
9) Levy, M. T.; McCaughan, G. W.; Abbott, C. A. Park, J. E.; Cunningham, A. M.; Müller, E.; Rettig, W. J.; Gorrell, M. D. *Hepatology* 1999, 29 1768-1778
10) Dienus, K.; Bayat, A.; Gilmore, F.; Seifert, O. *Arch. Dermatol. Res.* 2010, 302, 710-725.
11) Miliner, J.; Patel, A.; Rowan, A. D. *Arthritis & Rheumatism* 2008, 58, 3644-3656.
12) Rovedatti, L.; Sabatino, A. F.; Knowles, C. H.; Sengupta, N.; Bioancheri, P.; Corazza, G. R.; MacDonald, T. T. *Inflamm. Bowel Dis.* 2011, 17, 5, 1251-1253.
13) Gorrell, M.; Song, S.; Xin, W. WO 2010/083570A1
14) Lee, K. N.; Jackson, K. W.; Christiansen, V. J.; Dolence, E. K.; McKee, P. A. *J. Thromb. Haemostas.* 2011, 9, 987-996.
15) Coutts, S. J.; Kelly, T. A.; Snow, R. J.; Kennedy, C. A.; Boston, R. W.; Adams, J.; Krolikowski, D. A.; Freeman, D. M.; Campbell, S. J.; Ksiazek, J. F.; Bachovchin, W. W. *J. Med. Chem.* 1996, 39, 2087-2094
16) (a) Bachovchin, W. W.; Lai, H. S. U.S. patent 2007, PCT/US2006/026258, (b) Evans, D. M.; Horton, J.; Trim, J. E. WO 2007085895 A2 20070802 (c) Tsai, T. Y; Yeh, T. K.; Chen, X.; Hsu, T.; Jao, Y. C.; Huang, C. H.; Song, J. S.; Huang, Y. C.; Chien, C. H.; Chiu, Y. H.; Yen, S. C.; Tang, H. K.; Chao, Y. S.; Jiaang, W. K. *J. Med. Chem.* 2010, 53, 6573-6583.
17) Kaila, N.; Janz, K.; De Bernardo, S.; Bedard, P. W.; Camphausen, R. T.; Tam, S.; Tsao, D. H. H.; Keith, J. C.; Nicherson-Nutter, C. C.; Shilling, A.; Young-Sciame, R.; Wang, Q. *J. Med. Chem.* 2007, 50, 21-39.
18) Van Goethem, S.; Matheeussen V.; Joossens, J.; Lambeir, A. M.; Chen, X.; De Meester, I.; Haemers, A.; Augustyns, K.; Van der Veken, P.; *J. Med. Chem.* 2011, doi 10.1021/jm200383j
19) Cheng J.; Dunbrack R. L.; Valianou M.; Rogatko, A.; Alpaugh, R. K.; Weiner, L. M. *Cancer Research* 2002; 62: 4767-4772
20) Brandt I, Gérard M, Sergeant K, Devreese B, Baekelandt V, Augustyns K, Scharpé S, Engelborghs Y, Lambeir A M. *Peptides* 2008, 29, 1472-1478

The invention claimed is:

1. A compound of Formula X or a stereoisomer, tautomer, racemic, salt, hydrate, or solvate thereof, Wherein $R_1$ and $R_2$ are each independently selected from the group consisting of —H, OH, -halo, $C_{1-6}$alkyl, —O—$C_{1-6}$alkyl, and S—$C_{1-6}$alkyl;

$R_3$ is selected from the group consisting of —H, —CN, —B(OH)$_2$, —C(O)alkyl, —C(O)aryl-, —C≡C—C(O)aryl, —C≡C—S(O)$_2$aryl, —CO$_2$H, —SO$_3$H, —SO$_2$NH$_2$, —PO$_3$H$_2$, and 5-tetrazolyl;

$R_4$ is —H;

$R_5$, $R_6$ and $R_7$ are each independently selected from the group consisting of —H, —OH, -oxo, -halo, —$C_{1-6}$alkyl, —O—$C_{1-6}$alkyl, —S—$C_{1-6}$alkyl, —$NR_8R_9$, —$OR_{12}$ -$Het_2$ and —$Ar_2$; each of said $C_{1-6}$alkyl being optionally substituted with from 1 to 3 substituents selected from —OH and -halo;

$R_8$, $R_9$ and $R_{12}$ are each independently selected from the group consisting of —H, —OH, -halo, —$C_{1-6}$alkyl, —O—$C_{1-6}$alkyl, —S—$C_{1-6}$alkyl, and —$Ar_3$;

$R_{10}$, $R_{11}$, $R_{13}$ and $R_{14}$ are each independently selected from the group consisting of —H, —OH, -halo, —$C_{1-6}$alkyl, —O—$C_{1-6}$alkyl, and —S—$C_{1-6}$alkyl;

$Ar_1$, $Ar_2$ and $Ar_3$ are each independently a 5- or 6-membered aromatic monocycle optionally comprising 1 or 2 heteroatoms selected from O, N and S; each of said $Ar_1$, $Ar_2$ and $Ar_3$ being optionally and independently substituted with from 1 to 3 substituents selected from —$NR_{10}R_{11}$, —$C_{1-6}$alkyl, —O—$C_{1-6}$alkyl, and —S—$C_{1-6}$alkyl;

$Het_2$ is a 5- or 6-membered non-aromatic monocycle optionally comprising 1 or 2 heteroatoms selected from O, N and S; said $Het_2$ being optionally substituted with from 1 to 3 substituents selected from —$NR_{13}R_{14}$, —$C_{1-6}$alkyl, —O—$C_{1-6}$alkyl, and —S—$C_{1-6}$alkyl;

n is 0, 1, 2, or 3; and

represents a 5 to 10-membered N-containing aromatic or non-aromatic mono- or bicyclic heterocycle, said heterocycle optionally further comprising 1, 2 or 3 heteroatoms selected from O, N and S.

2. The compound according to claim 1, and represented by Formula I or a stereoisomer, tautomer, racemic, salt, hydrate, or solvate thereof,

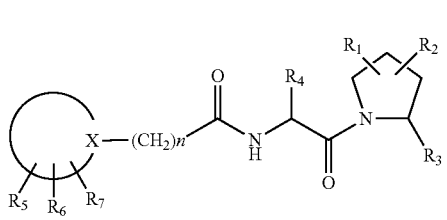

(I)

Wherein $R_1$ and $R_2$ are each independently selected from the group consisting of —H, OH, -halo, $C_{1-6}$alkyl, —O—$C_{1-6}$alkyl, and S—$C_{1-6}$alkyl;

$R_3$ is selected from the group consisting of —H, —CN, —$B(OH)_2$, —C(O)alkyl, —C(O)aryl-, —C≡C—C(O)aryl, —C≡C—$S(O)_2$aryl, —$CO_2H$, —$SO_3H$, —$SO_2NH_2$, —$PO_3H_2$, and 5-tetrazolyl;

$R_4$ is —H;

$R_5$, $R_6$ and $R_7$ are each independently selected from the group consisting of —H, —OH, -oxo, -halo, —$C_{1-6}$alkyl, —O—$C_{1-6}$alkyl, —S—$C_{1-6}$alkyl, —$NR_8R_9$, —$OR_{12}$ -$Het_2$ and —$Ar_2$; each of said $C_{1-6}$alkyl being optionally substituted with from 1 to 3 substituents selected from —OH and -halo;

$R_8$, $R_9$ and $R_{12}$ are each independently selected from the group consisting of —H, —OH, -halo, —$C_{1-6}$alkyl, —O—$C_{1-6}$alkyl, —S—$C_{1-6}$alkyl, and —$Ar_3$;

$R_{10}$, $R_{11}$, $R_{13}$ and $R_{14}$ are each independently selected from the group consisting of —H, —OH, -halo, —$C_{1-6}$alkyl, —O—$C_{1-6}$alkyl, and —S—$C_{1-6}$alkyl;

$Ar_1$, $Ar_2$ and $Ar_3$ are each independently a 5- or 6-membered aromatic monocycle optionally comprising 1 or 2 heteroatoms selected from O, N and S; each of said $Ar_1$, $Ar_2$ and $Ar_3$ being optionally and independently substituted with from 1 to 3 substituents selected from —$NR_{10}R_{11}$, —$C_{1-6}$alkyl, —O—$C_{1-6}$alkyl, —S—$C_{1-6}$alkyl;

$Het_2$ is a 5- or 6-membered non-aromatic monocycle optionally comprising 1 or 2 heteroatoms selected from O, N and S; said $Het_2$ being optionally substituted with from 1 to 3 substituents selected from —$NR_{13}R_{14}$, —$C_{1-6}$alkyl, —O—$C_{1-6}$alkyl, —S—$C_{1-6}$alkyl;

n is 0, 1, 2, or 3; and

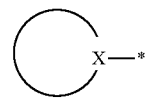

is selected from the group consisting of:

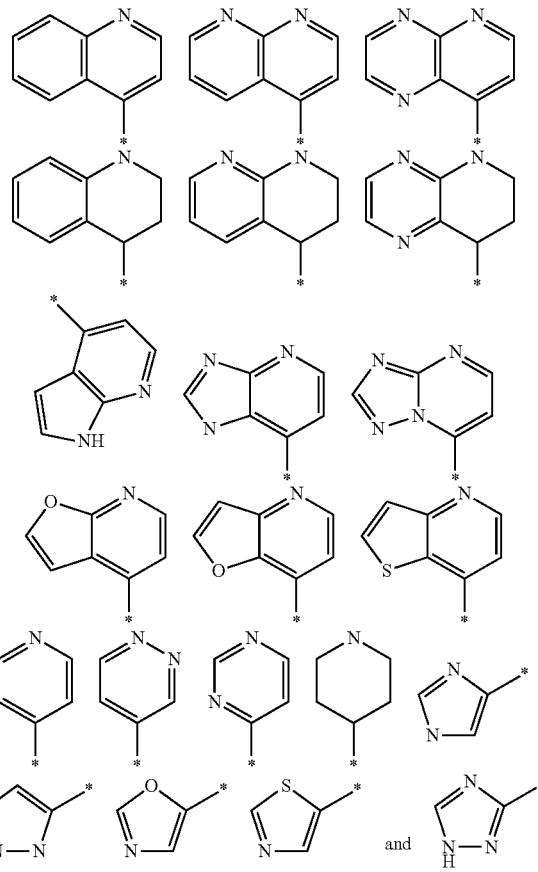

3. The compound according to claim 2, wherein:

$R_1$ and $R_2$ are each independently selected from the group consisting of —H and -halo;

$R_3$ is —CN or —$B(OH)_2$ $R_4$ is —H;

$R_5$, $R_6$ and $R_7$ are each independently selected from the group consisting of —H, —OH, -oxo, -halo, —$C_{1-6}$ alkyl, —O—C$_{1-6}$alkyl, Ar$_2$ and —NR$_8$R$_9$; each of said C$_{1-6}$alkyl being optionally substituted with from 1 to 3 substituents selected from —OH, -halo;

R$_8$ and R$_9$ are each independently selected from the group consisting of —H and —Ar$_3$ Ar$_2$ and Ar$_3$ are each independently -phenyl optionally substituted with from 1 to 3 —O—C$_{1-6}$alkyl;

n is 0 or 1; and

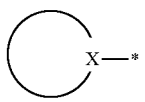

represents a 9 to 10-membered N-containing aromatic or non-aromatic bicyclic heterocycle selected from the group consisting of:

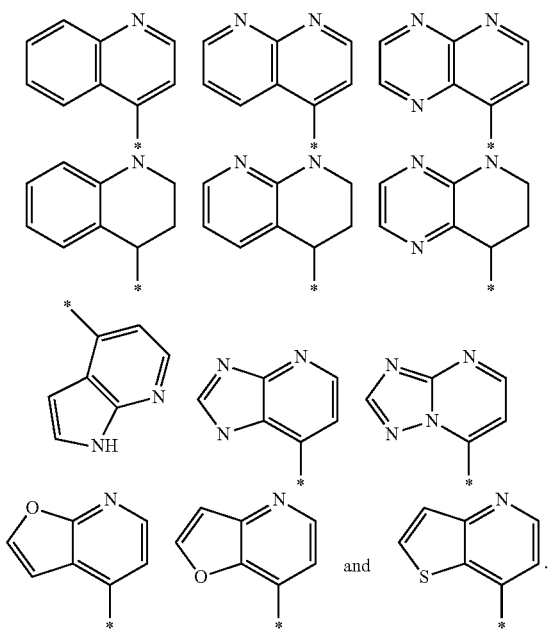

4. The compound according to claim 2, wherein

R$_1$ and R$_2$ are each independently selected from the group consisting of —H and —F;

R$_3$ is —CN or —B(OH)$_2$;

R$_4$ is —H;

R$_5$, R$_6$ and R$_7$ are each independently selected from the group consisting of —H, -oxo, -halo, —C$_{1-6}$alkyl, and —O—CF$_3$;

n is 0; and

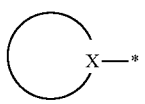

represents a 9 to 10-membered N-containing aromatic or non-aromatic bicyclic heterocycle selected from the group consisting of:

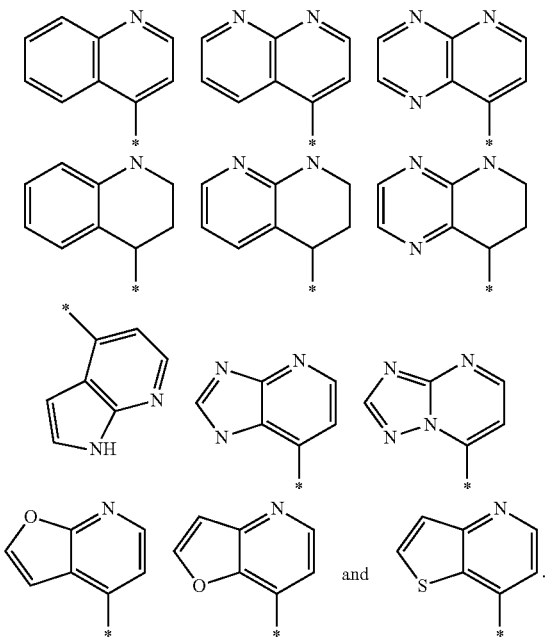

5. The compound according to claim 1 and represented by Formula II or a stereoisomer, tautomer, racemic, salt, hydrate, or solvate thereof,

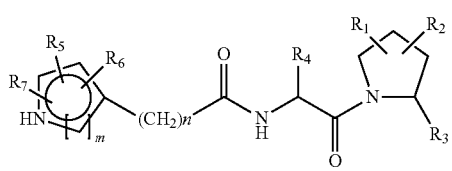

II wherein

R$_1$ and R$_2$ are each independently selected from the group consisting of —H, OH, -halo, C$_{1-6}$alkyl, —O—C$_{1-6}$alkyl, and S—C$_{1-6}$alkyl;

R$_3$ is selected from the group consisting of —H, —CN, and —B(OH)$_2$;

R$_4$ is —H;

R$_5$, R$_6$ and R$_7$ are each independently selected from the group consisting of —H, —OH, -oxo, -halo, —C$_{1-6}$alkyl, —O—C$_{1-6}$alkyl, —S—C$_{1-6}$alkyl, —NR$_8$R$_9$, and —Ar$_2$; each of said C$_{1-6}$alkyl being optionally substituted with from 1 to 3 substituents selected from —OH and -halo;

R$_8$, R$_9$, R$_{10}$ and R$_{11}$ are each independently selected from the group consisting of —H, —OH, -halo, —C$_{1-6}$alkyl, —O—C$_{1-6}$alkyl, and —S—C$_{1-6}$alkyl;

Ar$_2$ is a 5- or 6-membered aromatic monocycle optionally comprising 1 or 2 heteroatoms selected from O, N and S; Ar$_2$ being optionally and independently substituted with from 1 to 3 substituents selected from —NR$_{10}$R$_{11}$, —C$_{1-6}$alkyl, —O—C$_{1-6}$alkyl, and —S—C$_{1-6}$alkyl;

n is 0, 1, 2, or 3;

m is 1 or 2; and is selected from the group consisting of:

[structures: pyridine, pyridazine, pyrimidine, piperidine, imidazole, triazole, furan, thiophene, and triazole]

6. The compound according to claim 5, wherein:
R₅ and R₆ are each —H;
R₇ is selected from the group consisting of —H, —OH, -oxo, -halo, —C₁₋₆alkyl, —O—C₁₋₆alkyl, —S—C₁₋₆alkyl, —NR₈R₉, and —Ar₂; each of said C₁₋₆alkyl being optionally substituted with from 1 to 3 substituents selected from —OH, -halo; and
R₇ is attached to position 2 or 3 as represented in

[structure showing positions 1, 2, 3]

7. The compound according to claim 1 and represented by Formula IIIa, or a stereoisomer, tautomer, racemic, salt, hydrate, or solvate thereof,

[Formula IIIa structure]

wherein
R₁ and R₂ are each independently selected from the group consisting of —H, OH, -halo, C₁₋₆alkyl, —O—C₁₋₆alkyl, and S—C₁₋₆alkyl;
R₃ is selected from the group consisting of —H, —CN, —B(OH)₂, —C(O)alkyl, —C(O)aryl-, —C≡C—C(O)aryl, —C≡C—S(O)₂aryl, —CO₂H, —SO₃H, —SO₂NH₂, —PO₃H₂, and 5-tetrazolyl;
R₄ is —H;
R₅, R₆ and R₇ are each independently selected from the group consisting of —H, —OH, -oxo, -halo, —C₁₋₆alkyl, —O—C₁₋₆alkyl, —S—C₁₋₆alkyl, —NR₈R₉, and —Ar₂; each of said C₁₋₆alkyl being optionally substituted with from 1 to 3 substituents selected from —OH and -halo;
R₈ and R₉, are each independently selected from the group consisting of —H, —OH, -halo, —C₁₋₆alkyl, —O—C₁₋₆alkyl, —S—C₁₋₆alkyl, and —Ar₃;
R₁₀ and R₁₁ are each independently selected from the group consisting of —H, —OH, -halo, —C₁₋₆alkyl, —O—C₁₋₆alkyl, and —S—C₁₋₆alkyl;
Ar₁, Ar₂ and Ar₃ are each independently a 5- or 6-membered aromatic monocycle optionally comprising 1 or 2 heteroatoms selected from O, N and S; each of said Ar₁, and Ar₂ being optionally and independently substituted with from 1 to 3 substituents selected from —NR₁₀R₁₁, —C₁₋₆alkyl, —O—C₁₋₆alkyl, and —S—C₁₋₆alkyl;
n is 0, 1, 2, or 3;
m is 1 or 2; and

[bicyclic structure]

represents a 9 to 10-membered N-containing aromatic or non-aromatic bicyclic heterocycle optionally further comprising 1 or 2 heteroatoms selected from O, N and S.

8. The compound according to claim 7, wherein:
R₁ and R₂ are each independently selected from the group consisting of —H, OH, -halo, C₁₋₆alkyl, —O—C₁₋₆alkyl, and S—C₁₋₆alkyl;
R₃ is selected from the group consisting of —H, —CN, and —B(OH)₂;
R₄ is —H;
R₅, R₆ and R₇ are each independently selected from the group consisting of —H, —OH, -oxo, -halo, —C₁₋₆alkyl, —O—C₁₋₆alkyl, —S—C₁₋₆alkyl, —NR₈R₉, and —Ar₂; each of said C₁₋₆alkyl being optionally substituted with from 1 to 3 substituents selected from —OH, -halo;
R₈, R₉, R₁₀ and R₁₁ are each independently selected from the group consisting of —H, —OH, -halo, —C₁₋₆alkyl, —O—C₁₋₆alkyl, and —S—C₁₋₆ alkyl;
Ar₂ is a 5- or 6-membered aromatic monocycle optionally comprising 1 or 2 heteroatoms selected from O, N and S; Ar₂ being optionally and independently substituted with from 1 to 3 substituents selected from —NR₁₀R₁₁, —C₁₋₆alkyl, —O—C₁₋₆alkyl, and —S—C₁₋₆alkyl;
n is 0, 1, 2, or 3;
m is 1 or 2; and

[bicyclic structure]

is selected from the group consisting of:

[three bicyclic heteroaromatic structures: quinoline, naphthyridine, and quinoxaline derivatives]

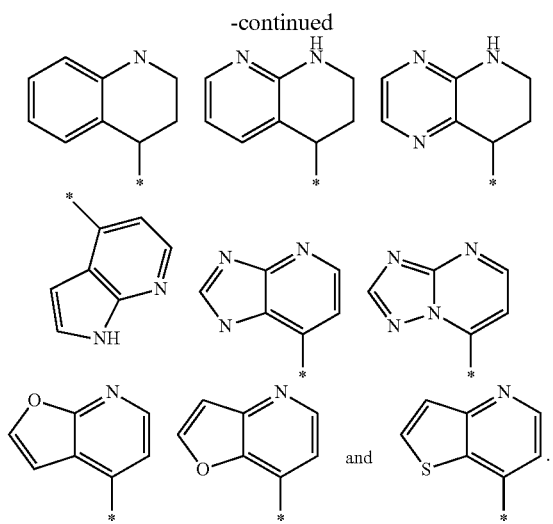

9. The compound according to claim 7, wherein $R_5$ is attached to position 2 or 3 as represented in

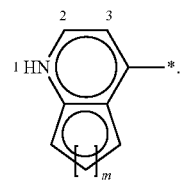

10. A composition comprising the compound according to claim 1, for use as a human or veterinary medicine.

11. A pharmaceutical composition comprising the compound according to claim 1, for use as a human or veterinary medicine.

12. A method for inhibiting the activity of fibroblast activation protein (FAP), the method comprising administering to a subject in need thereof an effective amount of the compound according to claim 1.

13. The pharmaceutical composition according to claim 11, further comprising one or more pharmaceutically acceptable carriers, diluents, excipients, or adjuvants.

* * * * *